(12) United States Patent
Brasca et al.

(10) Patent No.: US 8,993,556 B2
(45) Date of Patent: Mar. 31, 2015

(54) RESORCINOL DERIVATIVES AS HSP90 INHIBITORS

(75) Inventors: Maria Gabriella Brasca, Cusago (IT); Elena Casale, Somma Lombardo (IT); Ron Ferguson, Scotch Plains, NJ (US); Paolo Polucci, Cassina Rizzardi (IT); Fabio Zuccotto, Milan (IT)

(73) Assignee: Nerviano Medical Sciences S.R.L., Nerviano (MI) (IT)

( * ) Notice: Subject to any disclaimer, the term of this patent is extended or adjusted under 35 U.S.C. 154(b) by 0 days.

(21) Appl. No.: 13/264,888

(22) PCT Filed: Apr. 16, 2010

(86) PCT No.: PCT/EP2010/055026
§ 371 (c)(1),
(2), (4) Date: Oct. 17, 2011

(87) PCT Pub. No.: WO2010/121963
PCT Pub. Date: Oct. 28, 2010

(65) Prior Publication Data
US 2012/0046266 A1 Feb. 23, 2012

(30) Foreign Application Priority Data

Apr. 21, 2009 (EP) .................................... 09158367

(51) Int. Cl.
| | | |
|---|---|---|
| *C07D 231/14* | (2006.01) | |
| *C07D 261/14* | (2006.01) | |
| *C07D 261/18* | (2006.01) | |
| *C07D 413/12* | (2006.01) | |
| *C07D 413/14* | (2006.01) | |
| *C07D 453/02* | (2006.01) | |
| *A61K 31/42* | (2006.01) | |
| *A61K 31/454* | (2006.01) | |
| *A61K 31/439* | (2006.01) | |
| *A61K 31/496* | (2006.01) | |
| *A61K 31/5377* | (2006.01) | |

(52) U.S. Cl.
CPC ............ *C07D 231/14* (2013.01); *C07D 261/14* (2013.01); *C07D 261/18* (2013.01); *C07D 413/12* (2013.01); *C07D 413/14* (2013.01); *C07D 453/02* (2013.01)

USPC ................ 514/210.2; 514/236.8; 514/254.04; 514/305; 514/326; 514/378; 544/137; 544/367; 546/133; 546/209; 548/248; 548/374.1

(58) Field of Classification Search
None
See application file for complete search history.

(56) References Cited

U.S. PATENT DOCUMENTS 6,211,234 B1  4/2001  Astles et al.
7,115,750 B1  10/2006  Kato et al.

FOREIGN PATENT DOCUMENTS

| DE | 20 62 373 A1 | 7/1971 | |
|---|---|---|---|
| GB | 1 406 345 A | 9/1975 | |
| JP | 2006-306755 | * 11/2006 | ........... C07D 231/38 |
| WO | WO 03/053368 A2 | 7/2003 | |
| WO | WO 2004/072051 A1 | 8/2004 | |
| WO | WO 2008/097640 A2 | 8/2008 | |
| WO | WO 2009/066060 | * 5/2009 | ........... C07D 249/06 |

OTHER PUBLICATIONS

Machine translation of JP 2006-306755, accessed Feb. 9, 2014. Obtained from <http://worldwide.espacenet.com/>.*
Brough P.A. et al., "4,5-Diarylisoxazole Hsp90 Chaperone Inhibitors: Potential Therapeutic Agents for the Treatment of Cancer", *Journal of Medicinal Chemistry* 51(2):196-218 (2008), XP-002506225.
Brough P.A. et al., "3-(5-Chloro-2, 4-Dihydroxyphenyl)-Pyrazole-4-Carboxamides as Inhibitors of the Hsp90 Molecular Chaperone", *Bioorganic & Medicinal Chemistry Letters* 15(23):5197-5201 (Dec. 1, 2005), XP-025313816.
International Search Report dated Jul. 19, 2010 received from the European Patent Office from related International Application No. PCT/EP2010/055026.

* cited by examiner

*Primary Examiner* — Alicia L Otton
(74) *Attorney, Agent, or Firm* — Scully, Scott, Murphy & Presser, P.C.

(57) ABSTRACT

The present invention relates to substituted resorcinol derivatives which inhibit the activity of Heat Shock Protein HSP90. The compounds of the invention are therefore useful in treating proliferative diseases such as cancer and neurodegenerative diseases. The present invention also provides processes for preparing these compounds, pharmaceutical compositions comprising them, methods of treating diseases and the pharmaceutical compositions comprising these compounds.

5 Claims, No Drawings

RESORCINOL DERIVATIVES AS HSP90 INHIBITORS

The present invention relates to substituted resorcinol derivatives, which inhibit the activity of Heat Shock Protein HSP90. The compounds of the invention are therefore useful in treating proliferative diseases such as cancer and neurodegenerative diseases. The present invention also provides processes for preparing these compounds, pharmaceutical compositions comprising them, methods of treating diseases and the pharmaceutical compositions comprising these compounds.

The current targeted therapies for the treatment of cancer are based on the identification of specific proteins that drive tumour progression, and on the identification of a specific agent capable of antagonizing the effect of this protein. Most of the efforts of the pharma industry are directed towards a very limited number of well-validated protein targets. A common drawback is the arising of drug resistant mutations frequently found in cancer patients that are treated with these specific inhibitors. Recently, the common opinion is that the simultaneous block of signalling pathways involved in cancer progression is expected to determine a better anti-tumour efficacy, and also a lower probability to develop resistance. HSP90 belongs to a small family of proteins (GHKL, from DNA Gyrase, HSP90, histidine Kinase, mutL) sharing in common a very specific C shaped mode of binding to ATP (Bergerat fold). HSP90 is one of the most abundant proteins in cells, essential for viability in eukaryotes. The human cell contains four isoforms of HSP90: the cytosolic β-isoform, which is constitutively expressed, the inducible α-form, GRP94/gp96 in the endoplasmatic reticulum, and the mitochondrial TRAP1/HSP75. The α- and the β-form show 85% sequence identity.

HSP90 is a key component of a chaperone machinery, it catalyzes the folding and quality control of proteins, called HSP90 clients, in both normal cells and also under stress conditions. The chaperone activity, strictly dependent on the ATPase activity, is tightly regulated by the binding of other regulatory co-chaperones.

There are strong evidences that in disease conditions, such as cancer or other proliferative diseases, HSP90 becomes critical, due to the mutation or overexpression of specific oncogenes or also because tumors often have an overload of misfolded proteins that leads to an increased requirement of chaperone function.

Structurally HSP90 is an homodimer made of three main structured domains: an N terminal domain very conserved, the ATPase domain, a middle domain and a C terminal domain. The N and C terminal domains can bind ATP. Most of the currently known inhibitors such as geldanamycin, radicicol, diarylpyrazoles and purine derivatives show an ATP competitive binding to the N terminal ATP binding site, while novobiocin is the prototype of the inhibitors binding to the C terminal pocket.

At the moment there is an increasing number of reported HSP90 clients (Jolly, et al., J. Natl. Cancer Inst. 92; 1564-1572 (2000)), belonging to the family of kinases (Her2, B-RAF V600E, bcr-Abl, Flt3, NPM-ALK, Akt, Npm-Alk, ZAP-70), transcription factors (p53, HIF) telomerase, other chaperones, most of them strictly related with cancer progression. HSP90 inhibition impairs the capacity to fold or stabilize its client proteins, leading to the proteosomal dependent degradation of these unfolded proteins. The degradation of these client proteins is frequently used as a marker of HSP90 inhibition, typically used is the degradation of Her2 after compound treatment in Her2 overexpressing cells, such as BT474 breast cancer cells.

A big wave of research in the field of HSP90 inhibitors was driven initially by the evidence that the natural compound geldanamycin could actually block the proliferation of multiple tumour cells, by competitively binding to the N terminal ATP binding site and inhibiting the HSP90 ATPase activity and function. Surprisingly, this compound was not active in normal cells, may be because HSP90 is present in an active complex (with high affinity to geldanamycin) only in tumour cells (Kamal et al. Nature 425, 407-410 (2003)). Another potential reason for the selective sensitivity for tumours is the tumour retention that many HSP90 inhibitors show.

Tanespimycin (17-AAG), a semisynthetic derivative of geldanamycin (GDA), together with other related derivatives (alvespimycin, 17-DMAG, IPI-504) is under intense clinical evaluation, but the efficacy appear to be limited by a number of factors: cumbersome formulation, dependence on metabolism to generate the active metabolite, lack of patient enrichment, hepatic toxicity possibly related to the quinone moiety. This paved the way to an intense effort for the identification of second generation of HSP90 inhibitors with a better drug-like profile and better tolerability. This led to the identification of purine derivatives and diaryl-resorcinol derivatives.

The major cause of neurodegenerative diseases such as Alzheimer, Parkinson's, Huntington's, and prion disease is the accumulation of misfolded proteins that result in plaque formation. These misfolded proteins rely upon molecular chaperones (HSP70, HSP40, etc.) for rematuration, disaggregation, and resolubilization of protein aggregates. The heat shock proteins have been shown to provide this function in various cell culture models. HSPs can be induced by HSF1, which is tightly regulated by HSP90 in normal cells. It has been demonstrated that HSP90 inhibitors such as geldanamycin and the 17-AAG derivatives can disrupt this interaction and lead to HSP induction, resulting in neuroprotective activities and the resolubilization and disaggregation of misfolded proteins. HSP90 overexpression can significantly decrease the accumulation of misfolded proteins, which are responsible for Alzheimer's, in fact it has been demonstrated an inverse relationship between aggregated tau and HSP70/90 levels. Abnormal tau aggregation can be diminished (through degradation) by the overexpression of HSP70, HSP27, and HSP40, which is triggered by the inhibition of HSP90. Application of HSP90 inhibitors for the management of Parkinson's disease finds ground on the in vivo effect of GDA on 1-methyl-4-phenyl-1,2,3,6-tetrahydropyridine (MPTP)-induced neurotoxicity of a mouse model for Parkinson's disease. GDA protected the neurons from toxicity caused by MPTP, which was closely linked to increased HSP70 levels. In addition, it has been also shown that HSP90 overexpression can significantly decrease the accumulation of misfolded proteins, which are responsible for motor impairments, multiple sclerosis, spinal and bulbar muscular atrophy and other diseases.

4,6-Disubstituted resorcinol compounds with pharmacological activity were disclosed in GB1,406,345. Other patent applications describe phenyl-heterocyclic compounds as HSP90 inhibitors, all characterized by having a particular substitution pattern of the pentaheterocyclic ring, like WO2006/101052 in the name of Nippon Kayaku Kabushiki Kaisha; WO2005/000300, WO2004/072051 and WO2004/056782 of Vernalis; WO2003/055860 of Ribotargets, WO2008/097640 of Synta Pharmaceuticals and WO2005/063222 of Kyowa Hakko Kogyo.

Despite these developments, there is still need for effective agents for said diseases.

It has been found that compounds of formula (I) described below, are HSP90 inhibitors and are thus useful in therapy as antitumor and antineurodegenerative agents.

Accordingly, a first object of the present invention is to provide a compound of the formula (I):

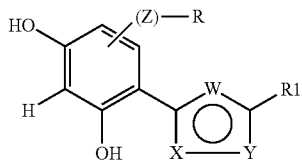

I wherein:
Z is —CH═CH—, —(CH$_2$)$_p$, wherein p is 0, 1, 2 or 3, NH, O, S, >S═O, >SO$_2$ or >C═O;
R is an optionally substituted linear or branched C$_1$-C$_7$ alkyl, C$_2$-C$_7$ alkenyl or C$_2$-C$_7$ alkynyl, C$_3$-C$_7$ cycloalkyl, C$_4$-C$_7$ cycloalkenyl, phenyl, napthyl, 5 or 6 membered heteroaryl, saturated or partially saturated heterocyclic ring comprising one or more oxygen, sulfur or nitrogen atom, or is a group CONHR$_2$, CH$_2$NHR$_2$, NHCOR$_2$, NHCONHR$_2$ wherein R$_2$ is an optionally substituted linear or branched C$_1$-C$_7$ alkyl, C$_2$-C$_7$ alkenyl or C$_2$-C$_7$ alkynyl, C$_3$-C$_7$ cycloalkyl, C$_4$-C$_7$ cycloalkenyl group, phenyl, napthyl, 5 or 6 membered heteroaryl, saturated or partially saturated heterocyclic ring comprising one or more oxygen, sulfur or nitrogen atom;
X is CH, N, NH or O;
W and Y are independently CH, N, NH, O or S;
R$_1$ is NH$_2$, NHCONHR$_2$, NHCOR$_2$, NHSO$_2$R$_2$, or CONHR$_2$, group, wherein R$_2$ is as defined above; the ring containing X, Y and W as defined above being a heteroaryl group, or a pharmaceutically acceptable salt thereof.

In particular, compounds of the formula (I) are 4-(1H-pyrazol-3-yl)benzene-1,3-diol derivatives if the meanings of X is NH, Y is N and W is CH, or X is N, Y is NH and W is CH; 4-(isoxazol-5-yl)benzene-1,3-diol derivatives if X, Y and W are respectively O, N and CH; 4-(isoxazol-3-yl)benzene-1,3-diol derivatives, if X, Y and W are respectively N, O and CH; 4-(1,3-oxazol-4-yl)benzene-1,3-diol derivatives, if X, Y and W are respectively CH, O and N; 4-(1,3-thiazol-4-yl)benzene-1,3-diol derivatives, if X, Y and W are respectively CH, S and N; 4-(1,3-thiazol-5-yl)benzene-1,3-diol derivatives, if X, Y and W are respectively CH, N and S; 4-(1,2,4-oxadiazol-3-yl)benzene-1,3-diol derivatives, if X and W are N and Y is O; 4-(1,3,4-oxadiazol-2-yl)benzene-1,3-diol derivatives, if X and Y are N and W is O and 4-(4H-1,2,4-triazol-3-yl)benzene-1,3-diol derivatives, if X is NH and Y and W are N, or Y is NH and X and W are N, or W is NH and X and Y are N.

As stated above, the compounds of the present invention are potent HSP90 inhibitors and are thus useful in anticancer and neurodegenerative diseases therapy.

The present invention also provides processes of synthesizing the resorcinol derivatives of formula (I) prepared through a process consisting of standard synthetic transformations.

The present invention also provides a method for treating diseases mediated by HSP90 protein.

A preferred method of the present invention is to treat a disease mediated by HSP90 protein selected from the group consisting of cancer and neurodegenerative disorders.

Another preferred method of the present invention is to treat specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocytic leukaemia, acute lymphoblastic leukaemia, B-cell lymphoma, T-cell-lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Another preferred method of the present invention is to treat specific types of neurodegenerative disorders including but not limited to: Alzheimer's, Parkinson's, Huntington's diseases, multiple sclerosis and spinal and bulbar muscular atrophy.

The present invention further provides a method of treatment comprising a compound of formula (I) in combination with radiation therapy or chemotherapy regimen for simultaneous, separate or sequential use in anticancer therapy. Moreover the invention provides an in vitro method for inhibiting HSP90 protein activity which comprises contacting the said protein with an effective amount of a compound of formula (I).

The present invention also provides a pharmaceutical composition comprising one or more compounds of formula (I) or a pharmaceutically acceptable salt thereof and a pharmaceutically acceptable excipient, carrier or diluent.

The present invention also provides a pharmaceutical composition comprising a compound of formula (I) in combination with known cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrix metalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

Additionally, the invention provides a product or kit comprising a compound of formula (I) or a pharmaceutically acceptable salt thereof, as defined above, or pharmaceutical compositions thereof and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament.

Moreover the invention provides the use of a compound of formula (I) or a pharmaceutically acceptable salt thereof, as defined above, in the manufacture of a medicament with antitumor activity.

Finally, the invention provides a compound of formula (I) or a pharmaceutically acceptable salt thereof, as defined above, for use in a method of treating a disease caused by and/or associated with an altered HSP90 activity, in particular cancer or a neurodegenerative disorder.

Unless otherwise specified, when referring to the compounds of formula (I) per se as well as to any pharmaceutical composition thereof or to any therapeutic treatment comprising them, the present invention includes all of the isomers, tautomers, hydrates, solvates, complexes, N-oxides and pharmaceutically acceptable salts of the compounds of this invention.

N-oxides are compounds of formula (I) wherein on one of the nitrogen atoms of the molecules there is an oxygen atom tethered through a dative bond. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form. Pharmaceutically acceptable salts of the compounds of formula (I) include the acid addition salts with inorganic or organic acids, e.g., nitric, hydrochloric, hydrobromic, sulfuric, perchloric, phosphoric, acetic, trifluoroacetic, propionic, glycolic, fumaric, lactic, oxalic, malonic, malic, maleic, tartaric, citric, benzoic, cinnamic, mandelic, methanesulphonic, isethionic and salicylic acid. Pharmaceutically acceptable salts of the compounds of formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines, preferably methylamine, ethylamine, diethylamine, triethylamine, piperidine and the like. As such, unless otherwise provided, when in compounds of formula (I), only one of the following tautomeric forms of formula (1a), (1b), (1c), (1d) or (1e) is indicated, the remaining one has still to be intended as comprised within the scope of the invention:

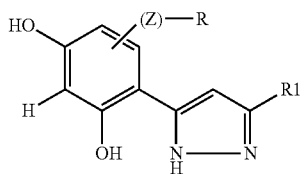

Ia

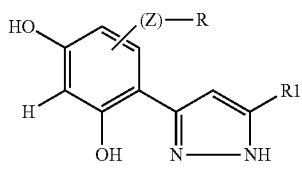

Ib

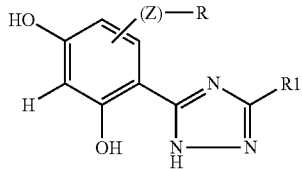

Ic

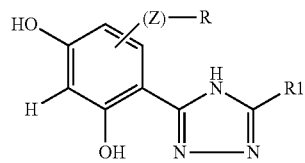

Id

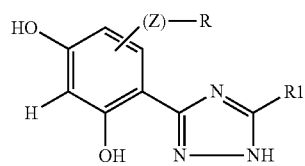

Ie wherein Z, R and $R_1$ are as defined above.

With the term halogen atom we intend a fluorine, chlorine, bromine or iodine atom.

With the term "straight or branched $C_1$-$C_7$ alkyl", we intend any of the groups such as, for instance, methyl, ethyl, n-propyl, isopropyl, n-butyl, isobutyl, tert-butyl, sec-butyl, n-pentyl, n-hexyl, and the like.

With the term "$C_2$-$C_7$ alkenyl" we intend an aliphatic $C_2$-$C_7$ hydrocarbon chain containing at least one carbon-carbon double bond and which can be straight or branched. Representative examples include, but are not limited to, ethenyl, 1-propenyl, 2-propenyl, 1- or 2-butenyl, and the like.

With the term "$C_2$-$C_7$ alkynyl" we intend an aliphatic $C_2$-$C_7$ hydrocarbon chain containing at least one carbon-carbon triple bond and which can be straight or branched. Representative examples include, but are not limited to, ethynyl, 1-propynyl, 2-propynyl, 1- or 2-butynyl, and the like.

With the term "$C_3$-$C_7$ cycloalkyl" we intend, unless otherwise provided, 3- to 7-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene and cyclohexadiene.

With the term "heterocyclyl" we intend a 3- to 8-membered, saturated or partially unsaturated carbocyclic ring where one or more carbon atoms are replaced by nitrogen, oxygen or sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated π-electron bond system. Non limiting examples of such aryl groups are phenyl, α- or β-naphthyl or biphenyl groups.

The term "heteroaryl" refers to aromatic heterocyclic rings, typically 5- to 8-membered heterocycles with from 1 to 3 heteroatoms selected among N, O or S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3- dihydrobenzothiophenyl; benzopyranyl, 2,3-dihydrobenzoxazinyl, 2,3-dihydroquinoxalinyl and the like.

According to the present invention and unless otherwise provided, any of the above R, $R_1$ and $R_2$ group may be optionally substituted, in any of their free positions, by one or more groups, for instance 1 to 6 groups, independently selected from: halogen, nitro, oxo groups (=O), cyano, $C_1$-$C_6$ alkyl, polyfluorinated alkyl, polyfluorinated alkoxy, $C_2$-$C_6$alkenyl, $C_2$-$C_6$ alkynyl, hydroxyalkyl, aryl, arylalkyl, heteroaryl, heteroarylalkyl, heterocyclyl, heterocyclylalkyl, $C_3$-$C_7$cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclylalkyloxycarbonylamino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate. In their turn, whenever appropriate, each of the above substituent may be further substituted by one or more of the aforementioned groups.

With the term polyfluorinated alkyl or polyfluorinated alkoxy we intend any of the above straight or branched $C_1$-$C_8$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term hydroxyalkyl we intend any of the above $C_1$-$C_8$alkyl, bearing an hydroxyl group such as, for instance, hydroxymethyl, 2-hydroxyethyl, 3-hydroxypropyl and the like.

From all of the above, it is clear to the skilled person that any group which name is a composite name such as, for instance, arylamino has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, $C_3$-$C_7$ cycloalkyl and heterocyclyl moieties are as above defined.

A preferred class of compounds of formula (I) are represented by compounds wherein X is NH, Y is N and W is CH, or X is N, Y is NH and W is CH, and Z, R and $R_1$ have the meanings above described, henceforth the 4-(1H-pyrazol-3-yl)benzene-1,3-diol derivatives.

Another preferred class of compounds of formula (I) are represented by compounds wherein X is O, Y is N, W is CH and Z, R and $R_1$ have the meanings above described, henceforth the 4-(isoxazol-5-yl)benzene-1,3-diol derivatives.

Another preferred class of compounds of formula (I) are represented by compounds wherein X is N, Y is O, W is CH and Z, R and $R_1$ have the meanings above described, henceforth the 4-(isoxazol-3-yl)benzene-1,3-diol derivatives.

Another preferred class of compounds of formula (I) are represented by compounds wherein X is CH, Y is O, W is N and Z, R and $R_1$ have the meanings above described, henceforth the 4-(1,3-oxazol-4-yl)benzene-1,3-diol derivatives.

Another preferred class of compounds of formula (I) are represented by compounds wherein X is CH, Y is S, W is N and Z, R and $R_1$ have the meanings above described, henceforth the 4-(1,3-thiazol-4-yl)benzene-1,3-diol derivatives.

Another preferred class of compounds of formula (I) are represented by compounds wherein X is CH, Y is N, W is S and Z, R and $R_1$ have the meanings above described, henceforth the 4-(1,3-thiazol-5-yl)benzene-1,3-diol derivatives.

Another preferred class of compounds of formula (I) are represented by compounds wherein X and W are N, Y is O, and Z, R and $R_1$ have the meanings above described, henceforth the 4-(1,2,4-oxadiazol-3-yl)benzene-1,3-diol derivatives.

Another preferred class of compounds of formula (I) are represented by compounds wherein X, Y are N, W is O, and Z, R and $R_1$ have the meanings above described, henceforth the 4-(1,3,4-oxadiazol-2-yl)benzene-1,3-diol derivatives.

Another preferred class of compounds of formula (I) are represented by compounds wherein X is NH and Y and W are N, or Y is NH and X and W are N, or W is NH and X and Y are N, and Z, R and $R_1$ have the meanings above described, henceforth the 4-(4H-1,2,4-triazol-3-yl)benzene-1,3-diol derivatives.

Specific compounds (cpd.) of the invention are listed below:
1. 5-[2,4-dihydroxy-6-(4-nitrophenoxy)phenyl]-N-ethylisoxazole-3-carboxamide,
2. 5-[2-(4-chlorophenoxy)-4,6-dihydroxyphenyl]-N-ethylisoxazole-3-carboxamide,
3. N-[1-(4,4-difluorocyclohexyl)piperidin-4-yl]-3-[2,4-dihydroxy-6-(4-nitrophenoxy)phenyl]isoxazole-5-carboxamide,
4. N-(1-azabicyclo[2.2.2]oct-3-yl)-5-[2,4-dihydroxy-6-(4-nitrophenoxy)phenyl]isoxazole-3-carboxamide,
5. 5-[2,4-dihydroxy-6-(4-nitrophenoxy)phenyl]-N-(2-hydroxyethyl)isoxazole-3-carboxamide,
6. 5-[2,4-dihydroxy-6-(4-nitrophenoxy)phenyl]-N-[2-(dimethylamino)ethyl]isoxazole-3-carboxamide,
7. 5-[2,4-dihydroxy-6-(4-nitrophenoxy)phenyl]-N-(2,2,2-trifluoroethyl)isoxazole-3-carboxamide,
8. 5-[2,4-dihydroxy-6-(4-nitrophenoxy)phenyl]-N-[2-(4-hydroxyphenyl)ethyl]isoxazole-3-carboxamide,
9. 5-[2,4-dihydroxy-6-(4-nitrophenoxy)phenyl]-N-(1-methylpiperidin-4-yl)isoxazole-3-carboxamide,
10. 5-[2,4-dihydroxy-6-(4-nitrophenoxy)phenyl]-N-(3-hydroxypropyl)isoxazole-3-carboxamide,
11. 5-[2,4-dihydroxy-6-(4-nitrophenoxy)phenyl]-N-(2-methoxyethyl)isoxazole-3-carboxamide,
12. 5-[2,4-dihydroxy-6-(4-nitrophenoxy)phenyl]-N-(3-methoxypropyl)isoxazole-3-carboxamide,
13. 5-[2,4-dihydroxy-6-(4-nitrophenoxy)phenyl]-N-(2-fluoroethyl)isoxazole-3-carboxamide,
14. N-[2-(acetylamino)ethyl]-5-[2,4-dihydroxy-6-(4-nitrophenoxy)phenyl]isoxazole-3-carboxamide,
15. 5-[2,4-dihydroxy-6-(4-nitrophenoxy)phenyl]-N-[3-(dimethylamino)propyl]isoxazole-3-carboxamide,
16. 5-[2,4-dihydroxy-6-(4-nitrophenoxy)phenyl]-N-[2-(1-methylpyrrolidin-2-yl)ethyl]isoxazole-3-carboxamide,
17. 5-[2,4-dihydroxy-6-(4-nitrophenoxy)phenyl]-N-[(1-methylpiperidin-4-yl)methyl]isoxazole-3-carboxamide,
18. N-(azetidin-3-ylmethyl)-5-[2,4-dihydroxy-6-(4-nitrophenoxy)phenyl]isoxazole-3-carboxamide,
19. 5-[2,4-dihydroxy-6-(4-nitrophenoxy)phenyl]-N,N-dimethylisoxazole-3-carboxamide, 20. 5-[2-(4-aminophenoxy)-4,6-dihydroxyphenyl]-N-ethyl-isoxazole-3-carboxamide,
21. 5-[2,4-dihydroxy-6-(4-nitrophenoxy)phenyl]-N-(furan-2-ylmethyl)isoxazole-3-carboxamide,
22. N-benzyl-5-[2,4-dihydroxy-6-(4-nitrophenoxy)phenyl]isoxazole-3-carboxamide,
23. N-(cyclohexylmethyl)-5-[2,4-dihydroxy-6-(4-nitrophenoxy)phenyl]isoxazole-3-carboxamide,
24. 5-[2,4-dihydroxy-6-(4-nitrophenoxy)phenyl]-N-[3-(1H-imidazol-1-yl)propyl]isoxazole-3-carboxamide,
25. 5-[2,4-dihydroxy-6-(4-nitrophenoxy)phenyl]-N-[2-(piperidin-1-yl)ethyl]isoxazole-3-carboxamide,
26. 5-[2,4-dihydroxy-6-(4-nitrophenoxy)phenyl]-N-[2-(morpholin-4-yl)ethyl]isoxazole-3-carboxamide,
27. 5-[2,4-dihydroxy-6-(4-nitrophenoxy)phenyl]-N-[3-(2-oxopyrrolidin-1-yl)propyl]isoxazole-3-carboxamide,
28. 5-[2,4-dihydroxy-6-(4-nitrophenoxy)phenyl]-N-[3-(4-methylpiperazin-1-yl)propyl]isoxazole-3-carboxamide, tert-butyl,
29. {2-[({5-[2,4-dihydroxy-6-(4-nitrophenoxy)phenyl]isoxazol-3-yl}carbonyl)amino]ethyl}methylcarbamate,
30. N-(trans-4-aminocyclohexyl)-5-[2,4-dihydroxy-6-(4-nitrophenoxy)phenyl]isoxazole-3-carboxamide,
31. 5-[2,4-dihydroxy-6-(4-nitrophenoxy)phenyl]-N-(trans-4-hydroxycyclohexyl)isoxazole-3-carboxamide,
32. tert-butyl 4-[({5-[2,4-dihydroxy-6-(4-nitrophenoxy)phenyl]isoxazol-3-yl}carbonyl)amino]piperidine-1-carboxylate,
33. 5-[2,4-dihydroxy-6-(4-nitrophenoxy)phenyl]-N-(piperidin-4-yl)isoxazole-3-carboxamide,
34. 5-[2,4-dihydroxy-6-(4-nitrophenoxy)phenyl]-N-(1-methylpiperidin-4-yl)isoxazole-3-carboxamide,
35. N-cyclohexyl-5-[2,4-dihydroxy-6-(4-nitrophenoxy)phenyl]isoxazole-3-carboxamide,
36. 5-[2,4-dihydroxy-6-(4-nitrophenoxy)phenyl]-N-[2-(methylamino)ethyl]isoxazole-3-carboxamide,
37. 5-{2-[4-(benzylamino)phenoxy]-4,6-dihydroxyphenyl}-N-ethylisoxazole-3-carboxamide,
38. 5-{2-[4-(acetylamino)phenoxy]-4,6-dihydroxyphenyl}-N-ethylisoxazole-3-carboxamide,
39. 5-[2-(4-amino-3-chlorophenoxy)-4,6-dihydroxyphenyl]-N-ethylisoxazole-3-carboxamide,
40. 5-{2-[4-(dimethylamino)phenoxy]-4,6-dihydroxyphenyl}-N-ethylisoxazole-3-carboxamide,
41. 5-[2,4-dihydroxy-6-(4-nitrophenoxy)phenyl]-N-(1-methylpiperidin-4-yl)isoxazole-3-carboxamide,
42. 5-[2,4-dihydroxy-6-(4-nitrophenoxy)phenyl]-N-(1-methylpiperidin-4-yl)isoxazole-3-carboxamide,
43. 5-{2,4-dihydroxy-6-[4-(propan-2-ylamino)phenoxy]phenyl}-N-ethylisoxazole-3-carboxamide,
44. 5-[2,4-dihydroxy-6-(4-nitrophenoxy)phenyl]-N-(piperidin-4-yl)isoxazole-3-carboxamide,
45. 5-[2,4-dihydroxy-6-(4-nitrophenoxy)phenyl]-N-[1-(propan-2-yl)piperidin-4-yl]isoxazole-3-carboxamide,
46. N-(1-cyclohexylpiperidin-4-yl)-5-[2,4-dihydroxy-6-(4-nitrophenoxy)phenyl]isoxazole-3-carboxamide,
47. 5-[2,4-dihydroxy-6-(4-nitrophenoxy)phenyl]-N-[1-(4-hydroxycyclohexyl)piperidin-4-yl]isoxazole-3-carboxamide,
48. 5-[2,4-dihydroxy-6-(4-nitrophenoxy)phenyl]-N-[1-(4-methoxycyclohexyl)piperidin-4-yl]isoxazole-3-carboxamide,
49. 5-[2,4-dihydroxy-6-(4-nitrophenoxy)phenyl]-N-[1-(4-aminocyclohexyl)piperidin-4-yl]isoxazole-3-carboxamide,
50. 5-[2,4-dihydroxy-6-(4-nitrophenoxy)phenyl]-N-[1-(4-(dimethylamino)cyclohexyl)piperidin-4-yl]isoxazole-3-carboxamide,
51. 5-[2,4-dihydroxy-6-(4-nitrophenoxy)phenyl]-N-[1-(4-acetylamino)cyclohexyl)piperidin-4-yl]isoxazole-3-carboxamide,
52. 5-[2,4-dihydroxy-6-(4-nitrophenoxy)phenyl]-N-[1-(4-aminomethyl)cyclohexyl)piperidin-4-yl]isoxazole-3-carboxamide,
53. 5-[2,4-dihydroxy-6-(4-nitrophenoxy)phenyl]-N-[1-(4-dimethylaminomethyl)cyclohexyl)piperidin-4-yl]isoxazole-3-carboxamide,
54. N-[1-(4,4-difluorocyclohexyl)piperidin-4-yl]-5-[2,4-dihydroxy-6-(4-nitrophenoxy)phenyl]isoxazole-3-carboxamide,
55. 5-[2,4-dihydroxy-6-(4-nitrophenoxy)phenyl]-N-[1-(1,4-dioxaspiro[4.5]dec-8-yl)piperidin-4-yl]isoxazole-3-carboxamide,
56. 5-[2,4-dihydroxy-6-(4-nitrophenoxy)phenyl]-N-(1'-methyl-1,4'-bipiperidin-4-yl)isoxazole-3-carboxamide,
57. 5-[2,4-dihydroxy-6-(4-nitrophenoxy)phenyl]-N-[1-(tetrahydro-2H-pyran-4-yl)piperidin-4-yl]isoxazole-3-carboxamide,
58. 5-[2,4-dihydroxy-6-(4-dimethylaminophenoxy)phenyl]-N-[1-(4-hydroxycyclohexyl)piperidin-4-yl]isoxazole-3-carboxamide,
59. 5-[2,4-dihydroxy-6-(4-dimethylaminophenoxy)phenyl]-N-[1-(4-methoxycyclohexyl)piperidin-4-yl]isoxazole-3-carboxamide,
60. 5-[2,4-dihydroxy-6-(4-dimethylaminophenoxy)phenyl]-N-[1-(4-aminocyclohexyl)piperidin-4-yl]isoxazole-3-carboxamide,
61. 5-[2,4-dihydroxy-6-(4-dimethylaminophenoxy)phenyl]-N-[1-(4-(dimethylamino)cyclohexyl)piperidin-4-yl]isoxazole-3-carboxamide,
62. 5-[2,4-dihydroxy-6-(4-dimethylaminophenoxy)phenyl]-N-[1-(4-acetylamino)cyclohexyl)piperidin-4-yl]isoxazole-3-carboxamide,
63. 5-[2,4-dihydroxy-6-(4-dimethylaminophenoxy)phenyl]-N-[1-(4-aminomethyl)cyclohexyl)piperidin-4-yl]isoxazole-3-carboxamide,
64. 5-[2,4-dihydroxy-6-(4-dimethylaminophenoxy)phenyl]-N-[1-(4-dimethylaminomethyl)cyclohexyl)piperidin-4-yl]isoxazole-3-carboxamide,
65. N-[1-(4,4-difluorocyclohexyl)piperidin-4-yl]-5-[2,4-dihydroxy-6-(4-dimethylaminophenoxy)phenyl]isoxazole-3-carboxamide,
66. N-[1-(4,4-difluorocyclohexyl)piperidin-4-yl]-5-[2,4-dihydroxy-6-(4-(propan-2-yl-amino)phenoxy)phenyl]isoxazole-3-carboxamide,
67. 5-[2,4-dihydroxy-6-(4-(propan-2-yl-amino)phenoxy)phenyl]-N-[1-(1,4-dioxaspiro[4.5]dec-8-yl)piperidin-4-yl]isoxazole-3-carboxamide,
68. 5-[2,4-dihydroxy-6-(4-(propan-2-yl-amino)phenoxy)phenyl]-N-(1-methyl-1,4'-bipiperidin-4-yl)isoxazole-3-carboxamide,
69. 5-[2,4-dihydroxy-6-(4-(propan-2-yl-amino)phenoxy)phenyl]-N-[1-(tetrahydro-2H-pyran-4-yl)piperidin-4-yl]isoxazole-3-carboxamide,
70. N-(1-cyclohexylpiperidin-4-yl)-5-[2,4-dihydroxy-6-(4-cyanophenoxy)phenyl]isoxazole-3-carboxamide,
71. 5-[2,4-dihydroxy-6-(4-cyanophenoxy)phenyl]-N-[1-(4-hydroxycyclohexyl)piperidin-4-yl]isoxazole-3-carboxamide,
72. 5-[2,4-dihydroxy-6-(4-cyanophenoxy)phenyl]-N-[1-(4-methoxycyclohexyl)piperidin-4-yl]isoxazole-3-carboxamide, 73. 5-[2,4-dihydroxy-6-(4-cyanophenoxy)phenyl]-N-[1-(4-aminocyclohexyl)piperidin-4-yl]isoxazole-3-carboxamide,
74. 5-[2,4-dihydroxy-6-(4-cyanophenoxy)phenyl]-N-[1-(4-dimethylaminocyclohexyl)piperidin-4-yl]isoxazole-3-carboxamide,
75. 5-[2,4-dihydroxy-6-(4-cyanophenoxy)phenyl]-N-[1-(4-acetylaminocyclohexyl)piperidin-4-yl]isoxazole-3-carboxamide,
76. 5-[2,4-dihydroxy-6-(4-cyanophenoxy)phenyl]-N-[1-(4-aminomethylcyclohexyl)piperidin-4-yl]isoxazole-3-carboxamide,
77. 5-[2,4-dihydroxy-6-(4-cyanophenoxy)phenyl]-N-[1-(4-dimethylaminomethylcyclohexyl)piperidin-4-yl]isoxazole-3-carboxamide,
78. N-[1-(4,4-difluorocyclohexyl)piperidin-4-yl]-5-[2,4-dihydroxy-6-(4-cyanophenoxy)phenyl]isoxazole-3-carboxamide,
79. 5-[2,4-dihydroxy-6-(4-cyanophenoxy)phenyl]-N-[1-(1,4-dioxaspiro[4.5]dec-8-yl)piperidin-4-yl]isoxazole-3-carboxamide,
80. 5-[2,4-dihydroxy-6-(4-cyanophenoxy)phenyl]-N-(1'-methyl-1,4'-bipiperidin-4-yl)isoxazole-3-carboxamide,
81. 5-[2,4-dihydroxy-6-(4-cyanophenoxy)phenyl]-N-[1-(tetrahydro-2H-pyran-4-yl)piperidin-4-yl]isoxazole-3-carboxamide,
82. N-(1-cyclohexylpiperidin-4-yl)-5-[2,4-dihydroxy-6-(4-carbamoylphenoxy)phenyl]isoxazole-3-carboxamide,
83. 5-[2,4-dihydroxy-6-(4-(propan-2-yl-amino)phenoxy)phenyl]-N-[1-(4-hydroxycyclohexyl)piperidin-4-yl]isoxazole-3-carboxamide,
84. 5-[2,4-dihydroxy-6-(4-carbamoylphenoxy)phenyl]-N-[1-(4-methoxycyclohexyl)piperidin-4-yl]isoxazole-3-carboxamide,
85. 5-[2,4-dihydroxy-6-(4-carbamoylphenoxy)phenyl]-N-[1-(4-aminocyclohexyl)piperidin-4-yl]isoxazole-3-carboxamide,
86. 5-[2,4-dihydroxy-6-(4-carbamoylphenoxy)phenyl]-N-[1-(4-(dimethylamino)cyclohexyl)piperidin-4-yl]isoxazole-3-carboxamide,
87. 5-[2,4-dihydroxy-6-(4-carbamoylphenoxy)phenyl]-N-[1-(4-(acetylamino)cyclohexyl)piperidin-4-yl]isoxazole-3-carboxamide,
88. 5-[2,4-dihydroxy-6-(4-carbamoylphenoxy)phenyl]-N-[1-(4-(aminomethyl)cyclohexyl)piperidin-4-yl]isoxazole-3-carboxamide,
89. 5-[2,4-dihydroxy-6-(4-carbamoylphenoxy)phenyl]-N-[1-(4-dimethylaminomethyl)cyclohexyl)piperidin-4-yl]isoxazole-3-carboxamide,
90. N-[1-(4,4-difluorocyclohexyl)piperidin-4-yl]-5-[2,4-dihydroxy-6-(4-carbamoylphenoxy)phenyl]isoxazole-3-carboxamide,
91. 5-[2,4-dihydroxy-6-(4-carbamoylphenoxy)phenyl]-N-[1-(1,4-dioxaspiro[4.5]dec-8-yl)piperidin-4-yl]isoxazole-3-carboxamide,
92. 5-[2,4-dihydroxy-6-(4-carbamoylphenoxy)phenyl]-N-(1'-methyl-1,4'-bipiperidin-4-yl)isoxazole-3-carboxamide,
93. 5-[2,4-dihydroxy-6-(4-carbamoylphenoxy)phenyl]-N-[1-(tetrahydro-2H-pyran-4-yl)piperidin-4-yl]isoxazole-3-carboxamide,
94. 3-[2-(4-carbamoylphenoxy)-4,6-dihydroxyphenyl]-N-[1-(tetrahydro-2H-pyran-4-yl)piperidin-4-yl]isoxazole-5-carboxamide,
95. 3-[2-(4-carbamoylphenoxy)-4,6-dihydroxyphenyl]-N-(1-cyclohexylpiperidin-4-yl)isoxazole-5-carboxamide,
96. 3-[2-(4-carbamoylphenoxy)-4,6-dihydroxyphenyl]-N-[1-(4,4-difluorocyclohexyl)piperidin-4-yl]isoxazole-5-carboxamide,
97. 3-[2-(4-carbamoylphenoxy)-4,6-dihydroxyphenyl]-N-(1-methyl-1,4'-bipiperidin-4-yl)isoxazole-5-carboxamide,
98. N-(1-cyclohexylpiperidin-4-yl)-3-[2,4-dihydroxy-6-(4-nitrophenoxy)phenyl]isoxazole-5-carboxamide,
99. 3-[2,4-dihydroxy-6-(4-nitrophenoxy)phenyl]-N-[1-(tetrahydro-2H-pyran-4-yl)piperidin-4-yl]isoxazole-5-carboxamide,
100. 3-[2,4-dihydroxy-6-(4-nitrophenoxy)phenyl]-N-(1-methyl-1,4'-bipiperidin-4-yl)isoxazole-5-carboxamide,
101. 5-[2,4-dihydroxy-6-(4-nitrophenoxy)phenyl]-N-[2-(methylamino)ethyl]isoxazole-3-carboxamide,
102. 5-[2,4-dihydroxy-6-(4-nitrophenoxy)phenyl]-N-(1-ethylpiperidin-3-yl)isoxazole-3-carboxamide,
103. N-(1-acetylpiperidin-4-yl)-5-[2,4-dihydroxy-6-(4-nitrophenoxy)phenyl]isoxazole-3-carboxamide,
104. 5-[2,4-dihydroxy-6-(4-nitrophenoxy)phenyl]-(1,2,2,6,6-pentamethylpiperidin-4-yl)isoxazole-3-carboxamide,
105. 5-[2,4-dihydroxy-6-(4-nitrophenoxy)phenyl]-N-(piperidin-4-yl)isoxazole-3-carboxamide,
106. N-(1-cyclopentylpiperidin-4-yl)-5-[2,4-dihydroxy-6-(4-nitrophenoxy)phenyl]isoxazole-3-carboxamide,
107. N-(1-cycloheptylpiperidin-4-yl)-5-[2,4-dihydroxy-6-(4-nitrophenoxy)phenyl]isoxazole-3-carboxamide,
108. N-(1-benzylpiperidin-4-yl)-5-[2,4-dihydroxy-6-(4-nitrophenoxy)phenyl]isoxazole-3-carboxamide,
109. N-(1-cyclohexylpiperidin-4-yl)-5-{2-[4-(dimethylamino)phenoxy]-4,6-dihydroxyphenyl}isoxazole-3-carboxamide-1,3-dioxolane,
110. 5-{2-[4-(dimethylamino)phenoxy]-4,6-dihydroxyphenyl}-N-[1-(1,5-dioxaspiro[5.5]undec-9-yl)piperidin-4-yl]isoxazole-3-carboxamide,
111. 5-{2-[4-(dimethylamino)phenoxy]-4,6-dihydroxyphenyl}-N-[1-(3,3-dimethyl-1,5-dioxaspiro[5.5]undec-9-yl)piperidin-4-yl]isoxazole-3-carboxamide,
112. 5-{2-[4-(dimethylamino)phenoxy]-4,6-dihydroxyphenyl}-N-[1-(7,12-dioxaspiro[5.6]dodec-3-yl)piperidin-4-yl]isoxazole-3-carboxamide,
113. 5-{2-[4-(dimethylamino)phenoxy]-4,6-dihydroxyphenyl}-N-{1-[(2R,3S)-2,3-dimethyl-1,4-dioxaspiro[4.5]dec-8-yl]piperidin-4-yl}isoxazole-3-carboxamide,
114. N-[1-(4,4-difluorocyclohexyl)piperidin-4-yl]-5-{2-[4-(dimethylamino)phenoxy]-4,6-dihydroxyphenyl}isoxazole-3-carboxamide,
115. N-[1'-(cyclohexylmethyl)-1,4'-bipiperidin-4-yl]-5-{2-[4-(dimethylamino)phenoxy]-4,6-dihydroxyphenyl}isoxazole-3-carboxamide,
116. N-(1-benzyl-1,4'-bipiperidin-4-yl)-5-{2-[4-(dimethylamino)phenoxy]-4,6-dihydroxyphenyl}isoxazole-3-carboxamide,
117. tert-butyl(4-{-4-[({5-[2,4-dihydroxy-6-(4-nitrophenoxy)phenyl]isoxazol-3-yl}carbonyl)amino]piperidin-1-yl}butyl)carbamate,
118. N-[1-(4-aminobutyl)piperidin-4-yl]-5-[2,4-dihydroxy-6-(4-nitrophenoxy)phenyl]isoxazole-3-carboxamide
119. tert-butyl(3-{-4-[({5-[2,4-dihydroxy-6-(4-nitrophenoxy)phenyl]isoxazol-3-yl}carbonyl)amino]piperidin-1-yl}propyl)carbamate,
120. N-[1-(3-aminopropyl)piperidin-4-yl]-5-[2,4-dihydroxy-6-(4-nitrophenoxy)phenyl]isoxazole-3-carboxamide,
121. 5-{2,4-dihydroxy-6-[4-(tetrahydro-2H-pyran-4-ylamino)phenoxy]phenyl}-N-(1-methylpiperidin-4-yl)isoxazole-3-carboxamide, 122. 5-{2-[4-(dimethylamino)phenoxy]-4,6-dihydroxyphenyl}-N-(1-methylpiperidin-4-yl)isoxazole-3-carboxamide,
123. 5-{2,4-dihydroxy-6-[4-(propan-2-ylamino)phenoxy]phenyl}-N-(1-methylpiperidin-4-yl)isoxazole-3-carboxamide,
124. 5-{2-[4-(cyclobutylamino)phenoxy]-4,6-dihydroxyphenyl}-N-(1-methylpiperidin-4-yl)isoxazole-3-carboxamide,
125. 5-{2,4-dihydroxy-6-[4-(pyrrolidin-1-yl)phenoxy]phenyl}-N-(1-methylpiperidin-4-yl)isoxazole-3-carboxamide,
126. 3-[2,4-dihydroxy-6-(4-nitrophenoxy)phenyl]-N-(1-methylpiperidin-4-yl)isoxazole-5-carboxamide,
127. 3-[2,4-dihydroxy-6-(4-nitrophenoxy)phenyl]-N-(1-methylpiperidin-4-yl)isoxazole-5-carboxamide,
128. 3-{2-[4-(dimethylamino)phenoxy]-4,6-dihydroxyphenyl}-N-(1-methylpiperidin-4-yl)isoxazole-5-carboxamide,
129. tert-butyl 4-{[(3-{2-[4-(dimethylamino)phenoxy]-4,6-dihydroxyphenyl}isoxazol-5-yl)carbonyl]amino}piperidine-1-carboxylate,
130. 3-{2-[4-(dimethylamino)phenoxy]-4,6-dihydroxyphenyl}-N-(piperidin-4-yl)isoxazole-5-carboxamide,
131. 3-{2-[4-(dimethylamino)phenoxy]-4,6-dihydroxyphenyl}-N-[1-(1,4-dioxaspiro[4.5]dec-8-yl)piperidin-4-yl]isoxazole-5-carboxamide,
132. 3-{2-[4-(dimethylamino)phenoxy]-4,6-dihydroxyphenyl}-N-[1-(3,3-dimethyl-1,5-dioxaspiro[5.5]undec-9-yl)piperidin-4-yl]isoxazole-5-carboxamide,
133. 5-[2-(benzyloxy)-4,6-dihydroxyphenyl]-N-(1-methylpiperidin-4-yl)isoxazole-3-carboxamide,
134. 4-(3-aminoisoxazol-5-yl)-5-(4-nitrophenoxy)benzene-1,3-diol,
135. 1-{5-[2,4-dihydroxy-6-(4-nitrophenoxy)phenyl]isoxazol-3-yl}-3(1-methylpiperidin-4-yl)urea,
136. N-{5-[2,4-dihydroxy-6-(4-nitrophenoxy)phenyl]isoxazol-3-yl}-1-methylpiperidine-4-carboxamide and
137. N-{5-[2,4-dihydroxy-6-(4-nitrophenoxy)phenyl]isoxazol-3-yl}ethanesulfonamide.

The present invention also provides a process for the preparation of a compound of formula (I) as defined above, characterized in that the process comprises:

1a) condensing a compound of formula (II):

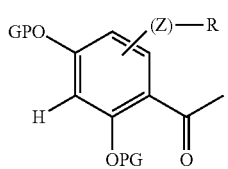

wherein PG represents a benzyl (Bn), methyl (Me), methoxymethyl (MOM) or 2-methoxyethoxymethyl (MEM) group and Z and R are as defined above, with ethyl oxalate in presence of a base such as sodium hydride, sodium ethoxide, lithium (bis trimethylsilylamide in a solvent such as tetrahydrofurane (THF), dioxane;

1b) reacting the resultant compound of formula (III):

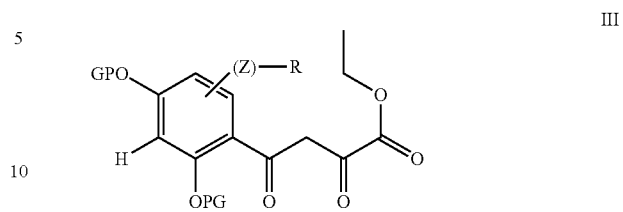

wherein PG, Z and R are as defined above, with hydrazine hydrate (NH$_2$NH$_2$.H$_2$O), hydrazine hydrochloride (NH$_2$NH$_2$.HCl) or hydrazine sulphate (NH$_2$NH$_2$.H$_2$SO$_4$) in a solvent such as ethanol, THF, acetic acid, pyridine to give a compound of formula (IV):

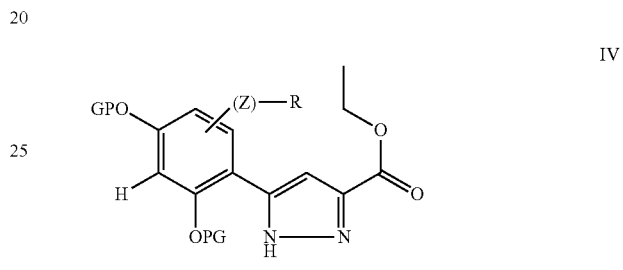

wherein PG, Z and R are as defined above;

or 1'b) reacting a compound of formula (III) as defined above with hydroxylamine hydrochloride (NH$_2$OH.HCl) or hydroxylamine sulphate (NH$_2$OH.H$_2$SO$_4$) in a solvent such as pyridine, ethanol, to give a compound of formula (V):

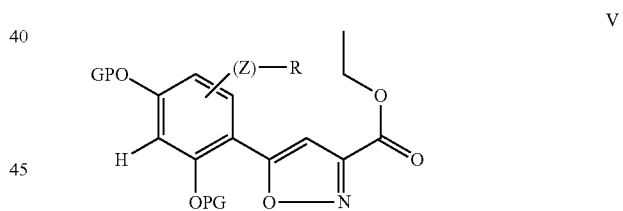

wherein PG, Z and R are as above defined;

or 2a) reacting a compound of formula (VI):

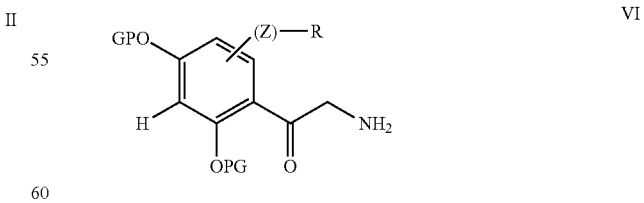

wherein PG, Z and R are as defined above, with CH$_3$CH$_2$OCOCOCl, in a solvent such as THF, pyridine, dioxane in presence of a organic base such as triethylamine (TEA), 4-methyl morpholine, ethyldiisopropylamine (DIPEA) and 2b) reacting the resultant compound of formula (VII):

VII wherein PG, Z and R are as defined above, with POCl$_3$ in a solvent such as CHCl$_3$, pyridine, THF, to give a compound of formula (VIII):

VIII wherein PG, Z and R are as defined above;
or 2'b) reacting a compound of formula (VII) as describe above, with P$_2$S$_5$ in a solvent such as CHCl$_3$, pyridine, toluene, to give a compound of formula (IX):

IX wherein PG, Z and R are as above defined;
either 3a) reacting a compound of formula (X):

X wherein PG, Z and R are as defined above, with H$_2$S in a solvent such as pyridine in presence of TEA to give a compound of formula (XI):
3b) reacting the resultant compound of formula (XI):

XI wherein PG, Z and R are as defined above, with HCOCHClCOOCH$_2$CH$_3$ in a solvent such as THF, dioxane or ethanol, to give a compound of formula (XII):

XII wherein PG, Z and R are as defined above;
or 3'a) reacting a compound of formula (X) as defined above with NH$_2$OH.HCl in a solvent such as methanol or ethanol, in the presence of sodium carbonate or potassium carbonate, and 3'b) reacting the resultant compound of formula (XIII):

XIII wherein PG, Z and R are as defined above, with CH$_3$CH$_2$OCOCO$_2$H in the presence of a condensing agent such as N,N-carbonyldiimidazole (ODD, N,N'-dicyclohexylcarbodiimide (DCC), 1-(3-dimethylaminopropyl)-3-ethylcarbodiimide hydrochloride (EDC), N,N'-diisopropylcarbodiimide (DIC) or 2-(1H-benzotriazole-1-yl)-1,1,3,3-tetramethyluronium tetrafluoroborate (TBTU); optionally in presence of 1-hydroxybenzotriazole hydrate (HOBT) in a solvent such as dioxane or pyridine, to give a compound of formula (XIV):

XIV wherein PG, Z and R are as defined above;
or 4a) reacting a compound of formula (XV):

XV wherein PG, Z and R are as defined above, with CH$_3$CH$_2$COOCN in a solvent such as dioxane and either 4b) reacting the resultant compound of formula (XVI):

5c) reacting the resultant compound of formula (XX):

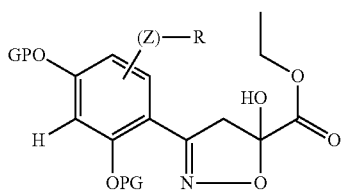

XX wherein PG, Z and R are as defined above, with an acid such as camphorsulfonic, benzensulfonic or toluensulfonic acid, in a solvent such as dioxane, toluene, xylene, at a temperature ranging from 110° C. to 150° C., to give a compound of formula (XXI):

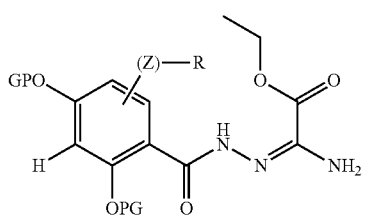

XVI wherein PG, Z and R are as defined above, with potassium tert-butoxide in solvent such as N,N-dimethylformamide (DMF) or dimethylacetamide (DMA), to give compound of formula (XVII):

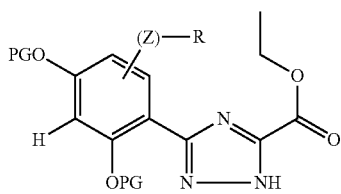

XVII

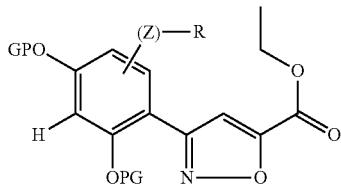

XXI wherein PG, Z and R are as defined above;
or 4b') reacting a compound of formula (VII) as defined above, with acetic anhydride and acetic acid or trifluoroacetic anhydride in a solvent such as THF or dioxane, to give a compound of formula (XVIII):

wherein PG, Z and R are as defined above;
or 6a) reacting a compound of formula (XXII):

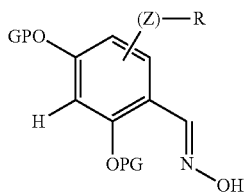

XXII

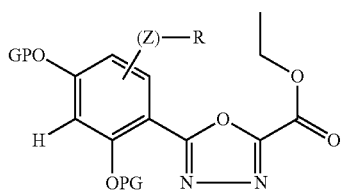

XVIII wherein PG, Z and R are as defined above;
5a) reacting a compound of formula (II) as defined above with NH$_2$OH.HCl or NH$_2$OH.H$_2$SO$_4$ in a solvent such as ethanol, THF or acetic acid, in the presence of a base such as sodium or potassium acetate;
5b) reacting the resultant compound of formula (XIX):

wherein PG, Z and R are as defined above, with ethyl propiolate or with a properly substituted propynoic acid amide in dichloromethane (DCM) in the presence an oxidant such as 5 M NaOCl solution or NBS in presence of TEA to give a compound of formula (XXI) as defined above;
either 7a) reacting any of the compounds of formula (IV), (V), (VIII), (IX), (XII), (XIV), (XVII), (XVIII) and (XXI) as defined above with an inorganic base such as NaOH, LiOH, KOH in a solvent such as ethanol, methanol, THF and 7b) reacting the resultant compound of formula (XXIII):

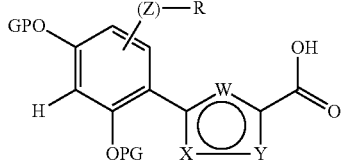

XXIII

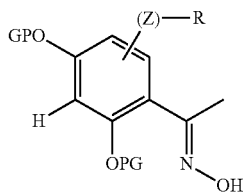

XIX wherein PG, Z and R are as defined above, with n-ButLi and (COOC$_2$H$_5$)$_2$ in a solvent such as THF at a temperature ranging from −78° C. to −35° C.;

wherein X, Y, W, PG, Z and R are as defined above, with R$_2$NH$_2$ wherein R$_2$ is defined as above, in presence of an activating agent such as DIC, TBTU, HOBT, EDC, DCC in a solvent such as THF, dioxane, DMF, DMA, so as to obtain a compound of formula (XXIV):

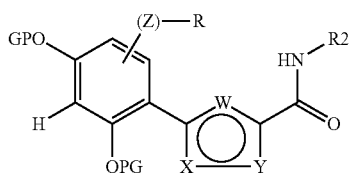

wherein X, Y, W, PG, Z, R and R$_2$ are as defined above;
or 7a') reacting a compound of formula (IV), (V), (VIII), (IX), (XII), (XIV), (XVII), (XVIII) and (XXI) as defined above with R$_2$NH$_2$ wherein R$_2$ is defined as above, in the presence of a catalyst such as potassium cyanide, pyridine-2-ol, in solvent such as ethanol, THF, dioxane, DMF, to give a compound of formula (XXIV) as defined above;
or 7b') reacting a compound of formula (XXIII) as defined above with diphenylphosphoryl azide (DPPA) in presence of TEA or DI PEA in a solvent such as dioxane, THF at reflux; 7c') reacting the resultant compound of formula (XXV):

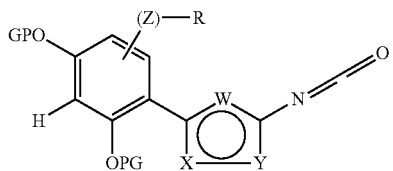

wherein X, Y, W, PG, Z and R are as defined above, with R$_2$NH$_2$ wherein R$_2$ is as defined above, in a solvent such as dioxane, THF, DMF, to give a compound of formula (XXVI):

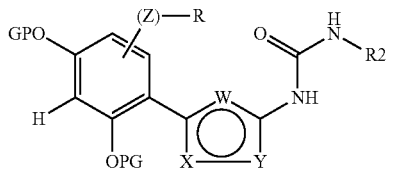

wherein X, Y, W, PG, Z, R and R$_2$ are as defined above;
or 7c'') reacting a compound of formula (XXV) as defined above, with H$_2$O, in a solvent such as dioxane, THF, DMF in presence of HCl, acetic acid, H$_2$SO$_4$ and
either 7d) reacting the resultant compound of formula (XXVII):

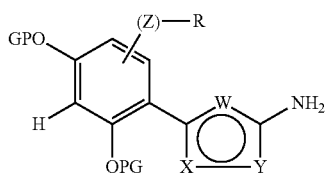

wherein X, Y, W, PG, Z and R are as defined above, with R$_2$COOH in presence of an activating agent such as CDI, TBTU, EDC, DIC, or DCC in presence of HOBT, in a solvent such as THF, DMF, DMA, or with R$_2$COCl in a solvent such as THF, pyridine, CHCl$_3$ in presence of an organic base such as triethylamine, 4-methylmorpholine, ethyldiisopropylamine to give a compound of formula (XXVIII):

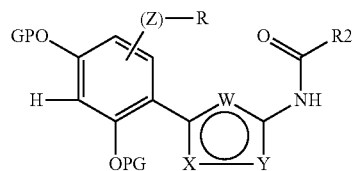

wherein X, Y, W, PG, Z, R and R$_2$ are as defined above;
or 7d') reacting a compound of formula (XXVII) as defined above, with R$_2$SO$_2$Cl, in a solvent such as THF, pyridine, CHCl$_3$ in presence of an organic base such as triethylamine, 4-methylmorpholine, ethyldiisopropylamine, to give a compound of formula (XXIX):

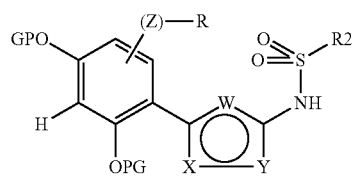

wherein X, Y, W, PG, Z, R and R$_2$ are as defined above;
8a) deprotecting any of the resultant compound of the formula (XXX):

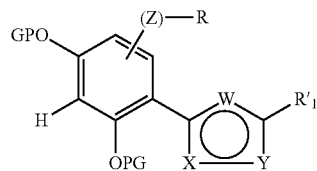

wherein Z and R are as defined above and R'$_1$ is R$_1$ or a COOC$_2$H$_5$ or COOH group, to give a compound of formula (XXXI):

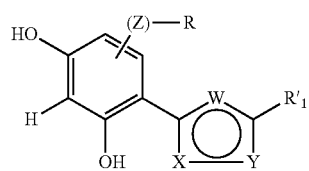

wherein X, Y, W, Z are as defined above and R'$_1$ is a COOC$_2$H$_5$ or COOH group, or to give a compound of the formula (I) as defined above, the deprotection being carried out by treatment either with H$_2$ and a suitable catalyst, in a solvent such as acetic acid, ethanol or methanol when PG is a benzyl group, or with BCl$_3$ or BBr$_3$ in a solvent such as CH$_2$Cl$_2$, CHCl$_3$, ClCH$_2$CH$_2$Cl, CH$_3$CN, when PG is a benzyl or methyl group; or
9a) reacting a compound of formula (XXX) as defined above, wherein PG is a methoxymethyl or 2-methoxyethoxymethyl group, with HCl water solution, H$_2$SO$_4$ water solution or trifluoroacetic acid water solution in a solvent such as ethanol, methanol, to give to give a compound of formula (XXXI) or a compound of formula (I) as defined above; or 10a) converting a compound of formula (XXXI) as defined above into a compound of formula (I) by known chemical reactions.

Examples of possible reactions for a conversion of step 10a above are 1) hydrolysis under acid or basic condition of a compound of formula (XXXI) wherein $R'_1$ is a $COOC_2H_5$ group for conversion into a compound of formula (XXXI) wherein $R'_1$ is a COOH, according to standard procedures as reported in The Chemistry of Carboxylic Acids and Esters, Saul Patai, Interscience Publisher (John Wiley&Sons 1969), and subsequent amidation for obtaining the corresponding amides of the formula (I), wherein $R_1$ is a $CONHR_2$ group, wherein $R_2$ is as defined above, under known conditions;

2) direct amidation of a compound of formula (XXXI) wherein $R'_1$ is a $COOC_2H_5$ group for obtaining the corresponding amides of the formula (I) wherein $R_1$ is a $CONHR_2$ group, wherein $R_2$ is as defined above, by reaction with a suitable primary amine according to standard procedures as reported in The Chemistry of Amides, Saul Patai, Interscience Publisher (John Wiley&Sons 1970).

If necessary or wanted, the process comprises converting a compound of formula (I) into a different compound of formula (I) by known chemical reactions; and/or, if desired, converting a compound of formula (I) into a pharmaceutically acceptable salt thereof or converting a salt into the free compound of formula (I).

Examples of possible reactions for such conversion are 1) reduction of amides derivatives for conversion into the corresponding amines according to standard procedures as reported in The Chemistry of Amino Group, Saul Patai, Interscience Publisher (John Wiley&Sons 1968);

2) ketalization of carbonyl derivatives for conversion into the corresponding ketales according to standard procedures as reported in The Chemistry of Carbonyl Group, Saul Patai, Interscience Publisher (John Wiley&Sons 1966).

3) alkylation or reductive alkylation of primary or secondary amines into the corresponding secondary and tertiary amines according to the standard procedure as reported in The Chemistry of Amino Group, Saul Patai, Interscience Publisher (John Wiley&Sons 1968), or J. Am. Chem. Soc., 1971, 93, 2897, or in Comprehensive Organic Synthesis, Trost B. N., Fleming L. (Eds. Pergamon Press: New York, 1991; Vol. 8).

The following useful intermediates are the esters of the formula (IV), (V), (VIII), (IX), (XII), (XIV), (XVII), (XVIII) and (XXI) as defined above, and they are also object of the present invention, with the proviso that:

5-(2,4,5-trimethoxyphenyl)-3-isoxazolecarboxylic acid, ethyl ester,

5-[5-ethyl-2,4-bis(phenylmethoxy)phenyl]-3-isoxazolecarboxylic acid, ethyl ester, 5-[5-(2-methylpropyl)-2,4-bis(phenylmethoxy)phenyl]-3-isoxazolecarboxylic acid, ethyl ester, 5-[5-(1-methylethyl)-2,4-bis(phenylmethoxy)phenyl]-3-isoxazolecarboxylic acid, ethyl ester, 5-[5-(1,1-dimethylethyl)-2,4-bis(phenylmethoxy)phenyl]-3-isoxazolecarboxylic acid, ethyl ester and 3-(2,4,6-trimethoxyphenyl)-5-isoxazolecarboxylic acid, ethyl ester are excluded.

Other useful intermediates are the acids of the formula (XXIII) as defined above, and they are also object of the present invention, with the proviso that:

3-(2,4,5-trimethoxyphenyl)-5-isoxazolecarboxylic acid, 3-(2,4,6-trimethoxyphenyl)-5-isoxazolecarboxylic acid, 2-(2,4,5-trimethoxyphenyl)-5-thiazolecarboxylic acid, 2-(2,4,6-trimethoxyphenyl)-5-thiazolecarboxylic acid, 5-(2,4,5-trimethoxyphenyl)-3-isoxazolecarboxylic acid and 5-(2,4,6-trimethoxyphenyl)-3-isoxazolecarboxylic acid are excluded.

Other useful intermediates are the amides of the formula (XXIV) as defined above, and they are also object of the present invention, with the proviso that:

N-ethyl-5-[4'-fluoro-4,6-bis(phenylmethoxy)[1,1-biphenyl]-3-yl]-3-isoxazolecarboxamide, N-ethyl-5-[2'-methyl-4,6-bis(phenylmethoxy)[1,1'-biphenyl]-3-yl]-3-isoxazolecarboxamide, N-ethyl-5-[2'-fluoro-4,6-bis(phenylmethoxy)[1,1-biphenyl]-3-yl]-3-isoxazolecarboxamide, 5-[4,6-bis(phenylmethoxy)[1,1-biphenyl]-3-yl]-N-ethyl-3-isoxazolecarboxamide, N-ethyl-5-[5-[2-(3-fluorophenyl)ethyl]-2,4-bis(phenylmethoxy)phenyl]-3-isoxazolecarboxamide, N-ethyl-5-[5-[2-(3-fluorophenyl)ethenyl]-2,4-bis(phenylmethoxy)phenyl]-3-isoxazolecarboxamide, N-ethyl-5-[5-[2-(4-fluorophenyl)ethyl]-2,4-bis(phenylmethoxy)phenyl]-3-isoxazolecarboxamide, N-ethyl-5-[5-[(1E)-2-(4-fluorophenyl)ethenyl]-2,4-bis(phenylmethoxy)phenyl]-3-isoxazolecarboxamide, N-ethyl-5-[5-ethyl-2,4-bis(phenylmethoxy)phenyl]-3-Isoxazolecarboxamide, N-ethyl-5-[5-[(1E)-2-phenylethenyl]-2,4-bis(phenyl methoxy)phenyl]-3-isoxazolecarboxamide, N-ethyl-5-[5-(2-methylpropyl)-2,4-bis(phenylmethoxy)phenyl]-3-isoxazolecarboxamide, N-ethyl-5-[5-(1-methylethyl)-2,4-bis(phenylmethoxy)phenyl]-3-isoxazolecarboxamide, 5-[5-(1,1-dimethylethyl)-2,4-bis(phenylmethoxy)phenyl]-N-ethyl-3-isoxazolecarboxamide, N-ethyl-5-[5-(2-phenylethyl)-2,4-bis(phenylmethoxy)phenyl]-3-isoxazolecarboxamide, N-ethyl-5-[5-(2-phenylethenyl)-2,4-bis(phenylmethoxy) phenyl]-3-isoxazolecarboxamide and N-[5,6,7,8-tetrahydro-6-(1-piperidinylmethyl)-2-naphthalenyl]-3-(2,4,5-triethoxyphenyl)-5-isoxazolecarboxamide are excluded.

Other useful intermediates are the compounds of the formula (XXXI) as defined above, and they are also object of the present invention, with the proviso that: 1H-pyrazole-3-carboxylic acid, 5-[5-[5-(hydrazinylcarbonyl)-1H-pyrazol-3-yl]-2,4-dihydroxyphenyl]-, ethyl ester and 1H-pyrazole-3-carboxylic acid, 5,5'-(4,6-dihydroxy-1,3-phenylene)bis-, diethyl ester are excluded.

Specifically, the present invention provides the following intermediate compounds: 5-[2,4-dihydroxy-6-(4-nitrophenoxy)phenyl]isoxazole-3-carboxylic acid and methyl 5-[2,4-dihydroxy-6-(4-nitrophenoxy)phenyl]isoxazole-3-carboxylate.

The synthesis of a compound of formula (I), according to the synthetic process described above, can be conducted in a stepwise manner, whereby each intermediate is isolated and purified by standard purification techniques, like, for example, column chromatography, before carrying out the subsequent reaction. Alternatively, two or more steps of the synthetic sequence can be carried out in a so-called "one-pot" procedure, as known in the art, whereby only the compound resulting from the two or more steps is isolated and purified.

According to any variant of the process for preparing the compounds of formula (I), the starting materials and any other reactants are known or easily prepared according to known methods. As an example, compounds of formula (II), (VI), (X), (XV) and (XXII) are commercially available or can be prepared according to well known chemical synthesis, as for example described in the following examples.

Pharmacology

The potencies of the compounds of the present invention were evaluated by measuring the Her2 degradation as a marker for HSP90 inhibition.

HSP90 is a key component of a chaperone machinery that catalyzes the folding and quality control of several proteins. Its inhibition impairs the capacity to fold or stabilize its client proteins, leading to the proteosomal dependent degradation of these unfolded proteins. At the moment there is an increasing number (>100) of reported HSP90 clients, but one of the most frequently way to detect HSP90 chaperone inhibition is the detection of Her2 protein levels after short time treatment (usually 8-24 h), in order to be sure about the specificity of this effect. Cellular activity of HSP90 inhibitors was assessed by measuring the induced loss of Her2 protein levels in BT474 breast cancer cells (ATCC #HTB-20). Cellular Her2 levels were measured by immunocytochemistry, and quantified using an ArrayScan vTi instrument (Cellomics Thermo Scientific).

Her2 Degradation Assay

Cellular activity of HSP90 inhibitors was assessed by measuring the induced loss of Her2 protein levels in BT474 breast cancer cells (ATCC #HTB-20). Cellular Her2 levels were measured by immunocytochemistry, and quantified using an ArrayScan vTi instrument (Cellomics Thermo Scientific).

Studies were performed as follows: 5000 cells/well are seeded in 96 well plates (Perkin Elmer) in DMEM/5% FCS and incubated for 48 hours at 37° C., 5% $CO_2$.

Medium is then replaced with fresh medium containing test compounds at the required concentration. Concentration curves are prepared in DMEM/10% FCS from compound stocks in DMSO, and final DMSO concentration is 0.1% (v/v). Duplicate wells for each concentration point are prepared, with a typical highest compound concentration of 30 µM. After addition of compound, plates are returned to the incubator for 8 hours, then fixed by replacing medium with PBS containing 3.7% paraformaldehyde solution. Plates are incubated for 20 minutes at room temperature, then wells are washed in PBS and cells permiabilised by incubating with PBS containing 0.3% Triton X-100 for 15 minutes at room temperature. Non-specific binding sites are blocked by incubating wells for 1 hour in PBS containing 3% (w/v) BSA. Wells are then incubated for 1 hour at room temperature in PBS containing anti Her2 mouse monoclonal (Anti-c-ErbB2/c-Neu, Mouse mAb 3B5, Calbiochem Cat N° OP15) diluted 1:100 in 1% (w/v) BSA. After 3 washes in PBS, wells are incubated in PBS (w/v) 1% BSA containing a 2 µg/ml of Cy2-conjugated Goat anti mouse secondary antibody (Amersham Pharmacia Biotech cat. N° PA 42002) (Absorption maximum 489 nm fluorescence maximum 506 nm) and 1 µg/ml of DAPI (Absorption maximum 359 nm fluorescence maximum 461 nm) (4',6-Diamidine-2-phenylindole, dilactate) (Sigma cat. N° D 9564) a high sensitivity dye to detect nucleid acid for nuclear staining. After washing a further 3 times in PBS, cellular Her2 immunoreactivity is assessed using the ArrayScan vTi instrument, with a Zeiss 10× 0.5 N.A. objective, and applying the Cytotoxity.V3 algorithm (Cellomics/Thermo Fisher) with a XF100 filter. At least 10 fields, corresponding to at least 900 cells, are read for each well. $IC_{50}$ values represent the compound concentration at which cellular Her2 signal is diminished by 50% compared with untreated controls.

The following formula is used:

$IC_{50}$=Bottom+(Top−Bottom)/(1+10^((Log $EC_{50}$−$X$));
$X$ is the logarithm of concentration. $IC_{50}$ is the response; $IC_{50}$ starts at Bottom and goes to Top with a sigmoid shape.

In Vitro Cell Proliferation Assay

A2780 human ovarian cells (1250 cells/well) were seeded in white 384 well-plates in complete medium (RPMI1640 or EMEM plus 10% Fetal bovine serum) and treated with compounds dissolved in 0.1% DMSO, 24 h after seeding. The cells were incubated at 37° C. and 5% $CO_2$ and after 72 hours the plates were processed using CellTiter-Glo assay (Promega) following the manufacturer's instruction.

CellTiter-Glo is a homogenous method based on the quantification of the ATP present, an indicator of metabolically active cells. ATP is quantified using a system based on luciferase and D-luciferin resulting into light generation. The luminescent signal is proportional to the number of cells present in culture.

Briefly 25 µL/well reagent solution are added to each wells and after 5 minutes shacking microplates are red by a luminometer. The luminescent signal is proportional to the number of cells present in culture.

Determination of $K_D$ Via Biacore

The evaluation of the binding affinity ($K_D$) of the compounds of formula (I) to the HSP90 protein was done using Biacore T100.

His-HSP90 N-term domain was immobilized by capture of his tag by the Ab previously covalently bound to the chip (CM5) surface. A short cross-linking procedure after HSP90 binding was necessary in order to obtained a more stable signal.

The compounds were analyzed using the following running buffer: 20 mM Tris/HCl pH 7.6, 150 mM KCl, 5 mM $MgCl_2$, 0.05% P20 and 1% DMSO. The flow rate was 50 ul/min with and association time of 60 seconds.

The cpds were diluted in running buffer from 100× stock solution; the different conc injected were obtained from a sequential dilution in order to have the same DMSO conc. in each sample and avoid any solvent correction.

A series of 5 sequential injections of increasing concentrations of compound were performed and the results were analyzed using a method reported in literature (Robert Karlsson et al "Analyzing a kinetic titration series using affinity biosensors". (Analytical Biochemistry 349 (2006) 136-147). Each analysis were performed twice, showing a very high reproducibility of the results.

Given the above assays, the compounds of formula (I) result to possess a remarkable HSP90 inhibitory activity, as proven by the induction of the Her2 protein degradation, cell proliferation inhibitory activity (A2780 cell line) and high binding affinity at the protein, as shown in the following Table 1.

TABLE 1

| Compound | Her2 Degradation $IC_{50}$ (µM) | A2780 Proliferation $IC_{50}$ (µM) | Kd (nM) Biacore |
|---|---|---|---|
| 5-[2,4-Dihydroxy-6-(4-nitrophenoxy)phenyl]-N-ethylisoxazole-3-carboxamide | 0.059 | 0.07 | 0.8 |

TABLE 1-continued

| Compound | Her2 Degradation IC$_{50}$ (µM) | A2780 Proliferation IC$_{50}$ (µM) | Kd (nM) Biacore |
|---|---|---|---|
| 5-[2-(4-Chlorophenoxy)-4,6-dihydroxyphenyl]-N-ethylisoxazole-3-carboxamide | 0.059 | 0.304 | 9.2 |
| 5-[2,4-Dihydroxy-6-(4-nitrophenoxy)phenyl]-N-[1-(propan-2-yl)piperidin-4-yl]isoxazole-3-carboxamide | 0.058 | 0.05 | 3.2 |
| 5-[2,4-Dihydroxy-6-(4-nitrophenoxy)phenyl]-N-[1-(4,4,4-trifluorobutyl)piperidin-4-yl]isoxazole-3-carboxamide | 0.071 | 0.06 | |
| N-(1-Cyclohexylpiperidin-4-yl)-5-[2,4-dihydroxy-6-(4-nitrophenoxy)phenyl]isoxazole-3-carboxamide | 0.071 | 0.04 | 0.3 |
| 5-{2-[4-(Dimethylamino)phenoxy]-4,6-dihydroxyphenyl}-N-(1-methylpiperidin-4-yl)isoxazole-3-carboxamide | 0.039 | 0.03 | 0.12 |
| 5-[2-(4-Cyanophenoxy)-4,6-dihydroxyphenyl]-N-ethylisoxazole-3-carboxamide | 0.277 | 0.147 | |
| N-[1-(4,4-Difluorocyclohexyl)piperidin-4-yl]-5-[2,4-dihydroxy-6-(4-nitrophenoxy)phenyl]isoxazole-3-carboxamide | 0.027 | 0.05 | 0.8 |
| 5-[2,4-Dihydroxy-6-(4-nitrophenoxy)phenyl]-N-(1-methylpiperidin-4-yl)isoxazole-3-carboxamide | 0.11 | 0.06 | 0.35 |
| 5-{2-[4-(Dimethylamino)phenoxy]-4,6-dihydroxyphenyl}-N-[1-(1,4-dioxaspiro[4.5]dec-8-yl)piperidin-4-yl]isoxazole-3-carboxamide | 0.012 | 0.02 | 0.057 |
| 3-{2-[4-(Dimethylamino)phenoxy]-4,6-dihydroxyphenyl}-N-[1-(1,4-dioxaspiro[4.5]dec-8-yl)piperidin-4-yl]isoxazole-5-carboxamide | 0.003 | 0.020 | 0.043 |
| 3-{2-[4-(Dimethylamino)phenoxy]-4,6-dihydroxyphenyl}-N-(1-methylpiperidin-4-yl)isoxazole-5-carboxamide | 0.008 | 0.03 | 0.066 |
| 5-(2,4-Dihydroxy-6-{4-[(1-methylethyl)amino]phenoxy}phenyl)-N-(1-methylpiperidin-4-yl)isoxazole-3-carboxamide | 0.065 | 0.020 | 0.218 |
| 5-{2-[4-(Dimethylamino)phenoxy]-4,6-dihydroxyphenyl}-N-[1-(3,3-dimethyl-1,5-dioxaspiro[5.5]undec-9-yl)piperidin-4-yl]isoxazole-3-carboxamide | 0.037 | 0.035 | 0.080 |
| 5-{2-[4-(Dimethylamino)phenoxy]-4,6-dihydroxyphenyl}-N-[1-(7,12-dioxaspiro[5.6]dodec-3-yl)piperidin-4-yl]isoxazole-3-carboxamide | 0.045 | 0.023 | 0.423 |
| 5-{2-[4-(Dimethylamino)phenoxy]-4,6-dihydroxyphenyl}-N-[1-(1,5-dioxaspiro[5.5]undec-9-yl)piperidin-4-yl]isoxazole-3-carboxamide | 0.038 | 0.021 | 0.079 |
| N-[1-(Cyclohexylmethyl)piperidin-4-yl]-5-{2-[4-(dimethylamino)phenoxy]-4,6-dihydroxyphenyl}isoxazole-3-carboxamide | 0.020 | 0.010 | 0.188 |
| N-[1-(4,4-Difluorocyclohexyl)piperidin-4-yl]-5-{2-[4-(dimethylamino)phenoxy]-4,6-dihydroxyphenyl}isoxazole-3-carboxamide | 0.002 | 0.020 | 0.057 |
| 3-[2,4-Dihydroxy-6-(4-nitrophenoxy)phenyl]-N-(1-methylpiperidin-4-yl)isoxazole-5-carboxamide | 0.022 | 0.020 | 0.24 |
| N-(1-Cyclohexylpiperidin-4-y)-5-{2-[4-(dimethylamino)phenoxy]-4,6-dihydroxyphenyl}isoxazole-3-carboxamide | 0.003 | 0.020 | 0.09 |

In Vivo Antitumor Efficacy

Antitumor activity of HSP90 inhibitors was assessed in vivo using the human ovarian carcinoma cell line A2780 transplanted in immunodeficient mice. This tumor model was selected based on the demonstrated sensitivity in cell based assay to HSP90 inhibitors.

Study were performed as follow:

Balb Nu/Nu, male mice, (athymic mice) from Harlan, Italy, were maintained in cages with paper filter covers, food and bedding sterilized and water acidified. A2780 tumors were maintained in vivo by serial transplantation and, at the time of efficacy experiments, implanted subcutaneously in athymic mice. The treatments started 8 days later when the tumors were palpable. HSP90 inhibitors were prepared immediately before use and administered intravenously in a volume of 10 ml/kg at different doses.

Tumor growth was assessed by caliper. The two diameters were recorded, and the tumor weight was calculated according to the following formula: length (mm)×width$^2$ (mm)/2. The effect of the antitumor treatment was determined as tumor growth inhibition (TGI %) of treated group respect to vehicle treated controls.

The compound 5-[2,4-dihydroxy-6-(4-nitrophenoxy)phenyl]-N-(1-methylpiperidin-4-yl)isoxazole-3-carboxamide, was administered at 30 and 60 mg/kg for 10 consecutive days. Every 3 days the tumor growth and the net body weight were evaluated. Said compound showed a significant antitumor activity with a TGI of 74% at 60 mg/kg and 53% at 30 mg/kg, without signs of toxicities.

In the same model other compounds showed significant antitumour activity: e.g.: 5-{2-[4-(dimethylamino)phenoxy]-4,6-dihydroxyphenyl}-N-[1-(1,5-dioxaspiro[5.5]undec-9-yl)piperidin-4-yl]isoxazole-3-carboxamide and 5-{2-[4-(dimethylamino)phenoxy]-4,6-dihydroxyphenyl}-N-(1-methylpiperidin-4-yl)isoxazole-3-carboxamide, showed a TGI of 92% and 77% respectively when given intravenously at 30 and 40 mg/Kg daily, while 3-{2-[4-(dimethylamino)phenoxy]-4,6-dihydroxyphenyl}-N-(1-methylpiperidin-4-yl)isoxazole-5-carboxamide showed an antitumor activity measured as 88% TGI when administered intravenously at 40 mkg/kg every three days.

In Vivo Pharmacokinetic Evaluation

The pharmacokinetic profile of the compounds of the present invention was investigated as reported in Table 2.

Elution conditions:

| Time (min) | 0.00 | 0.80 | 1.00 | 1.01 | 2.00 |
|---|---|---|---|---|---|
| % A | 80 | 0 | 0 | 80 | 80 |
| % B | 20 | 100 | 100 | 20 | 20 |

Total Run Time: 2.0 min.
Flow rate: 0.500 mL/min
Approximate retention time: NMS-03308086: 0.67 min.
Column oven temp: 40° C.
Autosampler type: Waters Acquity SM
Injection volume: 3 µL
Injection mode: Partial Loop with Needle Overfill
Autosampler temperature: 5° C.
MS instrument: Waters TQD
Ionisation: ES+

TABLE 2

| | |
|---|---|
| Formulations | IV: 10% Tween 80 in 5% Dextrose |
| | OS: 0.5% Methocel |
| Species, Strain, & Source | Mouse, Balb, Nu/Nu, Harlan, Italy |
| No. of Animals/Gender | 3/M route. Total: 6 |
| Dosage, Route & Frequency | 10 mg/kg, IV Bolus, Single |
| | 10 mg/kg, Oral, Single |
| Specimen Collection Schedule (Blood/plasma) | IV: 0.083, 0.5; 1, 3, 6, 24 h post-dosing; |
| | OS: 0.25, 0.5, 1, 3, 6, 24 h post-dosing; |
| | All blood samples were taken from retro-orbital vein. |
| Analyses and experimental details | Bioanalysis: LC/MS/MS on Waters Acquity-TQD system. |
| | Pharmacokinetics: analysis by WinNonlin software 5.2.1. |
| | Non-compartmental method (linear trapezoidal rule and linear regression analysis of natural log-transformed plasma concentrations vs. time data) was used. |

Bioanalytical Conditions
Standard and Sample Preparation

Calibration Standards and Quality Controls were prepared spiking blank mouse plasma with appropriate working solutions.

Sample plasma proteins were precipitated by adding 160 µL of acetonitrile/methanol 90/10 to 20 µL of mouse plasma in a 96 well plate.

After heat sealing and mixing for 3 minutes, the plate was centrifuged for 15 minutes at 4000 rpm.

The supernatant was considered as final extract and injected onto the LC-MS-MS system.

LC/MS/MS Parameters
  UPLC system: Waters Acquity BSM
  Mobile phase A: 95:5-5 mM Ammonium Formate pH3.5: Acetonitrile
  Mobile phase B: 5:95-5 mM Ammonium Formate pH3.5: Acetonitrile
  Analytical column: BEH C18 50×2.1 1.7 µm
  Capillary: 1.5 kV
  Cone: 70 V
  Source Temperature: 150° C.
  Desolvation Flow and Temp.: 900 L/h-400° C.
  Collision Gas Flow: 0.2 mL/min
  Collision Energy: 40
  MRM transitions: NMS-03308086: m/z 579.1>m/z 97.0
  Dwell Time: 0.1 seconds
  LLOQ: 5.0 ng/mL
  ULOQ: 5000 ng/mL
  Software used: Mass Lynx 4.1 SCN627

Table 3 below illustrates the results of the most significant pharmacokinetic parameters of compounds of the present invention. As shown in Table 3 below representative compounds of the present invention possess a remarkable pharmacokinetic profile as demonstrated by high Terminal half-life, high distribution volume, low clearance and a significative oral bioavailability (F %).

TABLE 3

| Compound Name | $T_{1/2}$ (h) | Vdss (mL/kg) | CL (mL/h/kg) | F % |
|---|---|---|---|---|
| 3-[2,4-Dihydroxy-6-(4-nitrophenoxy)phenyl]-N-(1-methylpiperidin-4-yl)isoxazole-5-carboxamide | 1.52 | 4471 | 3419 | 7 |
| 3-{2-[4-(Dimethylamino)phenoxy]-4,6-dihydroxyphenyl}-N-(1-methylpiperidin-4-yl)isoxazole-5-carboxamide | 5.12 | 12522 | 3434 | 25 |
| 3-{2-[4-(Dimethylamino)phenoxy]-4,6-dihydroxyphenyl}-N-[1-(1,4-dioxaspiro[4.5]dec-8-yl)piperidin-4-yl]isoxazole-5-carboxamide | 7.23 | 9121 | 1912 | 23 |

TABLE 3-continued

| Compound Name | $T_{1/2}$ (h) | Vdss (mL/kg) | CL (mL/h/kg) | F % |
|---|---|---|---|---|
| N-(1-Cyclohexylpiperidin-4-yl)-5-{2-[4-(dimethylamino)phenoxy]-4,6-dihydroxyphenyl}isoxazole-3-carboxamide - 1,3-dioxolane | 5.46 | 4944 | 1761 | 36 |
| 5-{2-[4-(Dimethylamino)phenoxy]-4,6-dihydroxyphenyl}-N-[1-(3,3-dimethyl-1,5-dioxaspiro[5.5]undec-9-yl)piperidin-4-yl]isoxazole-3-carboxamide | 6.71 | 5995 | 1340 | 19 |
| 5-{2-[4-(Dimethylamino)phenoxy]-4,6-dihydroxyphenyl}-N-[1-(7,12-dioxaspiro[5.6]dodec-3-yl)piperidin-4-yl]isoxazole-3-carboxamide | 6.87 | 5981 | 1312 | 14 |

Abbreviations used the Table 3:
$T_{1/2}$ (IV) = Terminal half-life,
Vdss = Volume of distribution at steady state,
CL = Plasma clearance,
F = Oral bioavailability The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrix metalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range. Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride. The solutions for intravenous injections or infusions may contain, as a carrier, sterile water or preferably they may be in the form of sterile, aqueous, isotonic, saline solutions or they may contain propylene glycol as a carrier. The suppositories may contain, together with the active compound, a pharmaceutically acceptable carrier, e.g., cocoa butter, polyethylene glycol, a polyoxyethylene sorbitan fatty acid ester surfactant or lecithin.

The following examples illustrate the syntheses of the compounds of the present invention:

EXAMPLE 1

5-[2,4-Dihydroxy-6-(4-nitrophenoxy)phenyl]-N-ethyl isoxazole-3-carboxamide

[(I); (Z)—R=4-Nitrophenoxy X=O, Y=N, W=CH, $R_1=C_3H_6NO$]

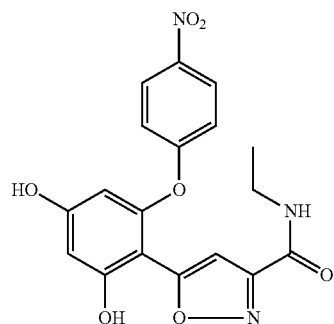 [SMILES: CCNC(=O)c1cc(-c2c(O)cc(O)cc2Oc2ccc([N+](=O)[O-])cc2)on1]

Step 1

1-[2,4-Bis(benzyloxy)-6-(4-nitrophenoxy)phenyl]ethanone

A stirred suspension of 1-[2,4-bis(benzyloxy)-6-hydroxyphenyl]ethanone (Bulletin of the Chemical Society of Japan (1985), 58(1), 136-41) (5.2 g, 15 mmol), potassium carbonate (3.1 g, 22 mmol) and 1-fluoro-4-nitrobenzene (2.1 g, 15 mmol) in DMF (10 mL) was heated at 110° C. for 2 hours. The reaction mixture was diluted with ethyl acetate (100 mL) and thoroughly washed with brine (4×50 mL). The organic phase was dried over $Na_2SO_4$ and then evaporated to dryness. The crude was chromatographed on a small pad of silica gel eluting with hexane/ethyl acetate 5/1, to provide the title compound (5 g, 73% yield).

$^1$H NMR (400 MHz, DMSO-$d_6$) δ ppm 2.33 (s, 3H) 3.84 (m, 2H) 5.11 (s, 2H) 5.22 (s, 2H) 6.46 (bs, 1H) 7.07 (bs, 2H) 6.83 (bs, 1H) 7.38 (m, 10H) 8.83 (bs, 1H).

Scheme

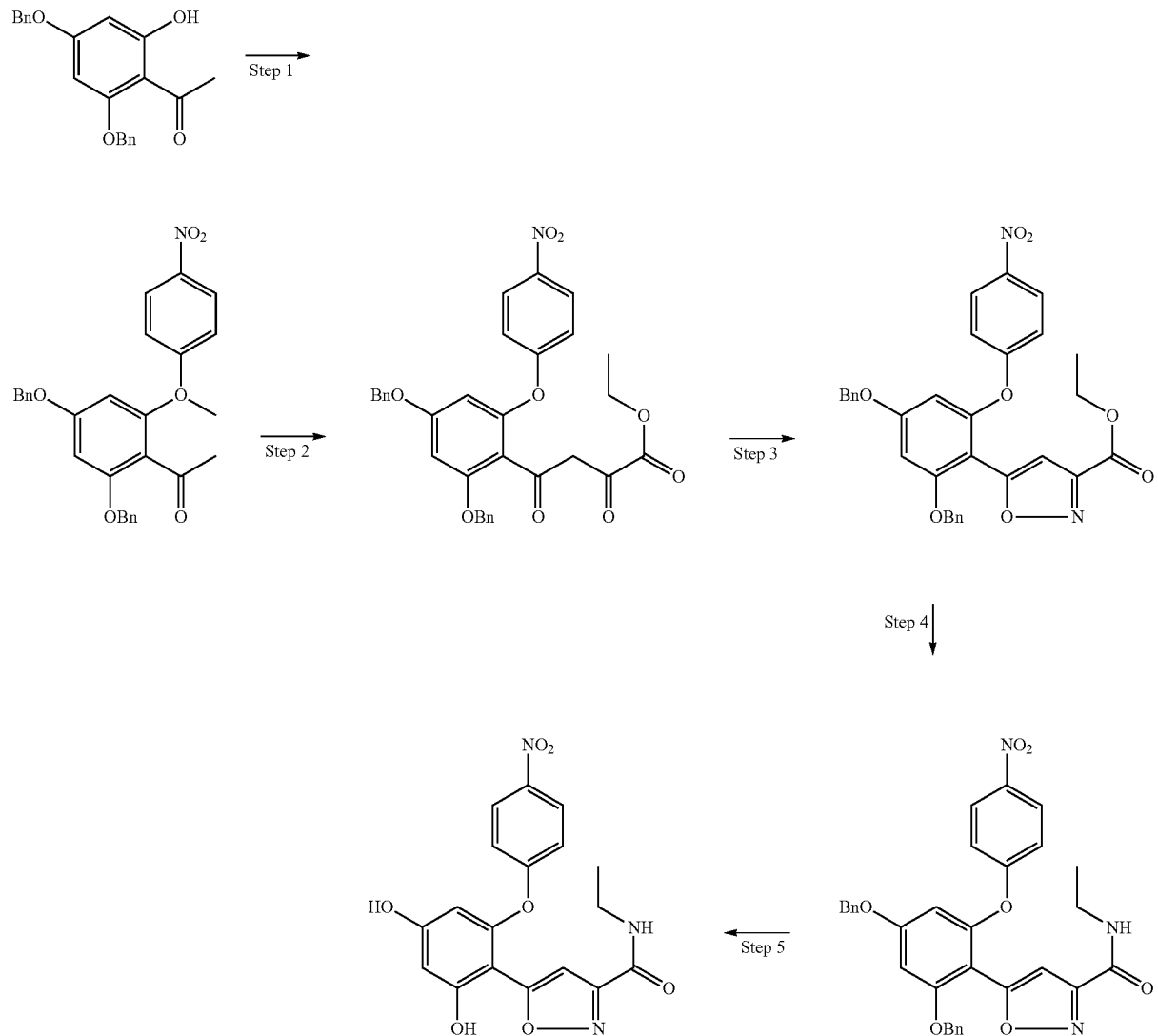

Step 2

Ethyl 4-[2,4-bis(benzyloxy)-6-(4-nitrophenoxy)phenyl]-2,4-dioxobutanoate

To a stirred solution of 1-[2,4-bis(benzyloxy)-6-(4-nitrophenoxy)phenyl]ethanone (5.1 g, 11 mmol) in THF (50 mL) was added drop wise 1M lithium (bis trimethylsilylamide/THF solution (12 mL, 12 mmol) at −50° C. After 30 minutes, a solution of diethyl oxalate (1.7 mL) in THF (15 mL) was slowly added and the stirring was continued for 1 hours. The solution was taken up in brine (200 mL) and treated with 1 M HCl solution (13 mL), then extracted with ethyl acetate. The organic phase was dried and the solvent removed. The crude was filtered on a small pad of silica gel eluting with hexane/ethyl acetate 2/1 to afford the title compound (5.7 g, 75% yield).

$^1$H NMR (400 MHz, DMSO-$d_6$) δ ppm 1.13 (t, 3H) 3.81 (q, 2H) 4.17 (bs, 1H) 5.11 (s, 2H) 5.19 (s, 2H) 6.48 (bs, 1H) 7.12 (bs, 2H) 6.87 (bs, 1H) 7.43 (m, 10H) 8.87 (bs, 1H).

Step 3

Ethyl 5-[2,4-bis(benzyloxy)-6-(4-nitrophenoxy)phenyl]isoxazole-3-carboxylate

A stirred solution of ethyl 4-[2,4-bis(benzyloxy)-6-(4-nitrophenoxy)phenyl]-2,4-dioxobutanoate (5 g, 9 mmol) and hydroxylamine hydrochloride (0.74 g, 15 mmol, 1.2 eq) in ethanol (mL 50) was refluxed for 2 hours. The solution was concentrated to a small volume and diluted with ethyl acetate. After washing with brine and drying, the solvent was removed and the residue was carefully chromatographed on silica gel eluting with hexane/ethyl acetate 6/1, to provide the title compound (4.1 g, 82% yield).

$^1$H NMR (400 MHz, DMSO-$d_6$) δ ppm 1.13 (t, 3H) 3.9 (q, 2H) 4.17 (bs, 1H) 5.10 (s, 2H) 5.25 (s, 2H) 6.45 (bs, 1H) 7.16 (bs, 2H) 6.81 (bs, 1H) 7.43 (m, 10H) 8.9 (bs, 1H).

Step 4

5-[2,4-Bis(benzyloxy)-6-(4-nitrophenoxy)phenyl]-N-ethylisoxazole-3-carboxamide

A solution of ethyl 5-[2,4-bis(benzyloxy)-6-(4-nitrophenoxy)phenyl]isoxazole-3-carboxylate (1.8 g, 3.2 mmol) in 2 M ethylamine/THF solution (100 mL) in a stopped flask was heated at 100° C. for 5 hours. The solvent was removed and the residue was crystallized from a small volume of methanol to provide the title compound (1.45 g, 83% yield).

$^1$H NMR (400 MHz, DMSO-$d_6$) δ ppm 1.06 (t, 3H) 3.3 (q, 2H) 4.19 (bs, 1H) 5.10 (s, 2H) 5.26 (s, 2H) 6.35 (bs, 1H) 7.13 (bs, 2H) 6.84 (bs, 1H) 7.47 (m, 10H) 8.7 (bs, 1H).

Step 5

5-[2,4-Dihydroxy-6-(4-nitrophenoxy)phenyl]-N-ethyl isoxazole-3-carboxamide

[(I); (Z)—R=4-Nitrophenoxy, X=O, Y=N, W=CH, $R_1=C_3H_6NO$]

To a stirred solution of 5-[2,4-bis(benzyloxy)-6-(4-nitrophenoxy)phenyl]-N-ethylisoxazole-3-carboxamide (2.5 g, 4.5 mmol) in DCM (50 mL) was slowly added 1 M BCl$_3$/DCM solution (13.2 mL, 13 mmol, 3 eq) at 0° C. After stirring for 5 hours at room temperature, the cloudy solution was diluted with DCM and thoroughly washed with water, then with 1 M NaHCO$_3$ solution and dried. The solvent was removed and the residue was columned on silica gel eluting with hexane/ethyl acetate 2/3, to provide the title compound (1.3 g, 76% yield).

$^1$H NMR (400 MHz, DMSO-$d_6$) δ ppm 1.12 (t, 3H) 3.22 (m, 2H) 6.10 (bs, 1H) 6.46 (bs, 1H) 7.79 (bs, 1H) 7.10 (bs, 2H) 8.21 (bs, 2H) 8.7 (bs, 1H) 10.70 (bs, 1H) 10.28 (bs, 1H).

EXAMPLE 2

5-[2,4-Dihydroxy-6-(4-nitrophenoxy)phenyl]-N-(2-hydroxyethyl)isoxazole-3-carboxamide

[(I); (Z)—R=4-Nitrophenoxy, X=O, Y=N, W=CH, $R_1=C_3H_6NO_2$]

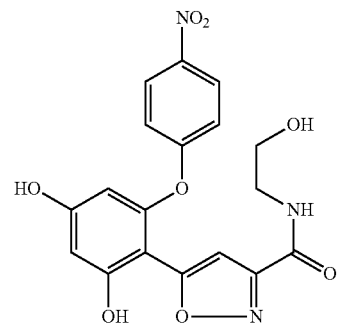 [SMILES: O=C(NCCO)c1cc(-c2c(O)cc(O)cc2Oc2ccc([N+](=O)[O-])cc2)on1]

Scheme

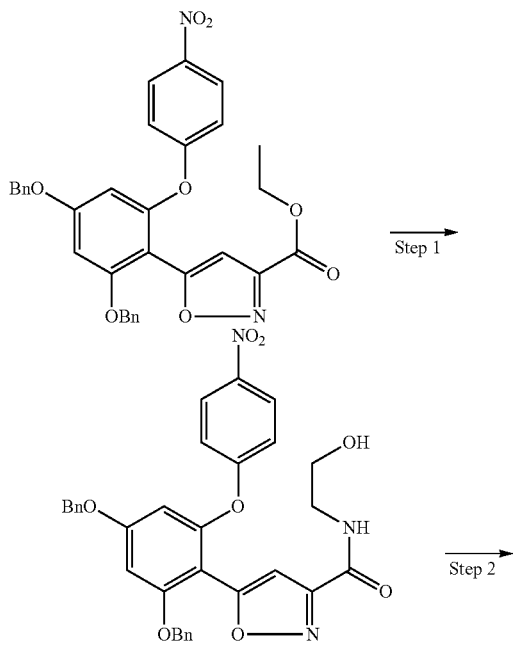

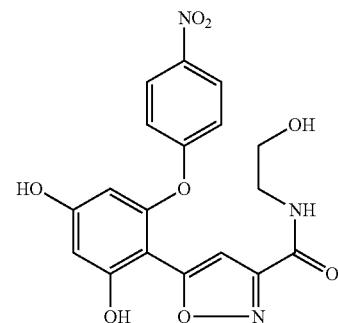

Step 1

5-[2,4-Bis(benzyloxy)-6-(4-nitrophenoxy)phenyl]-N-(2-hydroxyethyl)isoxazole-3-carboxamide Operating as in Example 1 Step 4, but employing ethanolamine instead of ethylamine, 5-[2,4-bis(benzyloxy)-6-(4-nitrophenoxy)phenyl]-N-(2-hydroxyethyl)isoxazole-3-carboxamide was prepared in 75% yield.

Step 2

5-[2,4-Dihydroxy-6-(4-nitrophenoxy)phenyl]-N-(2-hydroxyethyl)isoxazole-3-carboxamide

[(I); (Z)—R=4-Nitrophenoxy, X=O, Y=N, W=CH, $R_1=C_3H_6NO_2$]

Operating as in Example 1 Step 5, but employing 5-[2,4-bis(benzyloxy)-6-(4-nitrophenoxy)phenyl]-N-(2-hydroxyethyl)isoxazole-3-carboxamide instead of 5-[2,4-bis(benzyloxy)-6-(4-nitrophenoxy)phenyl]-N-ethylisoxazole-3-carboxamide, the title compound was obtained in 57% yield.

EXAMPLE 3

5-[2,4-Dihydroxy-6-(4-nitrophenoxy)phenyl]-N-(2-fluoroethyl)isoxazole-3-carboxamide

[(I); (Z)—R=4-Nitrophenoxy, X=O, Y=N, W=CH, $R_1=C_3H_5FNO$]

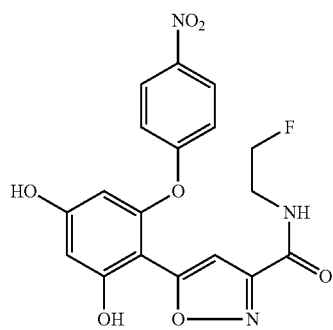

Scheme

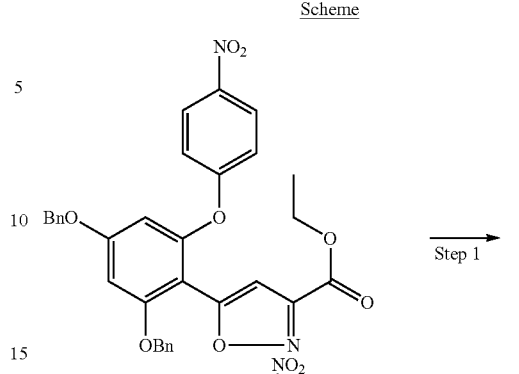

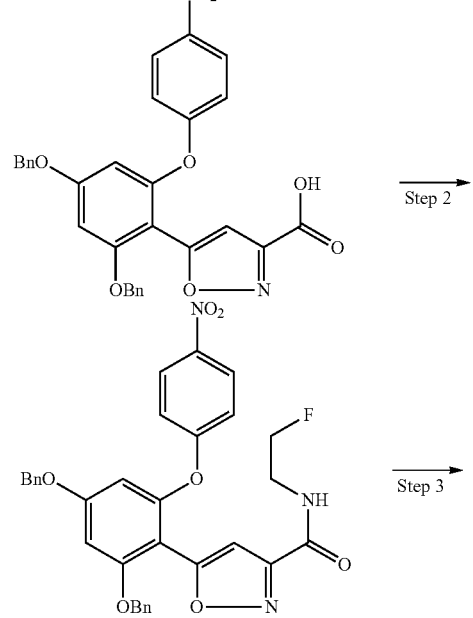

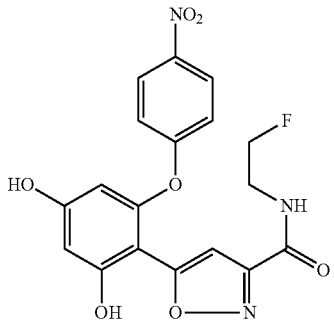 [SMILES: O=C(NCCF)c1cc(-c2c(O)cc(O)cc2Oc2ccc([N+](=O)[O-])cc2)on1]

Step 1

5-[2,4-Bis(benzyloxy)-6-(4-nitrophenoxy)phenyl]isoxazole-3-carboxylic acid

To a stirred solution of ethyl 5-[2,4-bis(benzyloxy)-6-(4-nitrophenoxy)phenyl]isoxazole-3-carboxylate (5 g, 9 mmol) in ethanol (150 mL) was added 1.5 M KOH solution (9 mL, 13.5 mmol, 1.5 eq). After stirring for 3 hours at room temperature, 2 M HCl solution (7.5 mL) was added and the suspension taken up in ethyl acetate was washed with brine. After drying and removal of the solvent, the residue was rinsed with a small volume of acetone and filtered off, to give after drying, the title compound (4.1 g, 86% yield).

$^1$H NMR (400 MHz, DMSO-$d_6$) δ ppm 4.19 (bs, 1H) 5.12 (s, 2H) 5.27 (s, 2H) 6.5 (bs, 1H) 6.87 (bs, 1H) 7.18 (bs, 2H) 7.78-7.37 (m, 10H) 8.65 (bs, 1H).

Step 2

5-[2,4-Bis(benzyloxy)-6-(4-nitrophenoxy)phenyl]-N-(2-fluoroethyl)isoxazole-3-carboxamide To a stirred solution of 5-[2,4-bis(benzyloxy)-6-(4-nitrophenoxy)phenyl]isoxazole-3-carboxylic acid (0.45 g, 0.84 mmol) in THF (30 mL) was added TBTU (0.300 g, 1.1 mmol). After stirring for 15 minutes at room temperature, 2-fluoroethylamine hydrochloride (0.1 g, 1 mmol) and DIPEA (0.58 mL) were subsequently added. After stirring overnight, the suspension was diluted with DCM and washed with brine, dried over $Na_2SO_4$ and evaporated to dryness. The residue was carefully chromatographed on silica gel eluting with hexane/ethyl acetate 3/1, to provide the title compound (0.46 g, 94% yield).

$^1$H NMR (400 MHz, DMSO-$d_6$) δ ppm 3.48 (m, 2H) 4.48 (bs, 2H) 5.13 (s, 2H) 5.22 (s, 2H) 6.31 (bs, 1H) 7.15 (bs, 2H) 6.84 (bs, 1H) 7.35-7.46 (m, 10H) 8.2 (bs, 1H) 8.24 (bs, 1H) 8.83 (bs, 1H).

Step 3

5-[2,4-Dihydroxy-6-(4-nitrophenoxy)phenyl]-N-(2-fluoroethyl)isoxazole-3-carboxamide

[(I); (Z)—R=4-Nitrophenoxy, X=O, Y=N, W=CH, $R_1$=$C_3H_6FNO$]

To a stirred solution of 5-[2,4-bis(benzyloxy)-6-(4-nitrophenoxy)phenyl]-N-(2-fluoroethyl)isoxazole-3-carboxamide (0.5 g, 0.9 mmol) in DCM (30 mL) was added 1 M $BCl_3$/DCM (3 mL) solution at 0° C. After stirring for 2 hours at room temperature, the solution was washed with 1 M $NaHCO_3$ solution, then with brine and dried. The solvent was removed and the residue was carefully chromatographed on silica gel eluting with DCM/MeOH 95/5, to afford the title compound (0.067 g, 18% yield).

$^1$H NMR (400 MHz, DMSO-$d_6$) δ ppm 3.52 (m, 2H) 4.48 (m, 2H) 6.09 (bs, 1H) 6.46 (bs, 1H) 6.83 (s, 1H) 7.10 (bs, 1H) 7.10 (bs, 1H) 8.22 (bs, 1H) 8.22 (bs, 1H) 10.31 (s, 1H) 10.72 (s, 1H).

Preparation of Ethyl 5-[2,4-dihydroxy-6-(4-nitrophenoxy)phenyl]isoxazole-3-carboxylate, via PG=2-methoxyethoxy)methyl (MEM);

[(XXXI), (Z)—R=4-Nitrophenoxy, X=O, Y=N, W=CH, $R'_1$=$CO_2C_2H_5$]

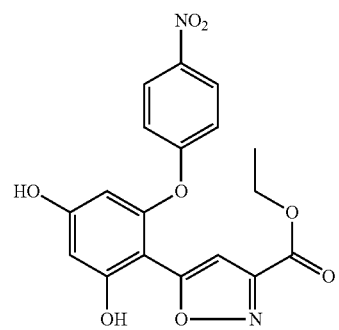 [SMILES: CCOC(=O)c1cc(-c2c(O)cc(O)cc2Oc2ccc([N+](=O)[O-])cc2)on1]

Scheme

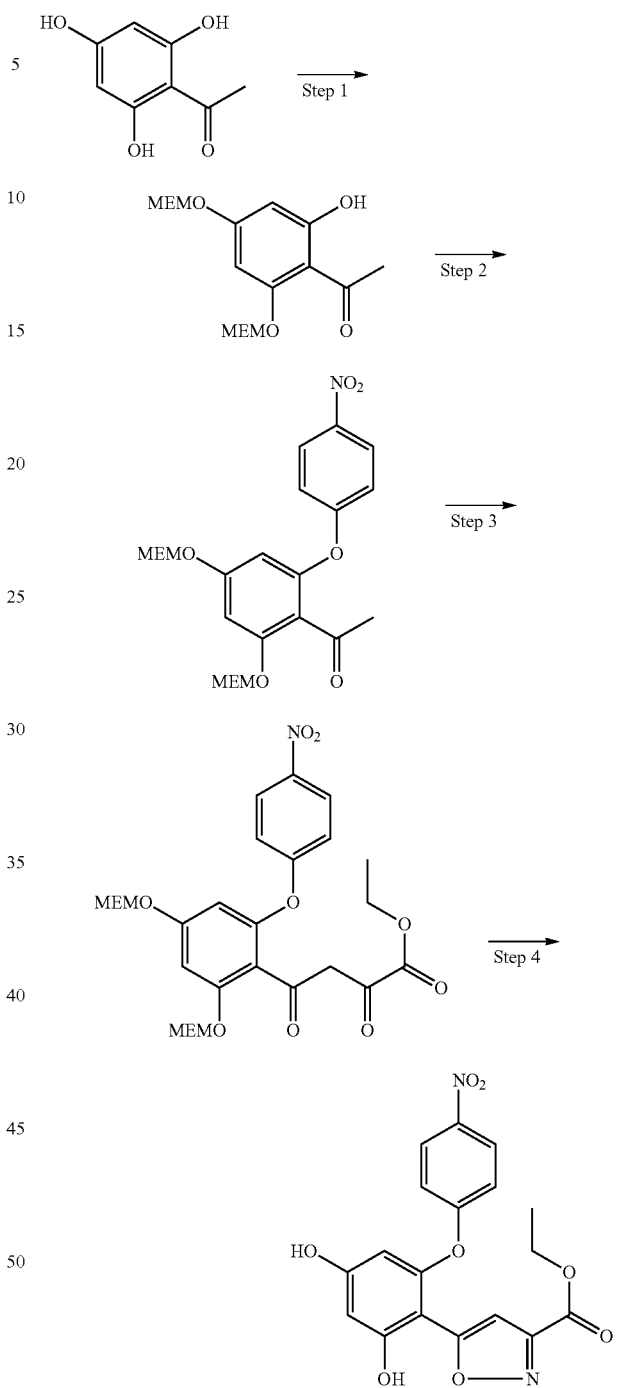

Step 1

1-{2-Hydroxy-4,6-bis[(2-methoxyethoxy)methoxy]phenyl}ethanone

To a stirred solution of 2,4,6-trihydroxyacetophenone (1.7 g, 10 mmol) in THF (50 mL) was added DIPEA (17 mL, 100 mmol, 10 eq) followed by the addition of 2-methoxyethoxymethylchloride (2.75 g, 22 mmol, 2.2 eq) at 0° C. After stirring overnight at 0° C., the solvent was removed, and the residue taken up in ethyl acetate was washed with 1 M HCl solution then with 1 M NaHCO₃ solution and dried. The crude was carefully chromatographed on silica gel eluting with hexane/ethyl acetate 6/4 to provide the title compound (2.2 g, 64% yield).

¹H NMR (400 MHz, DMSO-$d_6$) δ ppm 2.59 (s, 3H) 3.23 (s, 3H) 3.23 (s, 3H) 3.42-3.51 (m, 4H) 3.69-3.74 (m, 1H) 3.75-3.80 (m, 2H) 5.29 (s, 2H) 5.35 (s, 2H) 6.19 (d, 1H) 6.26 (d, 1H) 13.32 (s, 1H).

Step 2

1-{2,4-Bis[(2-methoxyethoxy)methoxy]-6-(4-nitrophenoxy)phenyl}ethanone

A stirred suspension of 1-{2-hydroxy-4,6-bis[(2-methoxyethoxy)methoxy]phenyl}ethanone (2.1 g, 6 mmol), potassium carbonate (0.85 g, 6 mmol) and 1-fluoro-4-nitrobenzene (0.86 g, 6.1 mmol) in DMSO (5 mL) was heated at 80° C. overnight. After dilution with ethyl acetate, the suspension was washed with brine and dried. After removal of the solvent, the residue was chromatographed on silica gel eluting with hexane/ethyl acetate 6/4 to afford the title compound (1.6 g, 54% yield).

¹H NMR (400 MHz, DMSO-$d_6$) δ ppm 2.6 (s, 3H) 3.21 (s, 3H) 3.22 (s, 3H) 3.43-3.51 (m, 4H) 3.68-3.76 (m, 1H) 3.73-3.81 (m, 2H) 5.30 (s, 2H) 5.34 (s, 2H) 6.20 (d, 1H) 6.25 (d, 1H) 7.15 (m, 2H) 8.24 m, 2H).

Step 3

Ethyl 4-{2,4-bis[(2-methoxyethoxy)methoxy]-6-(4-nitrophenoxy)phenyl}-2,4-dioxobutanoate Operating as in Example 1 Step 2, but employing 1-{2,4-bis[(2-methoxyethoxy)methoxy]-6-(4-nitrophenoxy)phenyl}ethanone instead of 1-[2,4-bis(benzyloxy)-6-(4-nitrophenoxy)phenyl]ethanone, the title compound was obtained in 64% yield.

¹H NMR (400 MHz, DMSO-$d_6$) δ ppm 1.37 (t, 3H) 3.22 (s, 3H) 3.25 (s, 3H) 3.41-3.50 (m, 4H) 3.70-3.71 (m, 1H) 3.75-3.82 (m, 2H) 4.38 (q, 2H) 4.58 (bs, 1H) 5.31 (s, 2H) 5.33 (s, 2H) 6.21 (d, 1H) 6.24 (d, 1H) 7.17 (m, 2H) 8.27 (m, 2H).

Step 4

Ethyl 5-[2,4-dihydroxy-6-(4-nitrophenoxy)phenyl]isoxazole-3-carboxylate

[(XXXI); (Z)—R=4-Nitrophenoxy, X=O, Y=N, W=CH, $R_1=C_3HSO_2$]

A stirred solution of ethyl 4-{2,4-bis[(2-methoxyethoxy)methoxy]-6-(4-nitrophenoxy)phenyl}-2,4-dioxobutanoate (0.65 g, 1.1 mmol) and hydroxylamine hydrochloride (0.01 g, 1.5 mmol) in ethanol (10 mL) was refluxed for 3 hours. After dilution with ethyl acetate and washing with brine and drying, the solvent was removed and the residue crystallized from a small volume of ethanol, to provide the title compound in 73% yield. Alternatively, the following Scheme illustrates the use of the MOM (CH₃OCH₂) instead of the MEM (CH₃OCH₂CH₂OCH₂) group:

Preparation of Ethyl 5-[2,4-dihydroxy-6-(4-nitrophenoxy)phenyl]isoxazole-3-carboxylate, via PG=methoxymethyl

[(XXXI), (Z)—R=4-Nitrophenoxy, X=O, Y=N, W=CH, $R'_1=CO_2C_2H_5$]

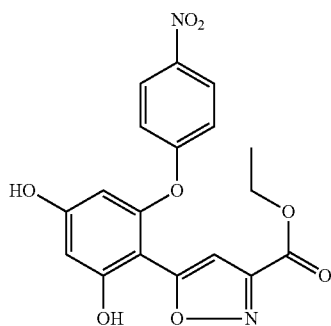 [SMILES: CCOC(=O)c1cc(-c2c(O)cc(O)cc2Oc2ccc([N+](=O)[O-])cc2)on1]

Scheme

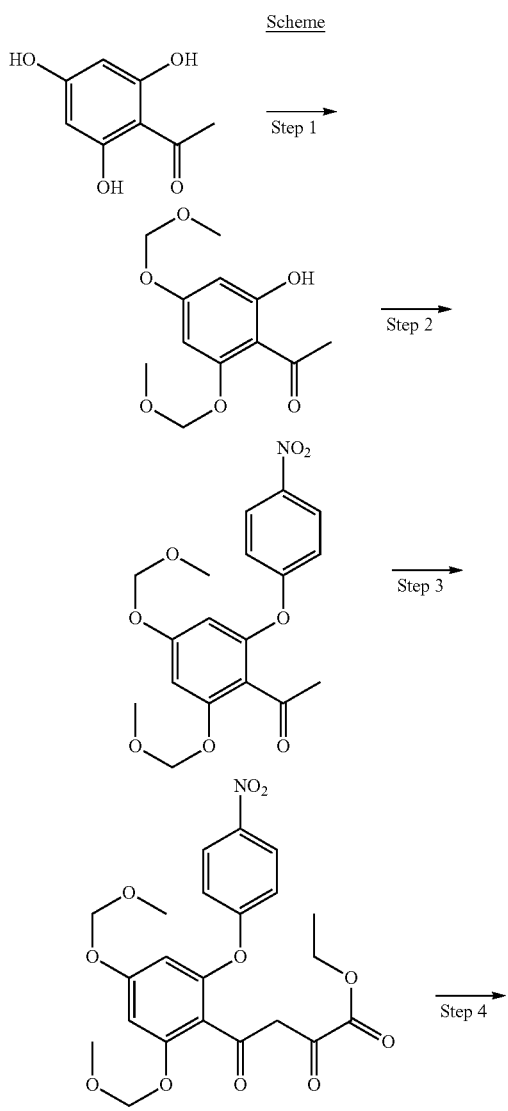

-continued

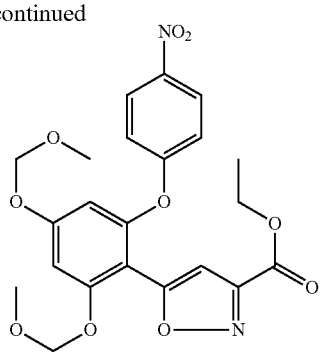

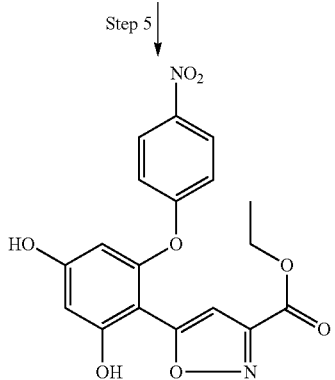

Step 1

1-[2-Hydroxy-4,6-bis(methoxymethoxy)phenyl]
ethanone

To a stirred solution of dimethoxymethane (66 mL, 745 mmol) and zinc bromide (0.5 g) in DCM (580 mL) was added drop wise acetyl chloride (53 mL, 745 mmol) during half an hour maintaining the temperature under 20° C. After stirring 3 hours at room temperature, the solution was diluted with DCM (1200 mL), then cooled at 5° C. before the portion wise addition of 1-(2,4,6-trihydroxyphenyl)ethanone (phloroacetophenone) (50 g, 208 mmol) followed by the drop wise addition of DIPEA (208 mL, 1.19 mol). The resulting cloudy solution was stirred overnight, and then was washed with a NH$_4$Cl saturated solution followed by washing with 10% citric acid solution. After drying over Na$_2$SO$_4$, the solvent was removed and the residue (78 g) nearly pure was used for the next step.

$^1$H NMR (400 MHz, DMSO-d$_6$) δ ppm 2.60 (s, 3H) 3.38 (s, 3H) 3.44 (s, 3H) 5.22 (s, 2H) 5.30 (s, 2H) 6.19 (d, 1H) 6.24 (d, 1H) 13.31 (s, 1H).

Step 2

1-[2,4-Bis(methoxymethoxy)-6-(4-nitrophenoxy)
phenyl]ethanone

To a stirred suspension of 1-[2-hydroxy-4,6-bis(methoxymethoxy)phenyl]ethanone (78 g, 298 mmol) and K$_2$CO$_3$ (45.3 g, 328 mmol) in DMSO (500 mL) and water (40 ml) was added 4-nitro-1-fluorobenzene (46.3 g, 328 mmol, 1.1 eq). After stirring for 15 min. at room temperature, the resulting suspension was heated for 6 hours at 55° C. After cooling, the dark solution was diluted with ethyl acetate (2000 mL) and thoroughly washed with 10% citric acid solution, then with brine and dried over Na$_2$SO$_4$. The solvent was removed and the residue was columned over silica gel eluting with cyclohexane/ethyl acetate 3/1, to provide the title compound (56 g, 52% yield).

$^1$H NMR (400 MHz, DMSO-d$_6$) δ ppm 2.38 (s, 3H) 3.37 (s, 3H) 3.41 (s, 3H) 5.19 (s, 2H) 5.28 (s, 2H) 6.47 (d 1H) 6.76 (d, 1H) 7.07-7.16 (m, 2H) 8.20-8.28 (m, 2H).

Step 3

Ethyl 4-[2,4-bis(methoxymethoxy)-6-(4-nitrophenoxy)phenyl]-2,4-dioxobutanoate

To a stirred solution of sodium tert-butoxide (31.5 g, 328 mmol) and diethyl oxalate (60.5 mL, 3 eq.) in THF (250 mL) was slowly added dropwise a solution of 1-[2,4-bis(methoxymethoxy)-6-(4-nitrophenoxy)phenyl]ethanone (56 g, 149 mmol) in THF (350 mL) at −5° C. After stirring for 1 hour at this temperature, the resulting solution was stirred for further 3 hours at room temperature. The solution was then taken up in 10% citric acid solution (2000 mL) and thoroughly extracted with ethyl acetate. After washing with brine and drying over Na$_2$SO$_4$, the solvent was removed to provide a yellowish residue that was taken up in light petrol ether to remove the excess of diethyl oxalate to afford the quite pure title compound (58 g, 81% yield).

Step 4

Ethyl 5-[2,4-bis(methoxymethoxy)-6-(4-nitrophenoxy)phenyl]isoxazole-3-carboxylate To a stirred solution of ethyl 4-[2,4-bis(methoxymethoxy)-6-(4-nitrophenoxy)phenyl]-2,4-dioxobutanoate (71 g, 149 mmol) in THF (250 mL) and ethanol (500 mL) is added CH$_3$COONa (24.4 g, 298 mmol) and NH$_2$OH.HCl (22.8 g, 328 mmol) at room temperature. After the conversion to the oximes is complete, 6 M HCl solution was added dropwise to reach pH 2 to promote the cyclization. After stirring for 24 hours, Na$_2$HPO$_4$ was added to reach pH 6 and the suspension taken up in ethyl acetate was thoroughly washed with brine and dried over Na$_2$SO$_4$. The solvent was removed and the residue was crystallized from a mixture of MTBE (240 mL) and hexane (180 mL), to provide the title compound (35 g, 49% yield).

$^1$H NMR (400 MHz, DMSO-d$_6$) δ ppm 1.29 (t, 3H) 3.38 (s, 3H) 3.39 (s, 3H) 4.34 (q, Hz, 2H) 5.25 (s, 2H) 5.33 (s, 2H) 6.62 (d, 1H) 6.89 (d, 1H) 6.96 (s, 1H) 7.15 (d, 2H) 8.23 (d, 2H).

Step 5

Ethyl 5-[2,4-dihydroxy-6-(4-nitrophenoxy)phenyl]
isoxazole-3-carboxylate

To a stirred solution of ethyl 5-[2,4-bis(methoxymethoxy)-6-(4-nitrophenoxy)phenyl]isoxazole-3-carboxylate (25 g, 52 mmol) in ethanol (150 mL) was added 4 M HCl solution in dioxane at room temperature. The solution was set aside for 5 hours then the solvent was evaporated off and the residue taken up in diethyl ether, to provide the title compound (17.1 g, 83% yield).

$^1$H NMR (400 MHz, DMSO-d$_6$) δ ppm 1.28 (t, 3H) 4.27-4.36 (m, 2H) 6.10 (d, 1H) 6.45 (d, 1H) 6.86-6.89 (m, 1H) 7.07-7.16 (m, 2H) 8.18-8.25 (m, 2H) 10.35 (s, 1H) 10.77 (s, 1H).

EXAMPLE 4

5-[2,4-Dihydroxy-6-(4-nitrophenoxy)phenyl]-N-[2-(methylamino)ethyl]isoxazole-3-carboxamide

[(I); (Z)—R=4-Nitrophenoxy, X=O, Y=N, W=CH, R$_1$=C$_4$H$_9$N$_2$O]

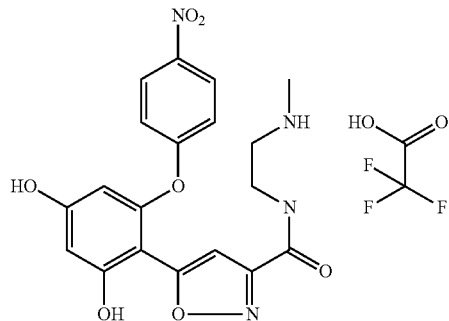 [SMILES: CNCCNC(=O)c1cc(-c2c(O)cc(O)cc2Oc2ccc([N+](=O)[O-])cc2)on1 ; O=C(O)C(F)(F)F]

Scheme

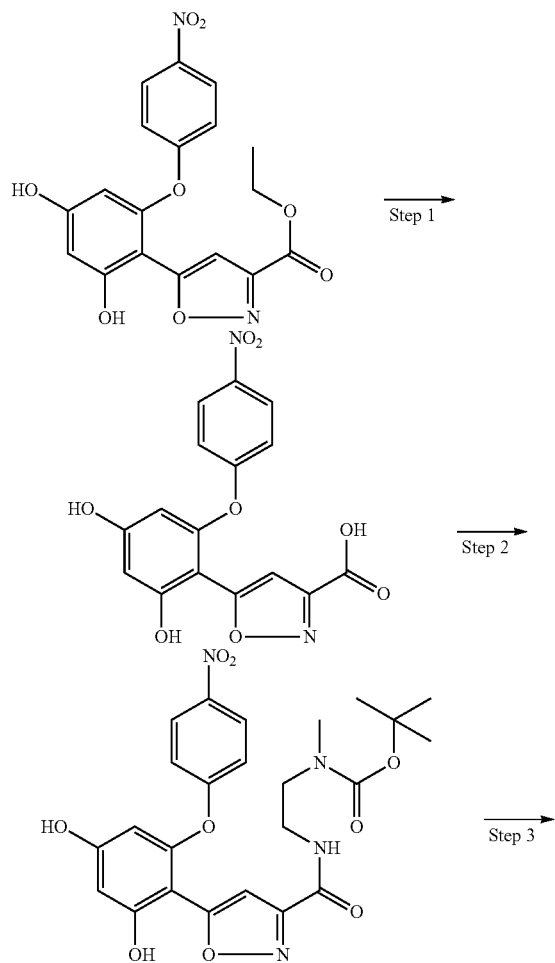

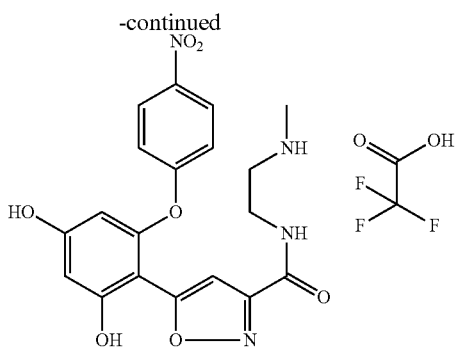

Step 1

5-[2,4-Dihydroxy-6-(4-nitrophenoxy)phenyl]isoxazole-3-carboxylic acid

[(XXXI); (Z)—R=4-Nitrophenoxy, X=O, Y=N, W=CH, R$_1$=COOH]

To a stirred solution of ethyl 5-[2,4-dihydroxy-6-(4-nitrophenoxy)phenyl]isoxazole-3-carboxylate (3.5 g, 10 mmol) in ethanol (50 mL) was added 2 M NaOH solution (5.5 mL, 1.1 eq.) at room temperature. After stirring for 3 hours, the resulting solution was concentrated and diluted with ethyl acetate and washed with 1M HCl solution, brine and dried over Na$_2$SO$_4$. The solvent was removed affording after crystallization from a small volume of acetone, the title compound (2.1 g, 65% yield).

Step 2

Tert-butyl {2-[({5-[2,4-dihydroxy-6-(4-nitrophenoxy)phenyl]isoxazol-3-yl}carbonyl)amino]ethyl}methylcarbamate

[(I); (Z)—R=4-Nitrophenoxy, X=O, Y=N, W=CH, R$_1$=CONHC$_8$H$_{16}$NO$_2$]

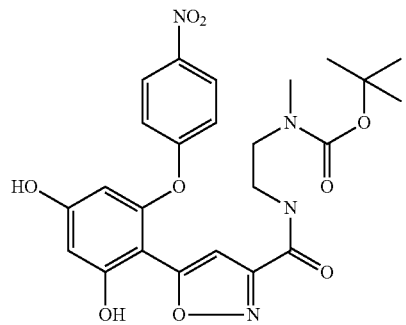 [SMILES: CN(CCNC(=O)c1cc(-c2c(O)cc(O)cc2Oc2ccc([N+](=O)[O-])cc2)on1)C(=O)OC(C)(C)C]

To a suspension of 5-[2,4-dihydroxy-6-(4-nitrophenoxy)phenyl]isoxazole-3-carboxylic acid (0.032 g, 0.09 mmol) in N,N'-dimethylacetamide (0.5 mL), TBTU (0.034 mg, 0.11 mmol) and DIPEA (0.017 mL, 0.18 mmol) were added all in a 1 dram vial (4 mL working volume). The mixture was agitated at room temperature for 30 minutes. Then tert-butyl (2-aminoethyl)methylcarbamate (0.023 g, 0.13 mmol), dissolved in DMA (0.5 mL), was added and the reaction was agitated for an additional 16 hours at room temperature.

HPLC analysis after 16 hours indicated the conversion of the starting material to product. The solvent was removed in vacuo.

Step 3

5-[2,4-Dihydroxy-6-(4-nitrophenoxy)phenyl]-N-[2-(methylamino)ethyl]isoxazole-3-carboxamide trifluoroacetate

[(I); (Z)—R=4-Nitrophenoxy, X=O, Y=N, W=CH, $R_1=C_4H_9N_2O$]

To the tert-butyl {2-[({5-[2,4-dihydroxy-6-(4-nitrophenoxy)phenyl]isoxazol-3-yl}carbonyl)amino]ethyl}methylcarbamate compound prepared in Step 1, TFA/DCM (1:1) (0.5 mL) was charged to the vial and agitated for 1 hour at ambient temperature. The solvent was then removed in vacuo and the product was purified via semi-preparative HPLC according to the protocol indicated below.

$^1$H NMR (400 MHz, DMSO-$d_6$) δ ppm 2.56 (t, 3H) 3.05 (qd, 2H) 3.46-3.54 (m, 2H) 6.11 (d, 1H) 6.47 (d, 1H) 6.83 (s, 1H) 7.09-7.12 (m, 2H) 8.22 (d 2H) 8.32 (br. s., 1H) 8.81 (t, 1H) 10.35 (br. s., 1H) 10.76 (s, 1H).

EXAMPLE 5

5-[3,5-Dihydroxy-2-(4-nitrophenoxy)phenyl]-N-(piperidin-4-yl)isoxazole-3-carboxamide hydrochloride

[(I); (Z)—R=4-Nitrophenoxy, X=O, Y=N, W=CH, $R_1=C_6H_{11}N_2O$]

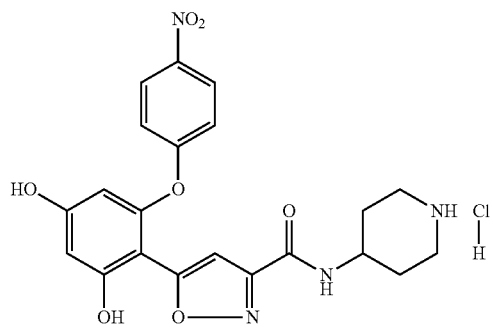

Operating as in Example 4 Step 1 and 2, but employing tert-butyl 4-aminopiperidine-1-carboxylate instead of tert-butyl (2-aminoethyl)methylcarbamate, the title compound was obtained in 13% yield.

$^1$H NMR (400 MHz, DMSO-$d_6$) δ ppm 1.72 (qd, 2H) 1.91 (m, 2H) 2.91-3.06 (m, 2H) 3.96-4.08 (m, 1H) 6.11 (d, 1H) 6.48 (d, 1H) 6.83 (s, 1H) 7.10 (d, 2H) 8.22 (d, 2H) 8.82 (d, 1H) 10.35 (s, 1H) 10.77 (s, 1H).

EXAMPLE 6

N-(1-Azabicyclo[2.2.2]oct-3-yl)-5-[2,4-dihydroxy-6-(4-nitrophenoxy)phenyl]isoxazole-3-carboxamide

[(I); (Z)—R=4-Nitrophenoxy, X=O, Y=N, W=CH, $R_1=C_8H_{13}N_2O$]

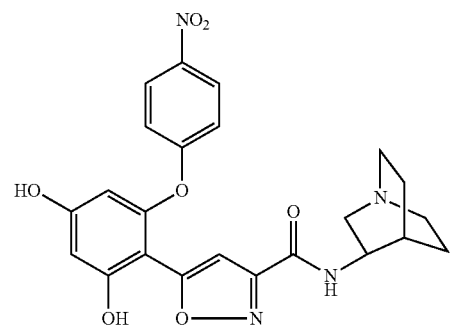 [SMILES: O=C(NC1CN2CCC1CC2)c1cc(-c2c(O)cc(O)cc2Oc2ccc([N+](=O)[O-])cc2)on1]

Operating as in Example 4 Step 1, but employing (R)-(+)-3-aminoquinuclidine instead of tert-butyl (2-aminoethyl)methylcarbamate, the title compound was obtained in 54% yield.

$^1$H NMR (400 MHz, DMSO-$d_6$) δ ppm 3.88 (br. s., 1H) 6.07 (d, 1H) 6.43 (d, 1H) 6.79 (s, 1H) 7.07 (d, 2H) 8.19 (d, 2H) 8.61 (d, 1H) 9.61-11.41 (m, 2H).

EXAMPLE 7

5-[2,4-Dihydroxy-6-(4-nitrophenoxy)phenyl]-N-(1-ethylpiperidin-3-yl)isoxazole-3-carboxamide

[(I); (Z)—R=4-Nitrophenoxy, X=O, Y=N, W=CH, $R_1=C_8H_{16}N_2O$]

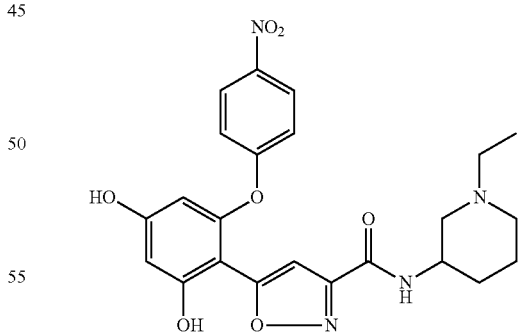

Operating as in Example 4 Step 1, but employing 1-ethylpiperidin-3-ylamine instead of tert-butyl (2-aminoethyl)methylcarbamate, the title compound was obtained in 43% yield.

$^1$H NMR (400 MHz, DMSO-$d_6$) δ ppm 0.98 (t, Hz, 3H) 3.80-3.96 (m, 1H) 6.11 (d, 1H) 6.47 (d, 1H) 6.82 (s, 1H) 7.01-7.17 (m, 2H) 8.15-8.27 (m, 2H) 8.35 (br. s., 1H) 10.31 (s, 1H) 10.73 (br. s., 1H).

EXAMPLE 8

N-(1-Acetylpiperidin-4-yl)-5-[2,4-dihydroxy-6-(4-nitrophenoxy)phenyl]isoxazole-3-carboxamide

[(I); (Z)—R=4-Nitrophenoxy, X=O, Y=N, W=CH, $R_1=C_8H_{13}N_2O$]

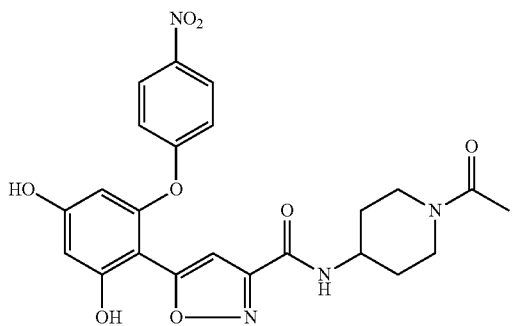

Operating as in Example 4 Step 1, but employing 1-(4-amino-piperidin-1-yl)-ethanone instead of tert-butyl (2-aminoethyl)methylcarbamate, the title compound was obtained in 38% yield.

$^1$H NMR (400 MHz, DMSO-$d_6$) δ ppm 1.98 (s, 3H) 3.02-3.15 (m, 2H) 3.68 (d, 1H) 3.79 (d, 1H) 3.89-4.07 (m, 2H) 4.13 (d, 1H) 4.31 (d, 1H) 6.10 (dd, 2H) 6.46 (d, 2H) 6.81 (d, 2H) 7.10 (d, 4H) 7.97 (s, 1H) 8.22 (d, 4H) 8.60 (d, 1H) 8.64 (d, 1H) 10.30 (s, 2H) 10.72 (s, 2H).

EXAMPLE 9

5-[2,4-Dihydroxy-6-(4-nitrophenoxy)phenyl]-N-(1,2,2,6,6-pentamethylpiperidin-4-yl)isoxazole-3-carboxamide

[(I); (Z)—R=4-Nitrophenoxy, X=O, Y=N, W=CH, $R_1=C_{11}H_{21}N_2O$]

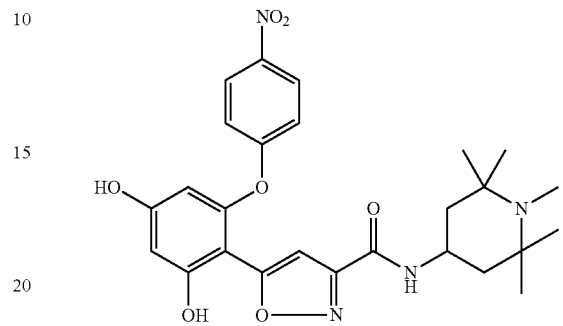

Operating as in Example 4 Step 1, but employing 1,2,2,6,6-pentamethyl-piperidin-4-ylamine instead of tert-butyl (2-aminoethyl)methylcarbamate, the title compound was obtained in 21% yield.

$^1$H NMR (400 MHz, DMSO-$d_6$) δ ppm 0.96-1.10 (m, 12H) 1.35-1.48 (m, 2H) 1.53-1.67 (m, 2H) 2.16 (br. s., 3H) 4.02-4.20 (m, 1H) 6.10 (d, 1H) 6.46 (d, 1H) 6.79 (s, 1H) 7.04-7.15 (m, 2H) 8.15-8.27 (m, 2H) 8.46 (d, 1H) 10.31 (br. s., 1H) 10.71 (br. s., 1H).

EXAMPLE 10

Operating analogously as in Example 4 Step 1, but employing the suitable amines, the titles compounds reported in the following tables were prepared.

| STRUCTURE | Name | M + H | RT | METHOD |
|---|---|---|---|---|
| 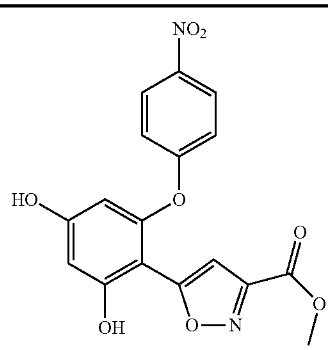 | methyl 5-[2,4-dihydroxy-6-(4-nitrophenoxy)phenyl]-isoxazole-3-carboxylate | 373.3 | 3.8 | 3 |
| 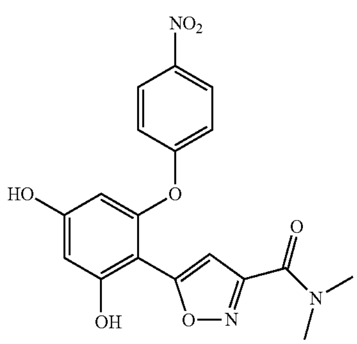 [SMILES: CN(C)C(=O)c1cc(-c2c(O)cc(O)cc2Oc2ccc([N+](=O)[O-])cc2)on1] | 5-[2,4-dihydroxy-6-(4-nitrophenoxy)phenyl]-N,N-dimethylisoxazole-3-carboxamide | 386.3 | 1.162 | 1 |

| STRUCTURE | Name | M + H | RT | METHOD |
|---|---|---|---|---|
| 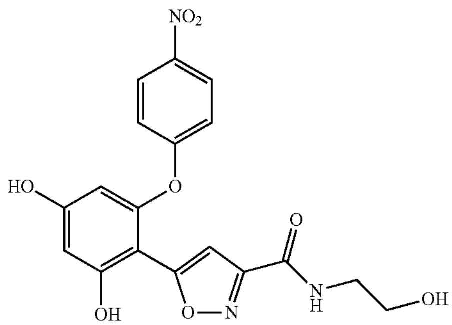 [SMILES: O=C(NCCO)c1cc(-c2c(O)cc(O)cc2Oc2ccc([N+](=O)[O-])cc2)on1] | 5-[2,4-dihydroxy-6-(4-nitrophenoxy)phenyl]-N-(2-hydroxyethyl)isoxazole-3-carboxamide | 402.3 | 2.4 | 3 |
| 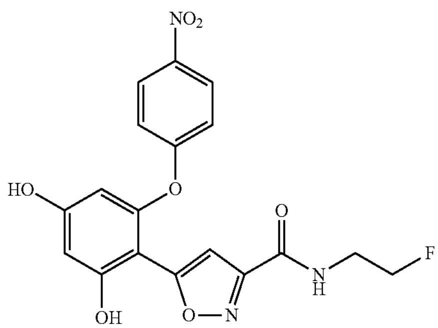 | 5-[2,4-dihydroxy-6-(4-nitrophenoxy)phenyl]-N-(2-fluoroethyl)isoxazole-3-carboxamide | 404.3 | 1.167 | 1 |
| 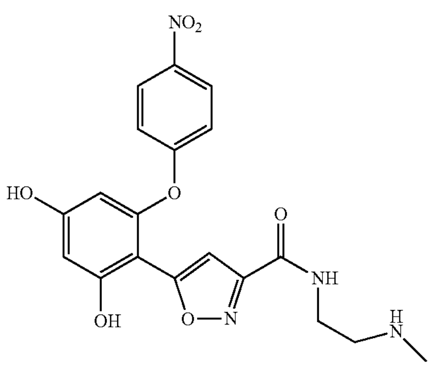 [SMILES: CNCCNC(=O)c1cc(-c2c(O)cc(O)cc2Oc2ccc([N+](=O)[O-])cc2)on1] | 5-[2,4-dihydroxy-6-(4-nitrophenoxy)phenyl]-N-[2-(methylamino)ethyl]isoxazole-3-carboxamide | 415.4 | 4.11 | 4 |
| | 5-[2,4-dihydroxy-6-(4-nitrophenoxy)phenyl]-N-(3-hydroxypropyl)isoxazole-3-carboxamide | 416.4 | 1.019 | 1 |

-continued

| STRUCTURE | Name | M + H | RT | METHOD |
|---|---|---|---|---|
|  | 5-[2,4-dihydroxy-6-(4-nitrophenoxy)phenyl]-N-(2-methoxyethyl)isoxazole-3-carboxamide | 416.4 | 1.151 | 1 |
| 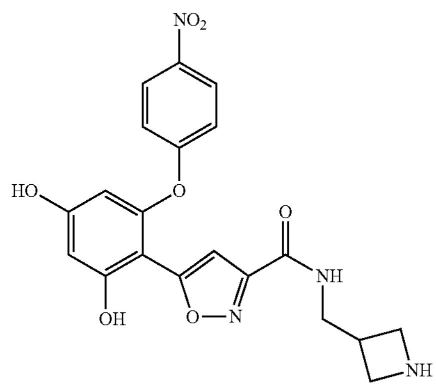 [SMILES: O=C(NCC1CNC1)c1cc(-c2c(O)cc(O)cc2Oc2ccc([N+](=O)[O-])cc2)on1] | N-(azetidin-3-ylmethyl)-5-[2,4-dihydroxy-6-(4-nitrophenoxy)phenyl]isoxazole-3-carboxamide | 427.4 | 1.379 | 1 |
| 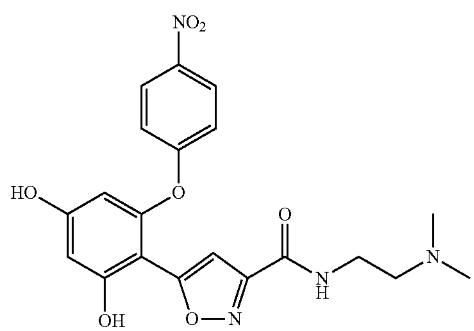 [SMILES: CN(C)CCNC(=O)c1cc(-c2c(O)cc(O)cc2Oc2ccc([N+](=O)[O-])cc2)on1] | 5-[2,4-dihydroxy-6-(4-nitrophenoxy)phenyl]-N-[2-(dimethylamino)ethyl]isoxazole-3-carboxamide | 429.4 | 2.1 | 3 |
| 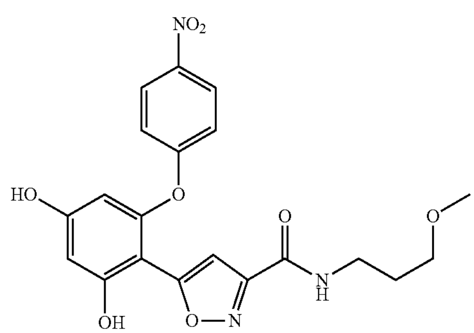 [SMILES: COCCCNC(=O)c1cc(-c2c(O)cc(O)cc2Oc2ccc([N+](=O)[O-])cc2)on1] | 5-[2,4-dihydroxy-6-(4-nitrophenoxy)phenyl]-N-(3-methoxypropyl)isoxazole-3-carboxamide | 430.4 | 1.195 | 1 |

-continued

| STRUCTURE | Name | M + H | RT | METHOD |
|---|---|---|---|---|
| 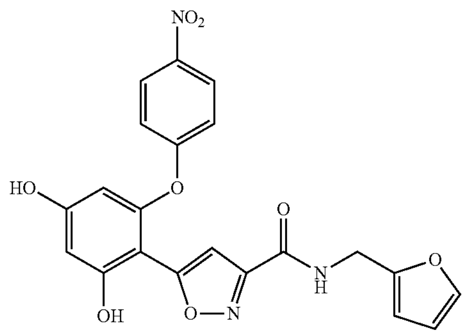 [SMILES: O=C(NCc1ccco1)c1cc(-c2c(O)cc(O)cc2Oc2ccc([N+](=O)[O-])cc2)on1] | 5-[2,4-dihydroxy-6-(4-nitrophenoxy)phenyl]-N-(furan-2-ylmethyl)isoxazole-3-carboxamide | 438.4 | 1.32 | 1 |
| 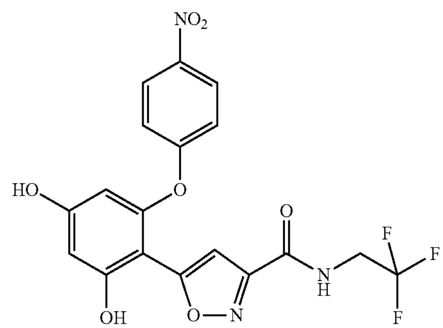 [SMILES: O=C(NCC(F)(F)F)c1cc(-c2c(O)cc(O)cc2Oc2ccc([N+](=O)[O-])cc2)on1] | 5-[2,4-dihydroxy-6-(4-nitrophenoxy)phenyl]-N-(2,2,2-trifluoroethyl)isoxazole-3-carboxamide | 440.3 | 3.3 | 3 |
| 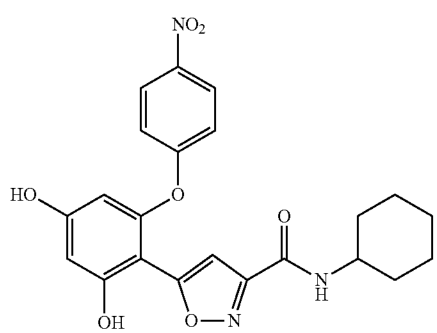 [SMILES: O=C(NC1CCCCC1)c1cc(-c2c(O)cc(O)cc2Oc2ccc([N+](=O)[O-])cc2)on1] | N-cyclohexyl-5-[2,4-dihydroxy-6-(4-nitrophenoxy)phenyl]isoxazole-3-carboxamide | 440.4 | 1.489 | 1 |
| 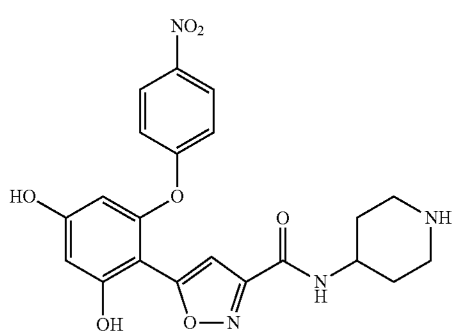 [SMILES: O=C(NC1CCNCC1)c1cc(-c2c(O)cc(O)cc2Oc2ccc([N+](=O)[O-])cc2)on1] | 5-[2,4-dihydroxy-6-(4-nitrophenoxy)phenyl]-N-(piperidin-4-yl)isoxazole-3-carboxamide | 441.4 | 1.464 | 1 |

-continued
| STRUCTURE | Name | M + H | RT | METHOD |
|---|---|---|---|---|
| 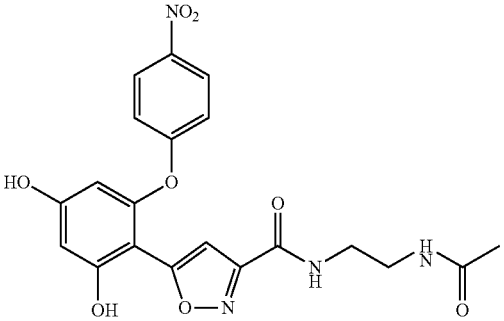 [SMILES: CC(=O)NCCNC(=O)c1cc(-c2c(O)cc(O)cc2Oc2ccc([N+](=O)[O-])cc2)on1] | N-[2-(acetylamino)ethyl]-5-[2,4-dihydroxy-6-(4-nitrophenoxy)phenyl]isoxazole-3-carboxamide | 443.4 | 0.996 | 1 |
| 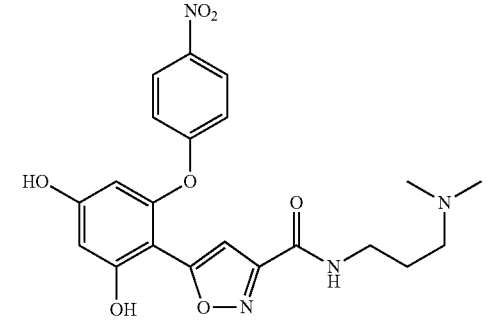 [SMILES: CN(C)CCCNC(=O)c1cc(-c2c(O)cc(O)cc2Oc2ccc([N+](=O)[O-])cc2)on1] | 5-[2,4-dihydroxy-6-(4-nitrophenoxy)phenyl]-N-[3-(dimethylamino)propyl]isoxazole-3-carboxamide | 443.4 | 0.957 | 1 |
| 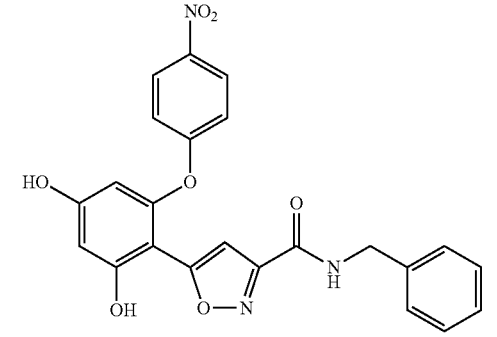 [SMILES: O=C(NCc1ccccc1)c1cc(-c2c(O)cc(O)cc2Oc2ccc([N+](=O)[O-])cc2)on1] | N-benzyl-5-[2,4-dihydroxy-6-(4-nitrophenoxy)phenyl]isoxazole-3-carboxamide | 448.4 | 1.424 | 1 |
| 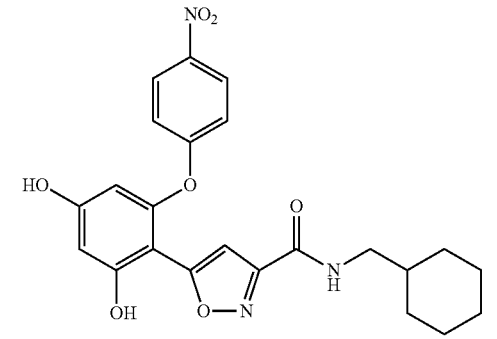 [SMILES: O=C(NCC1CCCCC1)c1cc(-c2c(O)cc(O)cc2Oc2ccc([N+](=O)[O-])cc2)on1] | N-(cyclohexylmethyl)-5-[2,4-dihydroxy-6-(4-nitrophenoxy)phenyl]isoxazole-3-carboxamide | 454.5 | 1.561 | 1 |

| STRUCTURE | Name | M + H | RT | METHOD |
|---|---|---|---|---|
| 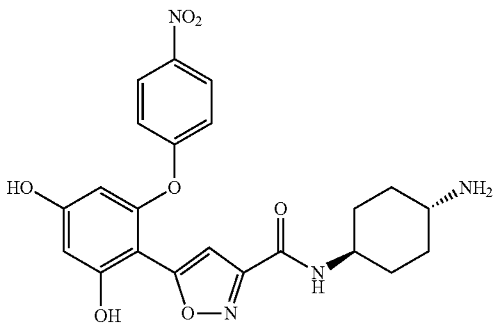 [SMILES: N[C@H]1CC[C@H](NC(=O)c2cc(-c3c(O)cc(O)cc3Oc3ccc([N+](=O)[O-])cc3)on2)CC1] | N-(trans-4-aminocyclohexyl)-5-[2,4-dihydroxy-6-(4-nitrophenoxy)phenyl]isoxazole-3-carboxamide | 455.4 | 1.051 | 1 |
| 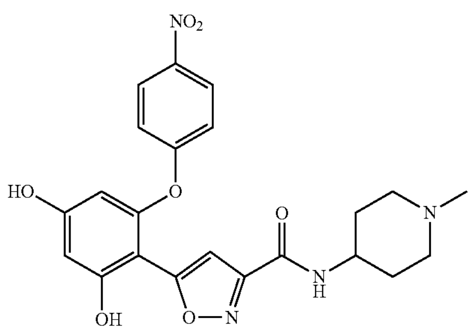 [SMILES: CN1CCC(NC(=O)c2cc(-c3c(O)cc(O)cc3Oc3ccc([N+](=O)[O-])cc3)on2)CC1] | 5-[2,4-dihydroxy-6-(4-nitrophenoxy)phenyl]-N-(1-methylpiperidin-4-yl)isoxazole-3-carboxamide | 455.4 | 0.95 | 1 |
| 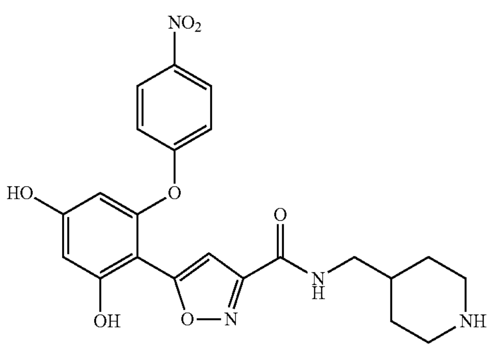 [SMILES: O=C(NCC1CCNCC1)c1cc(-c2c(O)cc(O)cc2Oc2ccc([N+](=O)[O-])cc2)on1] | 5-[2,4-dihydroxy-6-(4-nitrophenoxy)phenyl]-N-(piperidin-4-ylmethyl)isoxazole-3-carboxamide | 455.4 | 3.7 | 3 |
| 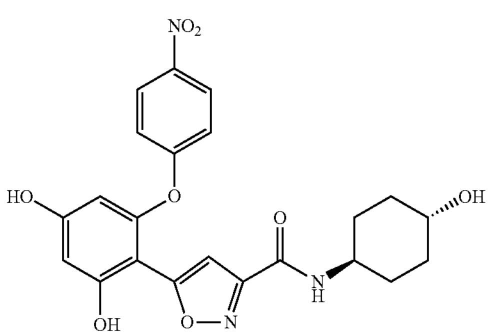 [SMILES: O=C(N[C@H]1CC[C@H](O)CC1)c1cc(-c2c(O)cc(O)cc2Oc2ccc([N+](=O)[O-])cc2)on1] | 5-[2,4-dihydroxy-6-(4-nitrophenoxy)phenyl]-N-(trans-4-hydroxycyclohexyl)isoxazole-3-carboxamide | 456.4 | 1.083 | 1 |

| STRUCTURE | Name | M + H | RT | METHOD |
|---|---|---|---|---|
| 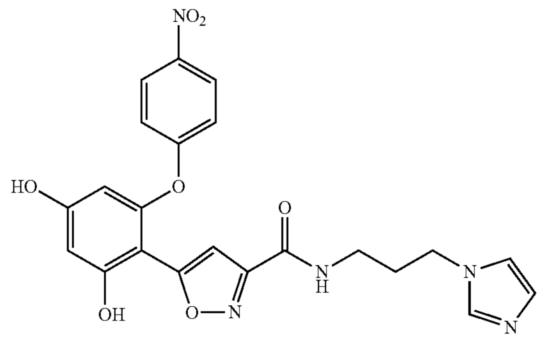 [SMILES: O=C(NCCCn1ccnc1)c1cc(-c2c(O)cc(O)cc2Oc2ccc([N+](=O)[O-])cc2)on1] | 5-[2,4-dihydroxy-6-(4-nitrophenoxy)phenyl]-N-[3-(1H-imidazol-1-yl)propyl]isoxazole-3-carboxamide | 466.4 | 0.981 | 1 |
| 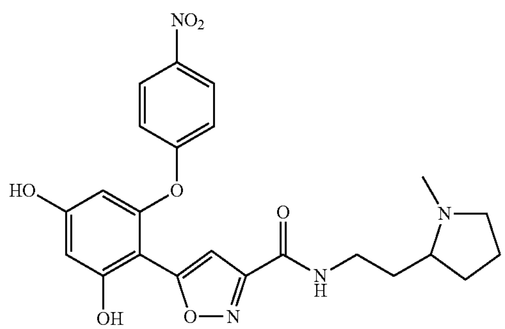 [SMILES: CN1CCCC1CCNC(=O)c1cc(-c2c(O)cc(O)cc2Oc2ccc([N+](=O)[O-])cc2)on1] | 5-[2,4-dihydroxy-6-(4-nitrophenoxy)phenyl]-N-[2-(1-methylpyrrolidin-2-yl)ethyl]isoxazole-3-carboxamide | 469.5 | 1.002 | 1 |
| 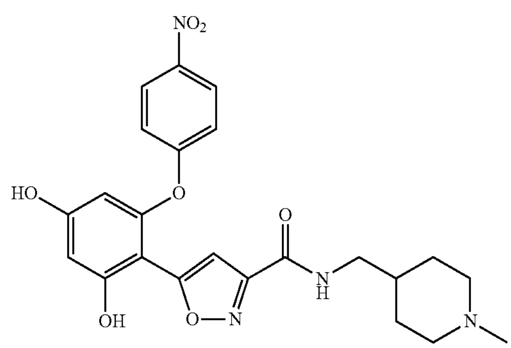 [SMILES: CN1CCC(CNC(=O)c2cc(-c3c(O)cc(O)cc3Oc3ccc([N+](=O)[O-])cc3)on2)CC1] | 5-[2,4-dihydroxy-6-(4-nitrophenoxy)phenyl]-N-[(1-methylpiperidin-4-yl)methyl]isoxazole-3-carboxamide | 469.5 | 0.977 | 1 |
| 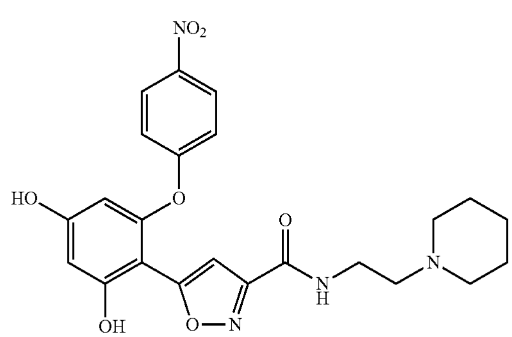 [SMILES: O=C(NCCN1CCCCC1)c1cc(-c2c(O)cc(O)cc2Oc2ccc([N+](=O)[O-])cc2)on1] | 5-[2,4-dihydroxy-6-(4-nitrophenoxy)phenyl]-N-[2-(piperidin-1-yl)ethyl]isoxazole-3-carboxamide | 469.5 | 1.049 | 1 |

-continued

| STRUCTURE | Name | M + H | RT | METHOD |
|---|---|---|---|---|
| 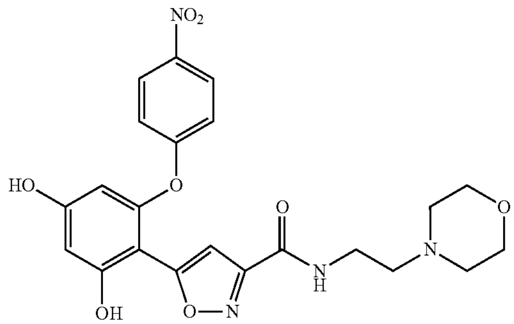 [SMILES: O=C(NCCN1CCOCC1)c1cc(-c2c(O)cc(O)cc2Oc2ccc([N+](=O)[O-])cc2)on1] | 5-[2,4-dihydroxy-6-(4-nitrophenoxy)phenyl]-N-[2-(morpholin-4-yl)ethyl]isoxazole-3-carboxamide | 471.4 | 0.966 | 1 |
| 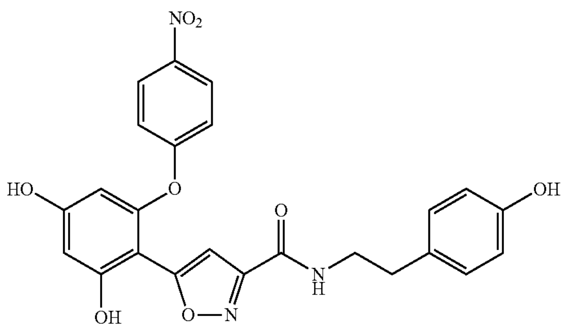 [SMILES: O=C(NCCc1ccc(O)cc1)c1cc(-c2c(O)cc(O)cc2Oc2ccc([N+](=O)[O-])cc2)on1] | 5-[2,4-dihydroxy-6-(4-nitrophenoxy)phenyl]-N-[2-(4-hydroxyphenyl)ethyl]isoxazole-3-carboxamide | 478.4 | 3 | 3 |
| 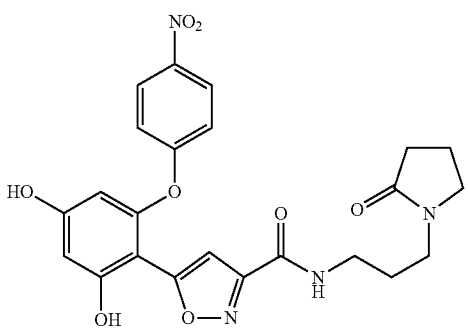 [SMILES: O=C(NCCCN1CCCC1=O)c1cc(-c2c(O)cc(O)cc2Oc2ccc([N+](=O)[O-])cc2)on1] | 5-[2,4-dihydroxy-6-(4-nitrophenoxy)phenyl]-N-[3-(2-oxopyrrolidin-1-yl)propyl]isoxazole-3-carboxamide | 483.5 | 1.124 | 1 |
| 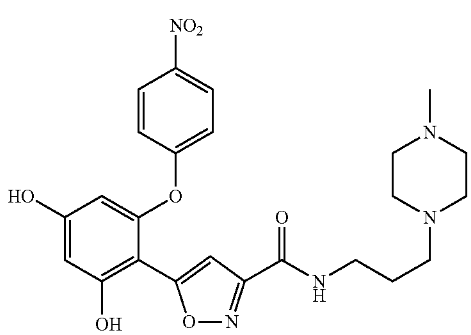 [SMILES: CN1CCN(CCCNC(=O)c2cc(-c3c(O)cc(O)cc3Oc3ccc([N+](=O)[O-])cc3)on2)CC1] | 5-[2,4-dihydroxy-6-(4-nitrophenoxy)phenyl]-N-[3-(4-methylpiperazin-1-yl)propyl]isoxazole-3-carboxamide | 498.5 | 0.869 | 1 |

| STRUCTURE | Name | M + H | RT | METHOD |
|---|---|---|---|---|
| 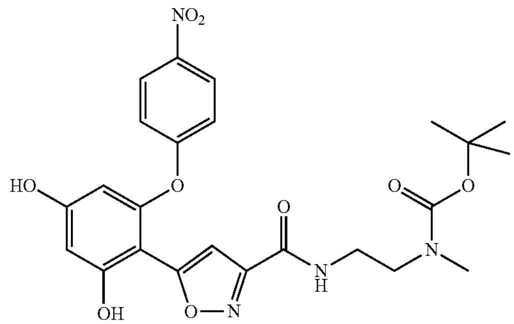 [SMILES: CN(CCNC(=O)c1cc(-c2c(O)cc(O)cc2Oc2ccc([N+](=O)[O-])cc2)on1)C(=O)OC(C)(C)C] | tert-butyl {2-[({5-[2,4-dihydroxy-6-(4-nitrophenoxy)phenyl]isoxazol-3-yl}carbonyl)amino]ethyl}methylcarbamate | 515.5 | 1.361 | 1 |
| 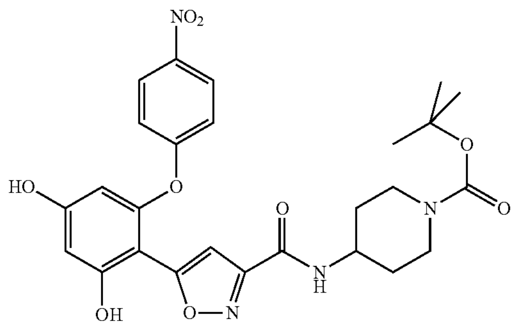 [SMILES: CC(C)(C)OC(=O)N1CCC(NC(=O)c2cc(-c3c(O)cc(O)cc3Oc3ccc([N+](=O)[O-])cc3)on2)CC1] | tert-butyl {4-[({5-[2,4-dihydroxy-6-(4-nitrophenoxy)phenyl]isoxazol-3-yl}carbonyl)amino]piperidine-1-carboxylate | 541.5 | 1.464 | 1 |

EXAMPLE 11

N-(1-Cyclohexylpiperidin-4-yl)-5-[2,4-dihydroxy-6-(4-nitrophenoxy)phenyl]isoxazole-3-carboxamide

[(I); (Z)—R=4-Nitrophenoxy, X=O, Y=N, W=CH, $R_1=C_{12}H_{21}N_2O$]

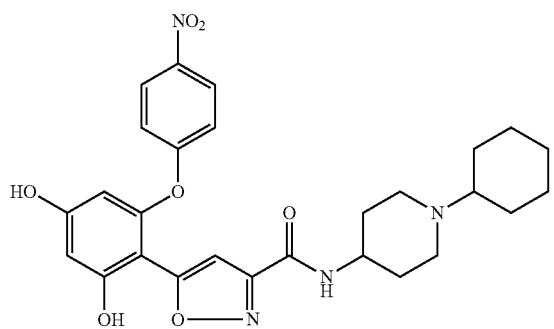 [SMILES: O=C(NC1CCN(C2CCCCC2)CC1)c1cc(-c2c(O)cc(O)cc2Oc2ccc([N+](=O)[O-])cc2)on1]

To a stirred solution of 5-[3,5-dihydroxy-2-(4-nitrophenoxy)phenyl]-N-(piperidin-4-yl)isoxazole-3-carboxamide hydrochloride (0.75 g, 1.7 mmol) and cyclohexanone (0.24 g, 1.5 eq.) in DMF (25 mL) was added portion wise $(CH_3)_4NBH(CH_3COO)_3$ (1.33 g, 3 eq.). After stirring at room temperature for 3 hours, the solution was taken up in ethyl acetate and thoroughly washed with brine. After drying over $Na_2SO_4$, the solvent was removed and the residue was carefully chromatographed over silica gel eluting with ethyl acetate/hexane 7/3 to provide the title compound (0.57 g, 64% yield).

$^1$H NMR (400 MHz, DMSO-$d_6$) δ ppm 6.11 (d, 1H) 6.47 (d, 1H) 6.81 (s, 1H) 7.05-7.14 (m, 2H) 8.17-8.26 (m, 2H) 10.34 (br. s., 1H) 10.66-10.87 (m, 1H).

EXAMPLE 12

5-[2,4-Dihydroxy-6-(4-nitrophenoxy)phenyl]-N-(1-methyl-1,4'-bipiperidin-4-yl)isoxazole-3-carboxamide

[(I); (Z)—R=4-Nitrophenoxy, X=O, N=O, W=CH, $R_1=C_{12}H_{22}N_3O$]

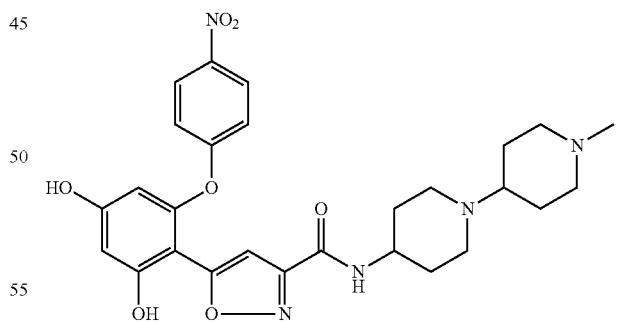

Operating as in Example 11 but employing 1-methyl-piperidin-4-one instead of cyclohexanone, the title compound was obtained in 46% yield.

$^1$H NMR (400 MHz, DMSO-$d_6$) δ ppm 1.39 (qd, 2H) 1.50 (qd, 2H) 1.59-1.73 (m, 4H) 1.80 (td, 2H) 2.12 (td, 2H) 2.11 (s, 3H) 2.76 (d, 2H) 2.82 (d, 2H) 3.59-3.73 (m, 1H) 5.98 (br. s., 1H) 6.37 (br. s., 1H) 6.86 (s, 1H) 7.08 (d, 2H) 8.21 (d, 2H) 8.45 (d, 1H).

EXAMPLE 13

5-[2,4-Dihydroxy-6-(4-nitrophenoxy)phenyl]-N-[1-(tetrahydro-2H-pyran-4-yl)piperidin-4-yl]isoxazole-3-carboxamide

[(I); (Z)—R=4-Nitrophenoxy, X=O, Y=N, W=CH, $R_1=C_{12}H_{22}N_3O$]

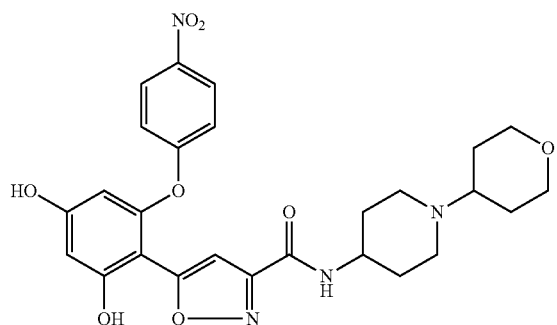 [SMILES: O=C(NC1CCN(C2CCOCC2)CC1)c1cc(-c2c(O)cc(O)cc2Oc2ccc([N+](=O)[O-])cc2)on1]

Operating as in Example 11, but employing tetrahydropyran-4-one instead of cyclohexanone, the title compound was obtained in 73% yield.

$^1$H NMR (400 MHz, DMSO-d$_6$) δ ppm 3.69 (br. s., 1H) 3.87 (dd, 2H) 6.10 (d, 1H) 6.46 (d, 1H) 6.80 (s, 1H) 7.00-7.17 (m, 2H) 8.13-8.29 (m, 2H) 8.52 (d, 1H) 10.30 (br. s., 1H) 10.72 (br. s., 1H).

EXAMPLE 14

N-[1-(4,4-Difluorocyclohexyl)piperidin-4-yl]-5-[2,4-dihydroxy-6-(4-nitrophenoxy)phenyl]isoxazole-3-carboxamide

[(I); (Z)—R=4-Nitrophenoxy, X=O, Y=N, W=CH, $R_1=C_{12}H_{19}F_2N_2O$]

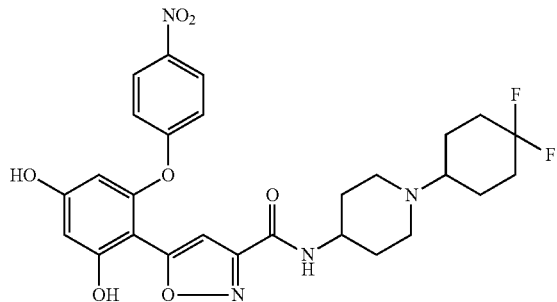 [SMILES: O=C(NC1CCN(C2CCC(F)(F)CC2)CC1)c1cc(-c2c(O)cc(O)cc2Oc2ccc([N+](=O)[O-])cc2)on1]

Operating as in Example 11, but employing 4,4-difluorocyclohexanone instead of cyclohexanone, the title compound was obtained in 57% yield.

$^1$H NMR (400 MHz, DMSO-d$_6$) δ ppm 2.18 (t, 2H) 2.43 (t, 1H) 2.81 (d, 2H) 3.58-3.78 (m, 1H) 6.10 (d, 1H) 6.45 (d, 1H) 6.80 (s, 1H) 7.09 (d, 2H) 8.21 (d, 2H) 8.51 (d, Hz, 1H) 10.30 (br. s., 1H) 10.72 (br. s., 1H).

EXAMPLE 15

5-[2,4-Dihydroxy-6-(4-nitrophenoxy)phenyl]-N-[1-(1,4-dioxaspiro[4.5]dec-8-yl)piperidin-4-yl]isoxazole-3-carboxamide

[(I); (Z)—R=4-Nitrophenoxy, X=O, Y=N, W=CH, $R_1=C_{14}H_{23}N_2O_3$]

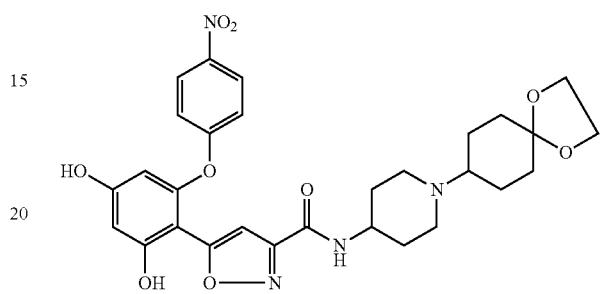

Operating as in Example 11, but employing 1,4-dioxaspiro-[4,5]decan-8-one instead of cyclohexanone, the title compound was obtained in 46% yield.

$^1$H NMR (400 MHz, DMSO-d$_6$) δ ppm 1.93 (t, 2H) 2.36 (t, 2H) 3.95 (s, 6H) 4.45 (d, 1H) 6.10 (d, 1H) 6.46 (d, 1H) 6.81 (s, 1H) 7.09 (d, 2H) 8.22 (d, 2H) 10.32 (s, 1H) 10.73 (br. s., 1H).

EXAMPLE 16

(Trans) N-{1-[4-(Acetylamino)cyclohexyl]piperidin-4-yl}-5-[2,4-dihydroxy-6-(4-nitrophenoxy)phenyl]isoxazole-3-carboxamide

[(I); (Z)—R=4-Nitrophenoxy, X=O, Y=N, W=CH, $R_1=C_{14}H_{23}N_3O_2$]

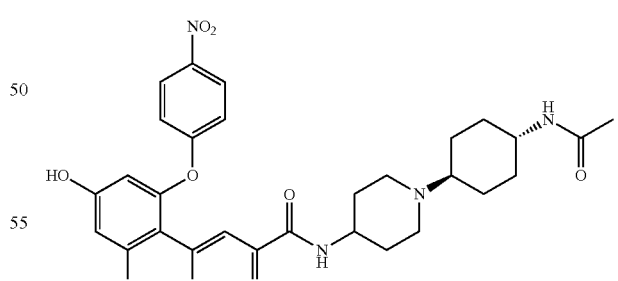

Operating as in Example 11, but employing 4-acetamidocyclohexanone instead of cyclohexanone, the title compound was obtained in 18% yield.

$^1$H NMR (400 MHz, DMSO-d$_6$) δ ppm 3.60-3.89 (m, 2H) 6.10 (d, 1H) 6.47 (d, Hz, 1H) 6.80 (s, 1H) 7.01-7.17 (m, 2H) 7.68 (d, 1H) 8.13-8.29 (m, 2H) 8.56 (br. s., 1H) 10.33 (br. s., 1H) 10.74 (br. s., 1H).

EXAMPLE 17

(Cis) N-{1-[4-(Acetylamino)cyclohexyl]piperidin-4-yl}-5-[2,4-dihydroxy-6-(4-nitrophenoxy)phenyl]isoxazole-3-carboxamide

[(I); (Z)—R=4-Nitrophenoxy, X=O, Y=N, W=CH, R₁=C₁₄H₂₃N₃O₂]

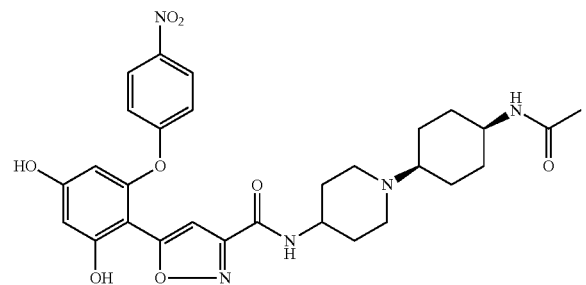 [SMILES: CC(=O)N[C@H]1CC[C@@H](N2CCC(NC(=O)c3cc(-c4c(O)cc(O)cc4Oc4ccc([N+](=O)[O-])cc4)on3)CC2)CC1]

The mother liquor of Example 16 was carefully chromatographed over silica gel eluting with hexane/ethyl acetate 4/1 then 4/2 to provide, after crystallization from acetone the title compound in 11% yield.

$^1$H NMR (400 MHz, DMSO-d$_6$) δ ppm 6.10 (d, 1H) 6.46 (d, 1H) 6.80 (s, 1H) 7.05-7.15 (m, 2H) 7.70 (d, 2H) 8.12-8.30 (m, 2H) 8.54 (br. s., 1H) 10.32 (s, 1H) 10.73 (br. s., 1H).

EXAMPLE 18

5-[2,4-Dihydroxy-6-(4-nitrophenoxy)phenyl]-N-[1-(propan-2-yl)piperidin-4-yl]isoxazole-3-carboxamide

[(I); (Z)—R=4-Nitrophenoxy, X=O, Y=N, W=CH, R₁=C₉H₁₇N₂O]

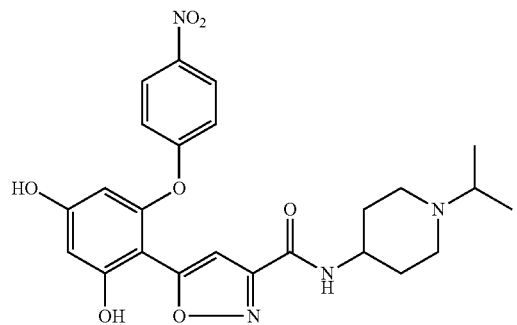 [SMILES: CC(C)N1CCC(NC(=O)c2cc(-c3c(O)cc(O)cc3Oc3ccc([N+](=O)[O-])cc3)on2)CC1]

Operating as in Example 11 but employing acetone instead of cyclohexanone, the title compound was obtained in 64% yield.

$^1$H NMR (400 MHz, DMSO-d$_6$) δ ppm 6.11 (d, 1H) 6.49 (d, 1H) 6.81 (s, 1H) 7.05-7.13 (m, 2H) 8.15-8.26 (m, 2H) 8.63 (br. s., 1H) 10.35 (br. s., 1H) 10.77 (br. s., 1H).

EXAMPLE 19

N-[1-(Cylohexylmethyl)piperidin-4-yl]-5-[2,4-dihydroxy-6-(4-nitrophenoxy)phenyl]isoxazole-3-carboxamide

[(I); (Z)—R=4-Nitrophenoxy, X=O, Y=N, W=CH, R₁=C₁₃H₂₃N₂O]

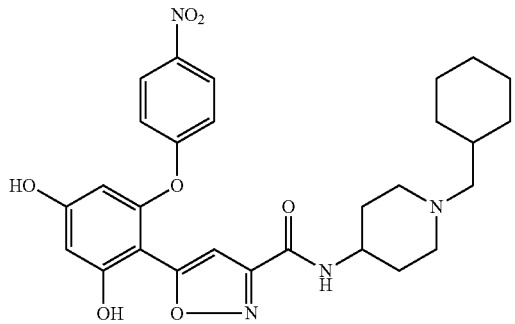 [SMILES: O=C(NC1CCN(CC2CCCCC2)CC1)c1cc(-c2c(O)cc(O)cc2Oc2ccc([N+](=O)[O-])cc2)on1]

Operating as in Example 11, but employing cyclohexancarbaldehyde instead of cyclohexanone, the title compound was obtained in 73% yield.

$^1$H NMR (400 Hz, DMSO-d$_6$) δ ppm 6.11 (d, 1H) 6.48 (d, 1H) 6.82 (s, 1H) 7.10 (d, 2H) 8.22 (d, 2H) 10.34 (s, 1H) 10.76 (s, 1H).

EXAMPLE 20

5-[2,4-Dihydroxy-6-(4-nitrophenoxy)phenyl]-N-{1-[trans-4-(trifluoromethyl)cyclohexyl]piperidin-4-yl}isoxazole-3-carboxamide

[(I); (Z)—R=4-Nitrophenoxy, X=O, Y=N, W=CH, R₁=C₁₃H₂₀F₃N₂O]

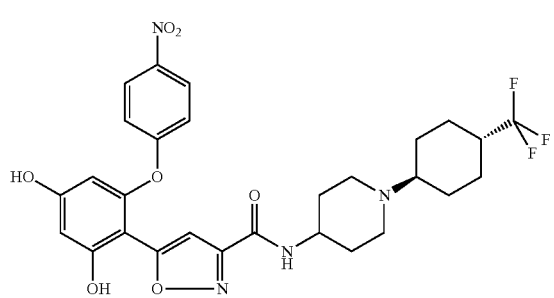 [SMILES: O=C(NC1CCN([C@H]2CC[C@H](C(F)(F)F)CC2)CC1)c1cc(-c2c(O)cc(O)cc2Oc2ccc([N+](=O)[O-])cc2)on1]

Operating as in Example 11, but employing 4-trifluoromethyl-cyclohexanone instead of cyclohexanone, the title compound was obtained in 57% yield.

$^1$H NMR (400 MHz, DMSO-d$_6$) δ ppm 3.70 (br. s., 1H) 6.05-6.13 (m, 1H) 6.46 (d, 1H) 7.05-7.16 (m, 2H) 8.22 (d, 2H) 8.50 (d, 1H) 10.30 (br. s., 1H) 10.71 (br. s., 1H).

EXAMPLE 21

N-(1-Cyclopentylpiperidin-4-yl)-5-[2,4-dihydroxy-6-(4-nitrophenoxy)phenyl]isoxazole-3-carboxamide

[(I); (Z)—R=4-Nitrophenoxy, X=O, Y=N, W=CH, $R_1=C_{11}H_{16}N_2O$]

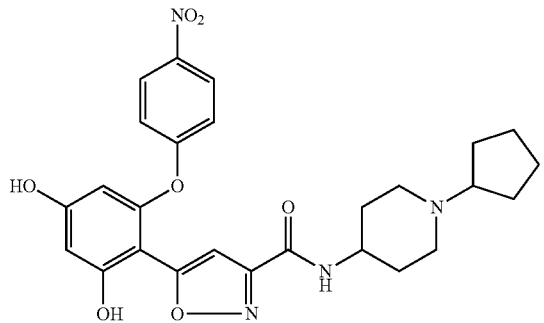 [SMILES: O=C(NC1CCN(C2CCCC2)CC1)c1cc(-c2c(O)cc(O)cc2Oc2ccc([N+](=O)[O-])cc2)on1]

Operating as in Example 11, but employing cyclopentanone instead of cyclohexanone, the title compound was obtained in 71% yield.

$^1$H NMR (400 MHz, DMSO-$d_6$) δ ppm 1.17-1.82 (m, 11H) 1.97 (m, 1H) 2.94 (m, 2H) 3.57-3.84 (m, 1H) 6.10 (d, 1H) 6.46 (d, 1H) 6.80 (s, 1H) 6.99-7.21 (m, 2H) 8.02-8.31 (m, 2H) 8.53 (d, 1H) 10.31 (br. s., 1H) 10.70 (br. s., 1H)

EXAMPLE 22

N-(1-Cycloheptylpiperidin-4-yl)-5-[2,4-dihydroxy-6-(4-nitrophenoxy)phenyl]isoxazole-3-carboxamide

[(I); (Z)—R=4-Nitrophenoxy, X=O, Y=N, W=CH, $R_1=C_{13}H_{23}N_2O$]

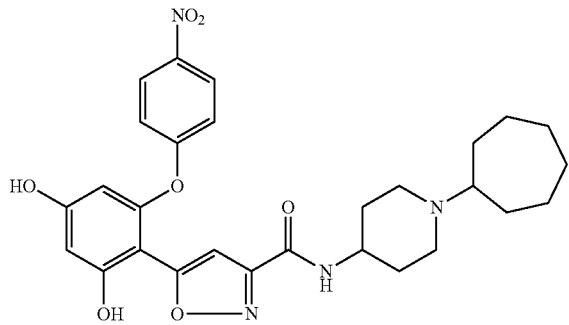 [SMILES: O=C(NC1CCN(C2CCCCCC2)CC1)c1cc(-c2c(O)cc(O)cc2Oc2ccc([N+](=O)[O-])cc2)on1]

Operating as in Example 11, but employing cycloheptanone instead of cyclohexanone, the title compound was obtained in 38% yield.

$^1$H NMR (400 MHz, DMSO-$d_6$) δ ppm 1.24-1.88 (m, 16H) 2.05-2.30 (m, 1H) 2.63-3.01 (m, 2H) 3.71 (br. s., 1H) 6.10 (d, 1H) 6.46 (d, 1H) 6.80 (s, 1H) 7.00-7.20 (m, 2H) 8.12-8.29 (m, 2H) 8.54 (br. s., 1H) 10.32 (br. s., 1H) 10.73 (br. s., 1H)

EXAMPLE 23

N-(1-Benzylpiperidin-4-yl)-5-[2,4-dihydroxy-6-(4-nitrophenoxy)phenyl]isoxazole-3-carboxamide

[(I); (Z)—R=4-Nitrophenoxy, X=O, Y=N, W=CH, $R_1=C_{13}H_{17}N_2O$]

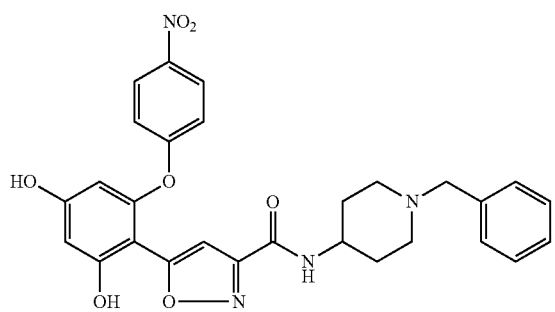 [SMILES: O=C(NC1CCN(Cc2ccccc2)CC1)c1cc(-c2c(O)cc(O)cc2Oc2ccc([N+](=O)[O-])cc2)on1]

Operating as in Example 11, but employing benzaldehyde instead of cyclohexanone, the title compound was obtained in 64% yield.

$^1$H NMR (400 MHz, DMSO-$d_6$) δ ppm 6.10 (d, 1H) 6.47 (d, 1H) 6.80 (s, 1H) 7.09 (d, 2H) 8.21 (d, 2H) 10.33 (s, 1H) 10.74 (br. s., 1H)

EXAMPLE 24

5-{2-[4-(Dimethylamino)phenoxy]-4,6-dihydroxyphenyl}-N-(piperidin-4-yl)isoxazole-3-carboxamide Dihydrochloride

[(I); (Z)—R=4-(Dimethylamino)phenoxy, X=O, Y=N, W=CH, $R_1=C_6H_{11}N_2O$]

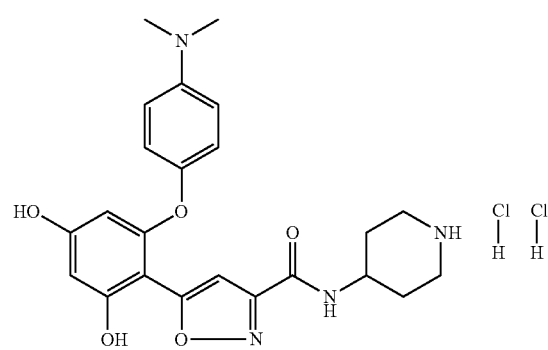

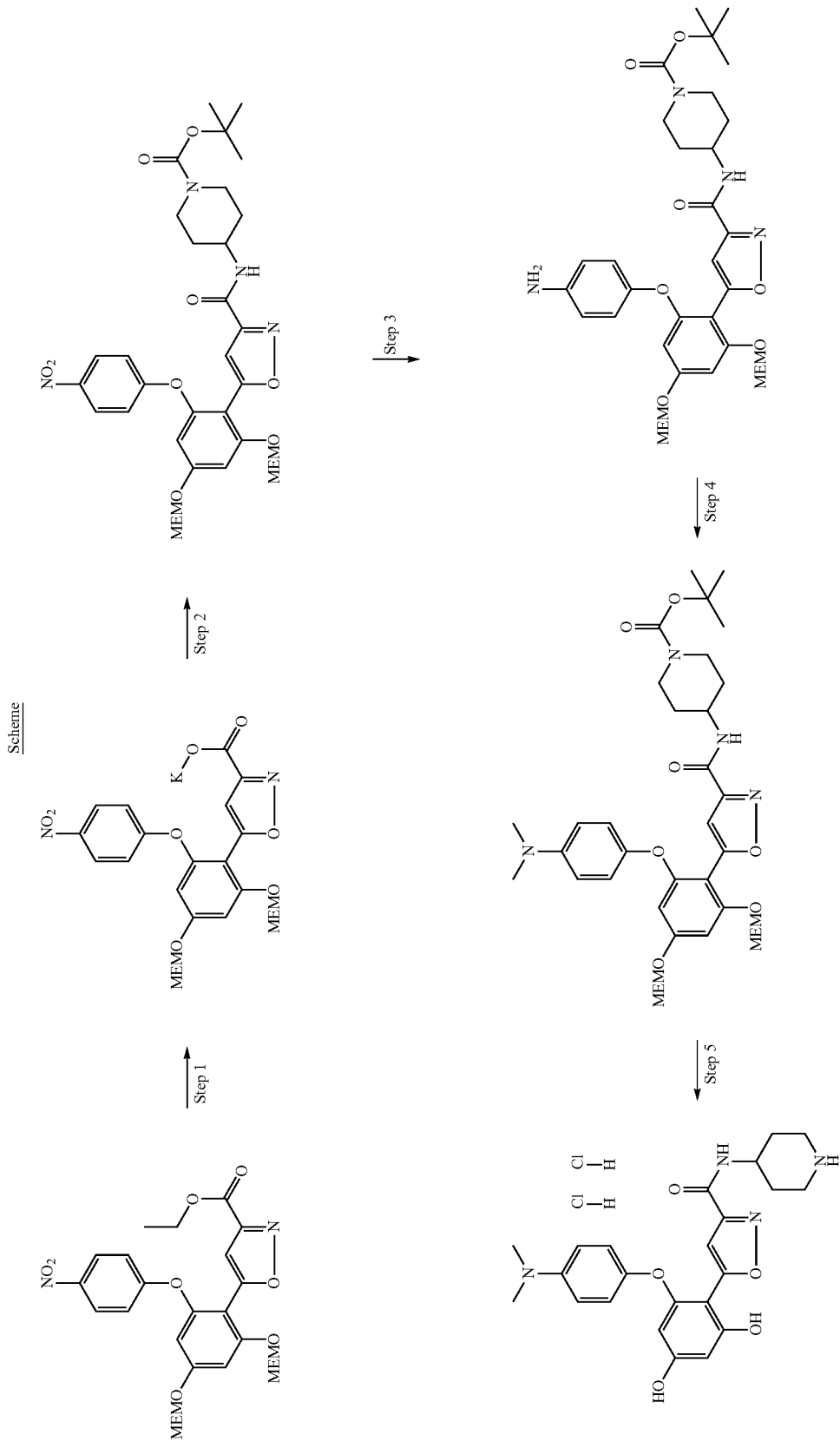

Step 1

Potassium 5-{2,4-bis[(2-methoxyethoxy)methoxy]-6-(4-nitrophenoxy)phenyl}isoxazole-3-carboxylate To a stirred solution of 5-{2,4-bis[(2-methoxyethoxy)methoxy]-6-(4-nitrophenoxy)phenyl}isoxazole-3-carboxylic acid ethyl ester (15.6 g., 27.7 mmol) in ethanol (75 mL) was added a solution of 1 M KOH (55.5 mL, 55 mmol, 2 eq.) in ethanol at room temperature. After stirring overnight, the precipitate was collected and washed with a small volume of ethanol, then with ether to provide the title compound (12.3 g, 77% yield).

Step 2

Tert-butyl-4-{[(5-{2,4-Bis[(2-methoxyethoxy)methoxy]-6-(4-nitrophenoxy)phenyl}isoxazol-3-yl)carbonyl]amino}piperidine-1-carboxylate To a stirred solution of potassium 5-{2,4-bis[(2-methoxyethoxy)methoxy]-6-(4-nitrophenoxy)phenyl}isoxazole-3-carboxylate (3.8 g, 6.6 mol) in DMF (50 mL) was added portion wise TBTU (2.34 g, 7.3 mmol, 1.1 eq.) at 0° C. After stirring for 20 minutes, a solution of tert-butyl 4-aminopiperidine-1-carboxylate (1.6 g, 8 mmol, 1.2 eq.) in DMF (25 mL) was added and the reaction was set-aside at room temperature overnight. The reaction mixture was taken up in ethyl acetate and thoroughly washed with water then with brine. After drying over $Na_2SO_4$, the solvent was removed and the residue was carefully chromatographed over silica gel eluting with a mixture of ethyl acetate/hexane 4/7 to provide the title compound (3.1 g, 65% yield).

$^1$H NMR (400 MHz, DMSO-$d_6$) δ ppm 1.31-1.46 (m, 12H) 1.62-1.73 (m, 2H) 2.77 (br. s., 1H) 3.18 (s, 3H) 3.19 (s, 3H) 3.38-3.49 (m, 4H) 3.58-3.74 (m, 4H) 3.90 (m, 2H) 5.28 (s, 2H) 5.36 (s, 2H) 6.61 (d, 1H) 6.83 (s, 1H) 6.89 (d, 1H) 7.01-7.20 (m, 2H) 8.13-8.24 (m, 2H) 8.61 (d, 1H).

Step 3

Tert-butyl-4-{[(5-{2,4-Bis[(2-methoxyethoxy)methoxy]-6-(4-aminophenoxy)phenyl}isoxazol-3-yl)carbonyl]amino}piperidine-1-carboxylate To a stirred solution of tert-butyl 4-{[(5-{2,4-bis[(2-methoxyethoxy)methoxy]-6-(4-nitrophenoxy)phenyl}isoxazol-3-yl)carbonyl]amino}piperidine-1-carboxylate (5.3 g, 7.4 mmol) in a mixture of dioxane (100 mL) and water (20 mL) were added portion wise zinc powder (1 g, 14.8 mmol, 2 eq.) and ammonium chloride (3.9 g, 74 mmol, 10 eq.) at 100° C. After stirring for 30 minutes, the reaction mixture was cooled and diluted with ethyl acetate. After washing with 1 M $Na_2CO_3$ solution, the organic phase was dried over $Na_2SO_4$ and the solvent removed. The crude product was filtered over a small pad of silica gel eluting with hexane/ethyl acetate 3/1 to provide the title compound (4.38 g, 86% yield).

$^1$H NMR (400 MHz, DMSO-$d_6$) δ ppm 1.30-1.45 (m, 12H) 1.62-1.74 (m, 2H) 2.76 (br. s., 1H) 3.17 (s, 3H) 3.19 (s, 3H) 3.37-3.48 (m, 4H) 3.57-3.75 (m, 4H) 3.91 (m, 2H) 5.29 (s, 2H) 5.37 (s, 2H) 6.62 (d, 1H) 6.81 (s, 1H) 6.85 (d, 1H) 7.01-7.18 (m, 2H) 8.11-8.21 (m, 2H) 8.60 (d, 1H).

Step 4

Tert-butyl-4-{[(5-{2,4-Bis[(2-methoxyethoxy)methoxy]-6-(4-dimethylaminophenoxy)phenyl}isoxazol-3-yl)carbonyl]amino}piperidine-1-carboxylate To a stirred solution of tert-butyl 4-{[(5-{2,4-bis[(2-methoxyethoxy)methoxy]-6-(4-aminophenoxy)phenyl}isoxazol-3-yl)carbonyl]amino}piperidine-1-carboxylate (4.55 g, 6.6 mmol) and 37% HCHO solution (4 mL, 50 mmol, 3.7 eq.) in a mixture of DMF (25 mL) and AcOH (15 mL) was added portion wise $(CH_3)_4NBH(OAc)_3$ (8.65 g, 33 mmol, 2.5 eq.) at room temperature. After stirring for 2.5 hours, the solution was diluted with ethyl acetate and thoroughly washed with 1 M $NaHCO_3$ solution. After drying over $Na_2SO_4$, the solvent was removed and the residue was chromatographed on silica gel eluting with hexane/ethyl acetate 6/4 to provide the title compound (2.87 g, 34% yield).

$^1$H NMR (400 MHz, DMSO-$d_6$) δ ppm 1.31-1.44 (m, 12H) 1.61-1.75 (m, 2H) 2.77 (br. s., 1H) 2.93 (s, 6H) 3.17 (s, 3H) 3.18 (s, 3H) 3.38-3.49 (m, 4H) 3.55-3.72 (m, 4H) 3.91 (m, 2H) 5.28 (s, 2H) 5.36 (s, 2H) 6.63 (d, 1H) 6.82 (s, 1H) 6.86 (d, 1H) 7.08-7.19 (m, 2H) 8.11-8.21 (m, 2H) 8.62 (d, 1H).

Step 5

5-{2-[4-(Dimethylamino)phenoxy]-4,6-dihydroxyphenyl}-N-(piperidin-4-yl)isoxazole-3-carboxamide Dihydrochloride

[(I); (Z)—R=4-(Dimethylamino)phenoxy, X=O, Y=N, W=CH, $R_1=C_6H_{11}N_2O$]

To a stirred solution of tert-butyl 4-{[(5-{2,4-bis[(2-methoxyethoxy)methoxy]-6-(4-dimethylaminophenoxy)phenyl}isoxazol-3-yl)carbonyl]amino}piperidine-1-carboxylate (3.57 g, 5 mmol) in ethanol (30 mL) was added 4 M HCl in dioxane solution (15 mL). After heating for 1 h at 50° C., the solution was evaporated to small volume. After cooling, the precipitate was collected and washed with a small volume of cold ethanol and dried to furnish the title compound (1.46 g, 66% yield).

$^1$H NMR (400 MHz, DMSO-$d_6$) δ ppm 1.94-2.11 (m, 6H) 3.04 (s, 6H) 3.06-3.13 (m, 2H) 3.34-3.37 (m, 2H) 3.94-3.97 (s, 1H) 6.25 (d, 1H), 6.41 (d, 1H) 6.95 (m, 2H) 7.10 (m, 1H) 7.26 (1H, s) 7.43 (dd, 2H) 9.45 (m, 4H).

EXAMPLE 25

N-(1-Cyclohexylpiperidin-4-yl)-5-{2-[4-(dimethylamino)phenoxy]-4,6-dihydroxyphenyl}isoxazole-3-carboxamide

[(I); (Z)—R=4-(Dimethylamino)phenoxy, X=O, Y=N, W=CH, $R_1=C_{12}H_{21}N_2O$]

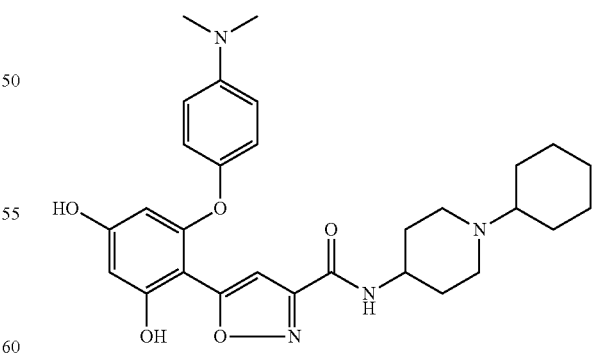

Operating as in Example 11, but employing 5-[3,5-dihydroxy-2-(4-(dimethylamino)phenoxy)phenyl]-N-(piperidin-4-yl)isoxazole-3-carboxamide dihydrochloride instead of 5-[3,5-dihydroxy-2-(4-nitrophenoxy)phenyl]-N-(piperidin-4-yl)isoxazole-3-carboxamide hydrochloride, the title compound was obtained in 45% yield.

¹H NMR (400 MHz, DMSO-d$_6$) δ ppm 2.87 (s, 6H) 5.66 (d, 1H) 6.15 (d, 1H) 6.72-6.77 (m, 2H) 6.78 (s, 1H) 6.87-6.93 (m, 2H) 8.84 (br. s., 1H) 9.82 (s, 1H) 10.22 (s, 1H).

EXAMPLE 26

N-(1-Cyclohexylpiperidin-4-yl)-5-{2-[4-(dimethylamino)phenoxy]-4,6-dihydroxyphenyl}isoxazole-3-carboxamide 1,3-dioxolane

[(I); (Z)—R=4-(Dimethylamino)phenoxy, X=O, Y=N, W=CH, R$_1$=C$_{13}$H$_{22}$N$_2$O$_3$]

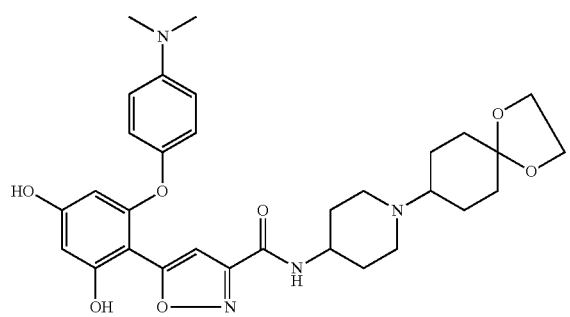 [SMILES: CN(C)c1ccc(Oc2cc(O)cc(O)c2-c2cc(C(=O)NC3CCN(C4CCC5(CC4)OCCO5)CC3)no2)cc1]

Operating as in Example 25, but employing 1,4-dioxaspiro[4,5]decan-8-one instead of cyclohexanone, the title compound was obtained in 72% yield.

¹H NMR (400 MHz, DMSO-d$_6$) δ ppm 2.65 (br. s., 5H) 2.87 (s, 6H) 3.79-3.93 (m, 5H) 5.65 (d, 1H) 6.15 (d, 1H) 6.74 (d, 2H) 6.78 (s, 1H) 6.90 (d, 2H) 8.79 (br. s., 1H) 9.83 (s, 1H) 10.23 (s, 1H).

EXAMPLE 27

5-{2-[4-(Dimethylamino)phenoxy]-4,6-dihydroxyphenyl}-N-[1-(1,5-dioxaspiro[5.5]undec-9-yl)piperidin-4-yl]isoxazole-3-carboxamide

[(I); (Z)—R=4-(Dimethylamino)phenoxy, X=O, Y=N, W=CH, R$_1$=C$_{14}$H$_{24}$N$_2$O$_3$]

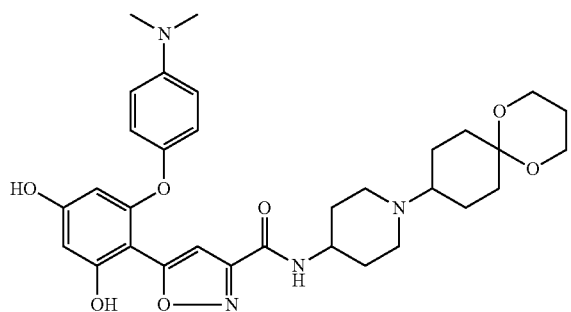 [SMILES: CN(C)c1ccc(Oc2cc(O)cc(O)c2-c2cc(C(=O)NC3CCN(C4CCC5(CC4)OCCCO5)CC3)no2)cc1]

Operating as in Example 25, but employing 1,5-dioxaspiro[5.5]undecan-9-one instead of cyclohexanone, the title compound was obtained in 58% yield.

¹H NMR (400 MHz, DMSO-d$_6$) δ ppm 2.87 (s, 6H) 3.79 (dt, 4H) 5.65 (d, 1H) 6.14 (d, 1H) 6.71-6.76 (m, 2H) 6.77 (s, 1H) 6.83-6.98 (m, 2H) 8.60 (br. s., 1H) 9.81 (s, 1H) 10.21 (s, 1H).

EXAMPLE 28

5-{2-[4-(Dimethylamino)phenoxy]-4,6-dihydroxyphenyl}-N-[1-(3,3-dimethyl-1,5-dioxaspiro[5.5]undec-9-yl)piperidin-4-yl]isoxazole-3-carboxamide

[(I); (Z)—R=4-(Dimethylamino)phenoxy, X=O, Y=N, W=CH, R$_1$=C$_{16}$H$_{28}$N$_2$O$_3$]

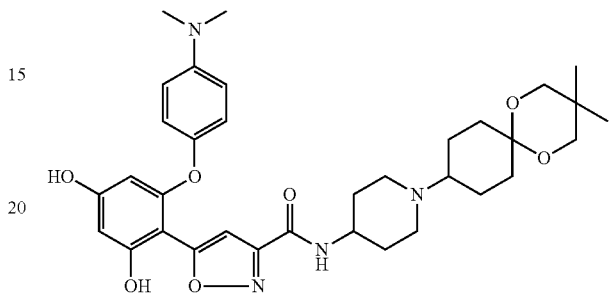

Operating as in Example 25, but employing 3,3-dimethyl-1,5-dioxa-spiro[5,5]undecan-9-one instead of cyclohexanone, the title compound was obtained in 63% yield.

¹H NMR (400 MHz, DMSO-d$_6$) δ ppm 0.88 (s, 6H) 1.19-1.32 (m, 2H) 1.41 (br. s., 2H) 1.58 (br. s., 3H) 1.75 (br. s., 2H) 2.19 (m, 6H) 2.82 (br. s., 2H) 2.87 (s, 6H) 3.38-3.44 (m, 4H) 3.73 (br. s., 1H) 5.65 (d, 1H) 6.14 (d, 1H) 6.65-6.80 (m, 3H) 6.85-6.97 (m, 2H) 8.52 (br. s., 1H) 9.80 (s, 1H) 10.19 (s, 1H).

EXAMPLE 29

5-{2-[4-(Dimethylamino)phenoxy]-4,6-dihydroxyphenyl}-N-[1-(7,12-dioxaspiro[5.6]dodec-3-yl)piperidin-4-yl]isoxazole-3-carboxamide

[(I); (Z)—R=4-(Dimethylamino)phenoxy, X=O, Y=N, W=CH, R$_1$=C$_{15}$H$_{26}$N$_2$O$_3$]

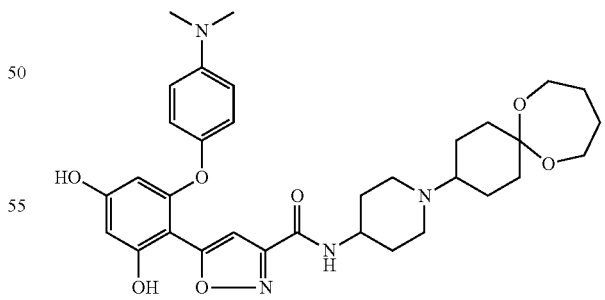

Operating as in Example 25, but employing 7,12-dioxaspiro[5.6]dodecan-3-one instead of cyclohexanone, the title compound was obtained in 46% yield.

¹H NMR (400 MHz, DMSO-d$_6$) δ ppm 2.08-2.42 (m, 3H) 2.87 (s, 8H) 3.58 (br. s., 4H) 3.74 (br. s., 1H) 5.65 (d, 1H) 6.14 (d, 1H) 6.70-6.76 (m, 2H) 6.77 (s, 1H) 6.87-6.93 (m, 2H) 8.55 (br. s., 1H) 9.81 (br. s., 1H) 10.20 (br. s., 1H).

EXAMPLE 30

5-{2-[4-(Dimethylamino)phenoxy]-4,6-dihydroxyphenyl}-N-{1-[(2R,3S)-2,3-dimethyl-1,4-dioxaspiro[4.5]dec-8-yl]piperidin-4-yl}isoxazole-3-carboxamide

[(I); (Z)—R=4-(Dimethylamino)phenoxy, X=O, Y=N, W=CH, $R_1=C_{16}H_{27}N_2O_3$]

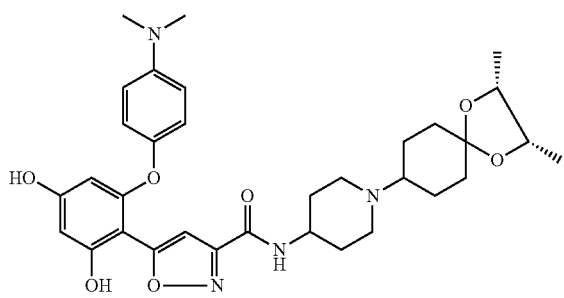 [SMILES: C[C@@H]1OC2(CCC(N3CCC(NC(=O)c4cc(-c5c(O)cc(O)cc5Oc5ccc(N(C)C)cc5)on4)CC3)CC2)O[C@@H]1C]

Operating as in Example 25, but employing (2S,3R)-2,3-dimethyl-1,4-dioxa-spiro[4.5]decan-8-one instead of cyclohexanone, the title compound was obtained in 53% yield.

$^1$H NMR (401 MHz, DMSO-$d_6$) δ ppm 1.04 (d, 3H) 1.07 (d, 3H) 2.87 (s, 6H) 4.05 (br. s., 1H) 4.15-4.27 (m, 2H) 5.65 (d, 1H) 6.15 (d, 1H) 6.70-6.78 (m, 2H) 6.79 (s, 1H) 6.86-6.95 (m, 2H) 8.88 (br. s., 1H) 9.41 (br. s., 1H) 9.83 (s, 1H) 10.22 (s, 1H).

EXAMPLE 31

N-[1-(4,4-Difluorocyclohexyl)piperidin-4-yl]-5-{2-[4-(dimethylamino)phenoxy]-4,6-dihydroxyphenyl}isoxazole-3-carboxamide

[(I); (Z)—R=4-(Dimethylamino)phenoxy, X=O, Y=N, W=CH, $R_1=C_{14}H_{22}F_2N_2O_3$]

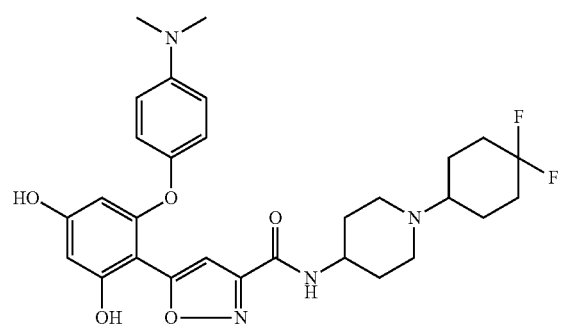 [SMILES: CN(C)c1ccc(Oc2cc(O)cc(O)c2-c2cc(C(=O)NC3CCN(C4CCC(F)(F)CC4)CC3)no2)cc1]

Operating as in Example 25, but employing 4,4-difluorocyclohexanone instead of cyclohexanone, the title compound was obtained in 37% yield.

$^1$H NMR (400 MHz, DMSO-$d_6$) δ ppm 1.53 (m, 4H) 1.73 (br. s., 6H) 2.01 (td, 2H) 2.20 (t, 2H) 2.44 (td, 1H) 2.83 (m, 2H) 2.87 (s, 6H) 3.71 (br. s., 1H) 5.65 (d, 1H) 6.14 (d, 1H) 6.71-6.76 (m, 2H) 6.77 (s, 1H) 6.85-6.94 (m, 2H) 8.51 (d, 1H) 9.80 (s, 1H) 10.19 (s, 1H).

EXAMPLE 32

N-[1-(Cyclohexylmethyl)piperidin-4-yl]-5-{2-[4-(dimethylamino)phenoxy]-4,6-dihydroxyphenyl}isoxazole-3-carboxamide

[(I); (Z)—R=4-(Dimethylamino)phenoxy, X=O, Y=N, W=CH, $R_1=C_{18}H_{32}N_3O$]

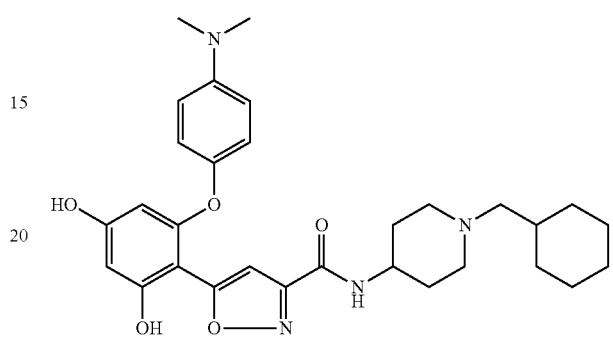

Operating as in Example 25, but employing cyclohexancarbaldehyde instead of cyclohexanone, the title compound was obtained in 44% yield.

$^1$H NMR (400 MHz, DMSO-$d_6$) δ ppm 2.87 (s, 6H) 5.65 (d, 1H) 6.14 (d, 1H) 6.72-6.77 (m, 2H) 6.78 (s, 1H) 6.86-6.93 (m, 2H) 9.82 (s, 1H) 10.21 (s, 1H).

EXAMPLE 33

N-(1-Benzylpiperidin-4-yl)-5-{2-[4-(dimethylamino)phenoxy]-4,6-dihydroxyphenyl}isoxazole-3-carboxamide

[(I); (Z)—R=4-(Dimethylamino)phenoxy, X=O, Y=N, W=CH, $R_1=C_{18}H_{26}N_3O$]

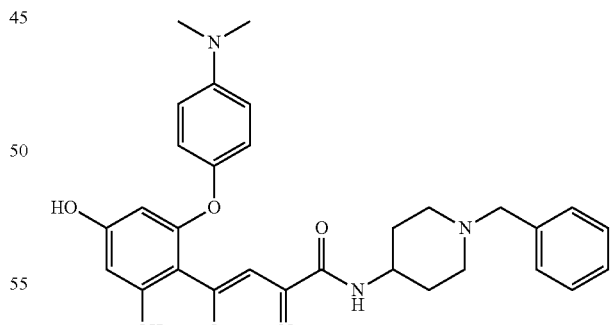

Operating as in Example 25, but employing benzaldehyde instead of cyclohexanone, the title compound was obtained in 56% yield.

$^1$H NMR (400 MHz, DMSO-$d_6$) δ ppm 1.63 (br. s., 2H) 1.74 (br. s., 2H) 2.00 (br. s., 2H) 2.82 (br. s., 2H) 2.87 (s, 6H) 3.77 (br. s., 1H) 5.65 (d, 1H) 6.14 (d, 1H) 6.74 (d, 2H) 6.77 (s, 1H) 6.90 (d, 2H) 7.32 (br. s., 5H) 8.55 (br. s., 1H) 9.81 (s, 1H) 10.21 (s, 1H).

EXAMPLE 34

[4,4,4-Trifluorobutyl)piperidin-4-yl]isoxazole-3-carboxamide

[(I); (Z)—R=4-Nitrophenoxy, X=O, Y=N, W=CH, $R_1=C_{10}H_{16}F_3N_2O$]

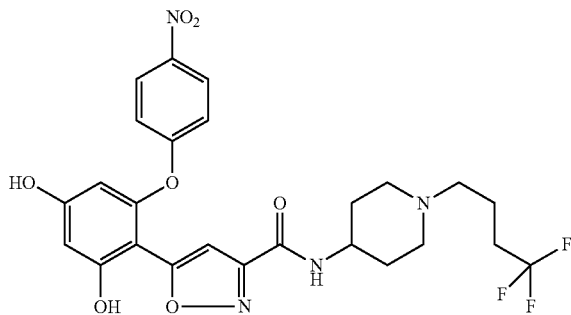 [SMILES: O=C(NC1CCN(CCCC(F)(F)F)CC1)c1cc(-c2c(O)cc(O)cc2Oc2ccc([N+](=O)[O-])cc2)on1]

A stirred solution of 5-[3,5-dihydroxy-2-(4-nitrophenoxy)phenyl]-N-(piperidin-4-yl)isoxazole-3-carboxamide hydrochloride (0.32 g, 0.8 mmol), DIPEA (0.28 g, 2.4 mmol, 3 eq.) and 4-bromo-1,1,1-trifluoro-butane (0.17 g, 0.9 mol, 1.1 eq.) in DMF (15 mL) was heated at 65° C. for 4 hours. The solution was taken up in ethyl acetate and thoroughly washed with brine then dried over $Na_2SO_4$. After removal of the solvent, the residue was crystallised twice from diethylether to afford the title compound (0.19 g, 43% yield).

$^1$H NMR (400 MHz, DMSO-$d_6$) δ ppm 1.55 (qd, 2H) 1.61 (quin, 2H) 1.69 (dq, 2H) 1.94 (td, 2H) 2.15-2.28 (m, 2H) 2.31 (t, 2H) 2.80 (d, 2H) 3.69 (m, 1H) 6.10 (d, 1H) 6.45 (d, 1H) 6.80 (s, 1H) 7.10 (d, 2H) 8.22 (d, 2H) 8.51 (d, 1H) 10.30 (br. s., 1H) 10.72 (br. s., 1H).

EXAMPLE 35

4-[({5-[2,4-Dihydroxy-6-(4-nitrophenoxy)phenyl]isoxazol-3-yl}carbonyl)amino]-1-[3-(dimethylamino)propyl]piperidinium

[(I); (Z)—R=4-Nitrophenoxy, X=O, Y=N, W=CH, $R_1=C_{11}H_{22}N_3O$]

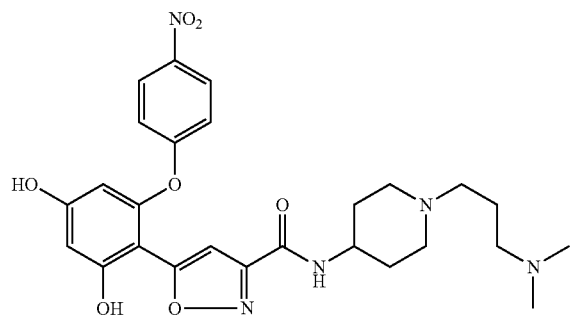 [SMILES: CN(C)CCCN1CCC(NC(=O)c2cc(-c3c(O)cc(O)cc3Oc3ccc([N+](=O)[O-])cc3)on2)CC1]

Operating as in Example 34, but employing (3-bromopropyl)-dimethyl-amine hydrochloride instead of 4-bromo-1,1,1-trifluoro-butane, the title compound was obtained in 37% yield.

$^1$H NMR (400 MHz, DMSO-$d_6$) δ ppm 1.42-1.61 (m, 4H) 1.68 (dd, 2H) 1.84-1.95 (m, 2H) 2.11 (s, 6H) 2.19 (t, 2H) 2.24 (t, 2H) 2.81 (d, 2H) 3.61-3.75 (m, 1H) 6.09 (d, 1H) 6.46 (d, 1H) 6.80 (s, 1H) 7.09 (d, 2H) 8.21 (d, 2H) 8.50 (d, 1H).

EXAMPLE 36

Tert-butyl(4-{-4-[({5-[2,4-dihydroxy-6-(4-nitrophenoxy)phenyl]isoxazol-3-yl}carbonyl)amino]piperidin-1-yl}butyl)carbamate

[(I); (Z)—R=4-Nitrophenoxy, X=O, Y=N, W=CH, $R_1=C_{15}H_{28}N_3O_3$]

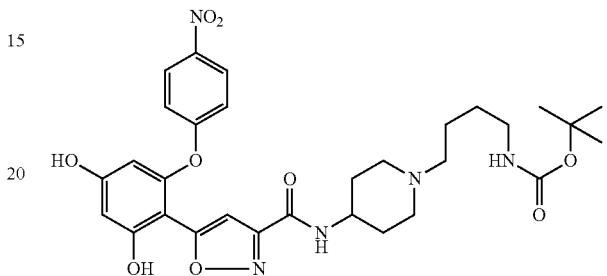

Operating as in Example 34, but employing (4-bromobutyl)-carbamic acid tert-butyl ester instead of 4-bromo-1,1,1-trifluoro-butane, the title compound was obtained in 42% yield.

$^1$H NMR (400 MHz, DMSO-$d_6$) δ ppm 1.37 (s, 9H) 1.48-1.61 (m, 2H) 1.70 (m, 2H) 1.92 (m, 2H) 2.24 (br. s., 2H) 2.83 (br. s., 2H) 2.86-2.95 (m, 2H) 3.69 (br. s., 1H) 6.10 (d, 1H) 6.46 (d, 1H) 6.78 (m, 1H) 6.80 (s, 1H) 6.98-7.18 (m, 2H) 8.01-8.33 (m, 2H) 8.53 (d, 1H) 10.31 (br. s., 1H) 10.72 (br. s., 1H).

EXAMPLE 37

N-[1-(4-aminobutyl)piperidin-4-yl]-5-[2,4-dihydroxy-6-(4-nitrophenoxy)phenyl]isoxazole-3-carboxamide Dihydrochloride

[(I); (Z)—R=4-Nitrophenoxy, X=O, Y=N, W=CH, $R_1=C_{10}H_{20}N_3O$]

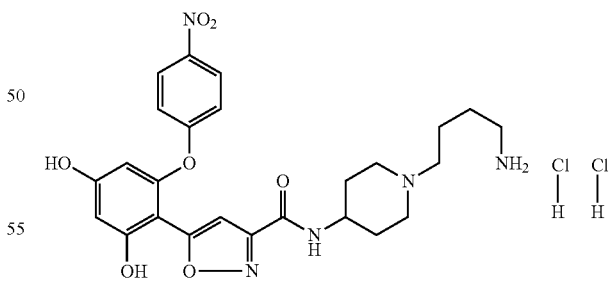

Operating as in Example 24 Step 5, but employing tert-butyl (4-{-4-[({5-[2,4-dihydroxy-6-(4-nitrophenoxy)phenyl]isoxazol-3-yl}carbonyl)amino]piperidin-1-yl}butyl)carbamate instead of tert-butyl 4-{[(5-{2,4-bis[(2-methoxyethoxy)methoxy]-6-(4-dimethylaminophenoxy)phenyl}isoxazol-3-yl)carbonyl]amino}piperidine-1-carboxylate, the title compound was obtained in 67% yield.

$^1$H NMR (400 MHz, DMSO-$d_6$) δ ppm 3.61 (td 1H) 3.99 (m, 1H) 6.12 (d, 1H) 6.49-6.51 (m, 1H) 6.83 (s, 1H) 7.05-7.15

(m, 2H) 7.88 (br. s., 3H) 8.13-8.30 (m, 2H) 8.89 (d, 1H) 9.99 (br. s., 1H) 10.35-10.39 (m, 1H) 10.79 (s, 1H).

EXAMPLE 38

Tert-butyl(3-{-4-[({5-[2,4-dihydroxy-6-(4-nitrophenoxy)phenyl]isoxazol-3-yl}carbonyl)amino]piperidin-1-yl}propyl)carbamate

[(I); (Z)—R=4-Nitrophenoxy, X=O, Y=N, W=CH, R₁=C₆H₁₈N₃O]

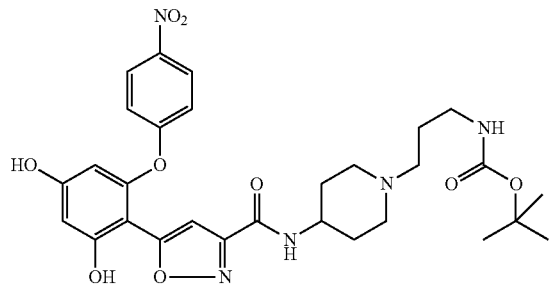 [SMILES: CC(C)(C)OC(=O)NCCCN1CCC(NC(=O)c2cc(-c3c(O)cc(O)cc3Oc3ccc([N+](=O)[O-])cc3)on2)CC1]

Operating as in Example 34, but employing (3-bromopropyl)-carbamic acid tert-butyl ester instead of 4-bromo-1,1,1-trifluoro-butane, the title compound was obtained in 57% yield.

¹H NMR (400 MHz, DMSO-d₆) δ ppm 6.10 (d, 1H) 6.46 (d, 1H) 6.77 (br. s., 1H) 7.01-7.23 (m, 2H) 8.12-8.29 (m, 2H) 8.54 (br. s., 1H) 10.30 (s, 1H) 10.72 (br. s., 1H).

EXAMPLE 39

N-[1-(3-Aminopropyl)piperidin-4-yl]-5-[2,4-dihydroxy-6-(4-nitrophenoxy)phenyl]isoxazole-3-carboxamide Dihydrochloride

[(I); (Z)—R=4-Nitrophenoxy, X=O, Y=N, W=CH, R₁=C₆H₁₈N₃O]

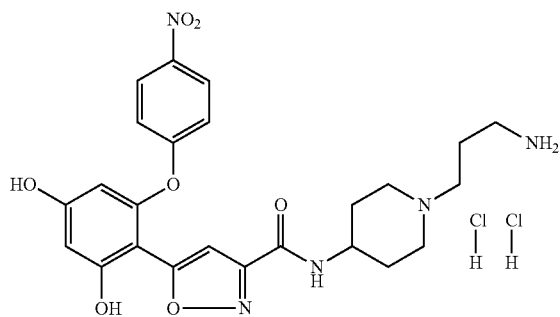

Operating as in Example 24 Step 5, but employing tert-butyl (3-{-4-[({5-[2,4-dihydroxy-6-(4-nitrophenoxy)phenyl]isoxazol-3-yl}carbonyl)amino]piperidin-1-yl}propyl) carbamate instead of tert-butyl (4-{4-[({5-[2,4-dihydroxy-6-(4-nitrophenoxy)phenyl]isoxazol-3-yl}carbonyl)amino] piperidin-1-yl}butyl)carbamate, the title compound was obtained in 55% yield.

¹H NMR (400 MHz, DMSO-d₆) δ ppm 1.40-1.73 (m, 6H) 1.89 (m, 2H) 2.27-2.35 (m, 2H) 2.72-2.87 (m, 4H) 6.06 (d, 1H) 6.44 (d, 1H) 6.77 (s, 1H) 6.96-7.14 (m, 2H) 8.13-8.21 (m, 2H) 8.27 (s, 2H) 8.47 (d, 1H).

EXAMPLE 40

5-{2,4-Dihydroxy-6-[4-(tetrahydro-2H-pyran-4-ylamino)phenoxy]phenyl}-N-(1-methylpiperidin-4-yl)isoxazole-3-carboxamide

[(I); (Z)—R=4-(Tetrahydro-2H-pyran-4-ylamino)phenoxy, X=O, Y=N, W=CH, R₁=C₆H₁₃N₂O]

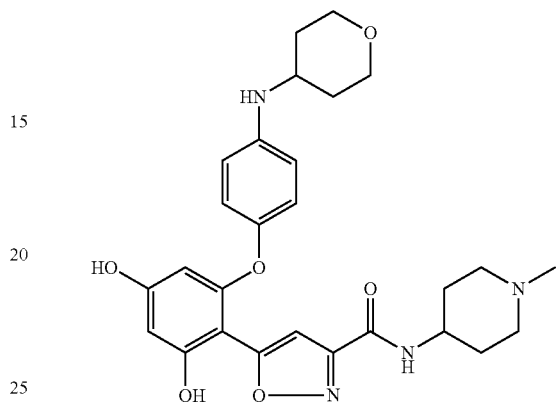

Operating as in Example 24 Step 4, but employing N-(1-methylpiperidin-4-yl)-5-{2-[4-(amino)phenoxy]-4,6-dihydroxyphenyl}isoxazole-3-carboxamide instead of tert-butyl 4-{[(5-{2,4-bis[(2-methoxyethoxy)methoxy]-6-(4-aminophenoxy)phenyl}isoxazol-3-yl)carbonyl] amino}piperidine-1-carboxylate and tetrahydro-pyran-4-one instead formaldehyde, the title compound was obtained in 53% yield.

¹H NMR (400 MHz, DMSO-d₆) δ ppm 1.75-1.87 (m, 8H) 2.28 (s, 3H) 2.32-2.48 (m, 4H) 2.26-2.58 (m, 4H) 3.38-3.42 (m, 5H) 3.96-4.0 (m, 4H) 4.21 (m, 1H) 6.25 (d, 1H) 6.41 (d, 1H) 6.62 (m, 2H) 7.01 (m, 2H) 7.26 (s, 1H).

EXAMPLE 41

5-{2-[4-(Dimethylamino)phenoxy]-4,6-dihydroxyphenyl}-N-(1-methylpiperidin-4-yl)isoxazole-3-carboxamide

[(I); (Z)—R=4-(Dimethylamino)phenoxy, X=O, Y=N, W=CH, R₁=C₆H₁₃N₂O]

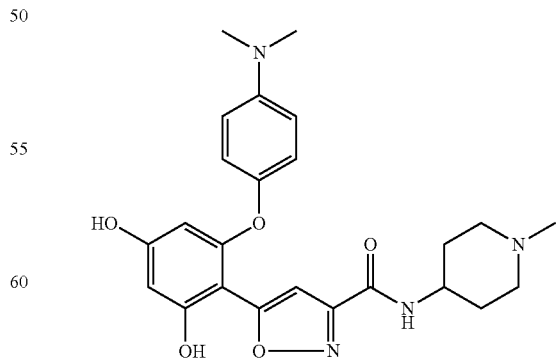

Operating as in Example 39, but employing formaldehyde instead of tetrahydro-pyran-4-one, the title compound was obtained in 76% yield.

¹H NMR (401 MHz, DMSO-d₆) δ ppm 1.55-1.67 (m, 2H) 1.67-1.77 (m, 2H) 1.89-1.98 (m, 2H) 2.16 (s, 3H) 2.71-2.79 (m, 2H) 2.87 (s, 6H) 3.64-3.78 (m, 1H) 5.65 (d, 1H) 6.14 (d, 1H) 6.73-6.76 (m, 2H) 6.77 (s, 1H) 6.87-6.92 (m, 2H) 8.52 (d, 1H) 9.80 (s, 1H) 10.19 (br. s., 1H).

EXAMPLE 42

5-{2,4-dihydroxy-6-[4-(propan-2-ylamino)phenoxy]phenyl}-N-(1-methylpiperidin-4-yl)isoxazole-3-carboxamide

[(I); (Z)—R=4-(Isopropylamino)phenoxy, X=O, Y=N, W=CH, $R_1=C_6H_{13}N_2O$]

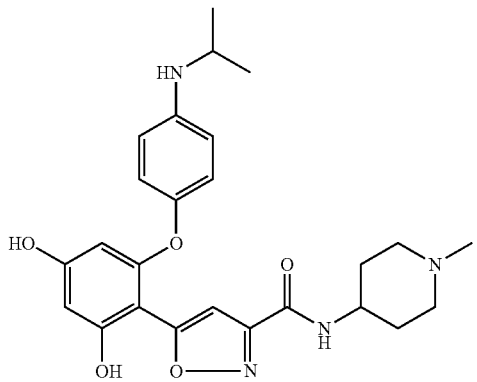 [SMILES: CC(C)Nc1ccc(Oc2cc(O)cc(O)c2-c2cc(C(=O)NC3CCN(C)CC3)no2)cc1]

Operating as in Example 40, but employing acetone instead of tetrahydro-pyran-4-one, the title compound was obtained in 56% yield.

¹H NMR (400 MHz, DMSO-d₆) δ ppm 1.12 (d, 6H) 1.53-1.67 (m, 2H) 1.68-1.75 (m, 2H) 1.86-1.96 (m, 2H) 2.14 (s, 3H) 2.68-2.79 (m, 2H) 3.43-3.54 (m, 1H) 3.62-3.77 (m, 1H) 5.29 (d, 1H) 5.64 (d, 1H) 6.10 (d, 1H) 6.52-6.59 (m, 2H) 6.76 (s, 1H) 6.77-6.81 (m, 2H) 8.51 (d, 1H).

EXAMPLE 43

5-{2-[4-(Cyclobutylamino)phenoxy]-4,6-dihydroxyphenyl}-N-(1-methylpiperidin-4-yl)isoxazole-3-carboxamide

[(I); (Z)—R=4-(Cyclobutylamino)phenoxy, X=O, Y=N, W=CH, $R_1=C_6H_{13}N_2O$]

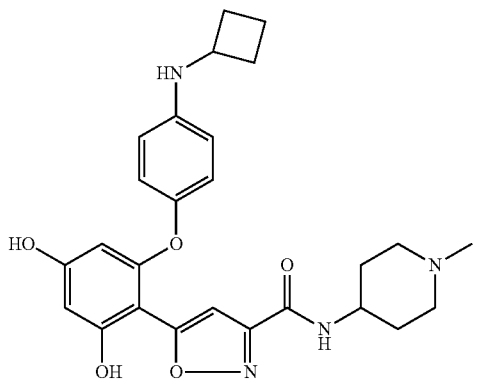 [SMILES: CN1CCC(NC(=O)c2cc(-c3c(O)cc(O)cc3Oc3ccc(NC4CCC4)cc3)on2)CC1]

Operating as in Example 40, but employing cyclobutanone instead of tetrahydro-pyran-4-one, the title compound was obtained in 23% yield.

¹H NMR (400 MHz, DMSO-d₆) δ ppm 1.11 (d, 6H) 1.51-1.68 (m, 6H) 1.63-1.71 (m, 2H) 1.86-1.95 (m, 2H) 2.14 (s, 3H) 2.7-2.8 (m, 2H) 3.42-3.55 (m, 1H) 3.65-3.78 (m, 1H) 5.3 (d, 1H) 5.6 (d, 1H) 6.10 (d, 1H) 6.54-6.6 (m, 2H) 6.76 (s, 1H) 6.77-6.81 (m, 2H) 8.51 (d, 1H).

EXAMPLE 44

5-{2,4-Dihydroxy-6-[4-(pyrrolidin-1-yl)phenoxy]phenyl}-N-(1-methylpiperidin-4-yl)isoxazole-3-carboxamide

[(I); (Z)—R=4-(4-Pyrrolidin-1-yl)phenoxy, X=O, Y=N, W=CH, $R_1=C_6H_{13}N_2O$]

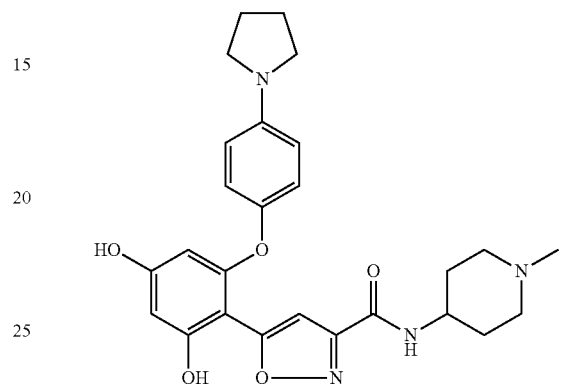

To stirred solution of N-(1-methylpiperidin-4-yl)-5-{2-[4-(amino)phenoxy]-4,6-dihydroxyphenyl}isoxazole-3-carboxamide (1.8 g, 4.2 mmol), 2,5-dimethoxytetrahydrofuran (1.1 g, 8.4 mmol, 2 eq.) and 5 M sulfuric acid solution (3 mL) in a mixture of methanol/tetrahydrofuran 1/1 (50 mL) was added portion wise NaBH₄ (0.46 g, 12 mmol, 4 eq.) at room temperature.

After stirring for 1 h, the solvent was removed and the residue taken up in ethyl acetate was washed with a NaHCO₃ saturated solution. After drying over Na₂SO₄, the solution was concentrated to a small volume, to provide after filtration and drying the title compound (0.75 g, yield 39%).

¹H NMR (400 MHz, DMSO-d₆) δ ppm 1.61 (m, 2H) 1.67-1.77 (m, 2H) 1.83-2.03 (m, 6H) 2.14 (s, 3H) 2.69-2.80 (m, 3H) 3.15-3.24 (m, 4H) 3.63-3.78 (m, 1H) 5.61 (d, 1H) 6.11 (d, 1H) 6.46-6.65 (m, 2H) 6.77 (s, 1H) 6.85-6.93 (m, 2H) 8.51 (d, 1H).

EXAMPLE 45

5-[2,4-Dihydroxy-6-(4-aminophenoxy)phenyl]-N-ethylisoxazole-3-carboxamide

[(I); (Z)—R=4-Aminophenoxy, X=O, Y=N, W=CH, $R_1=C_3H_6NO$]

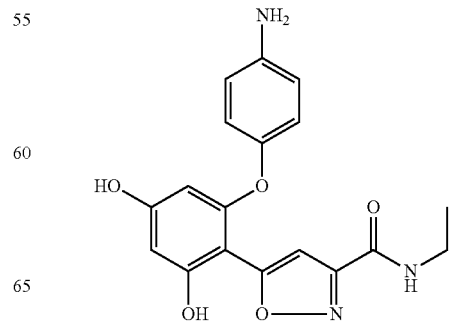

Scheme

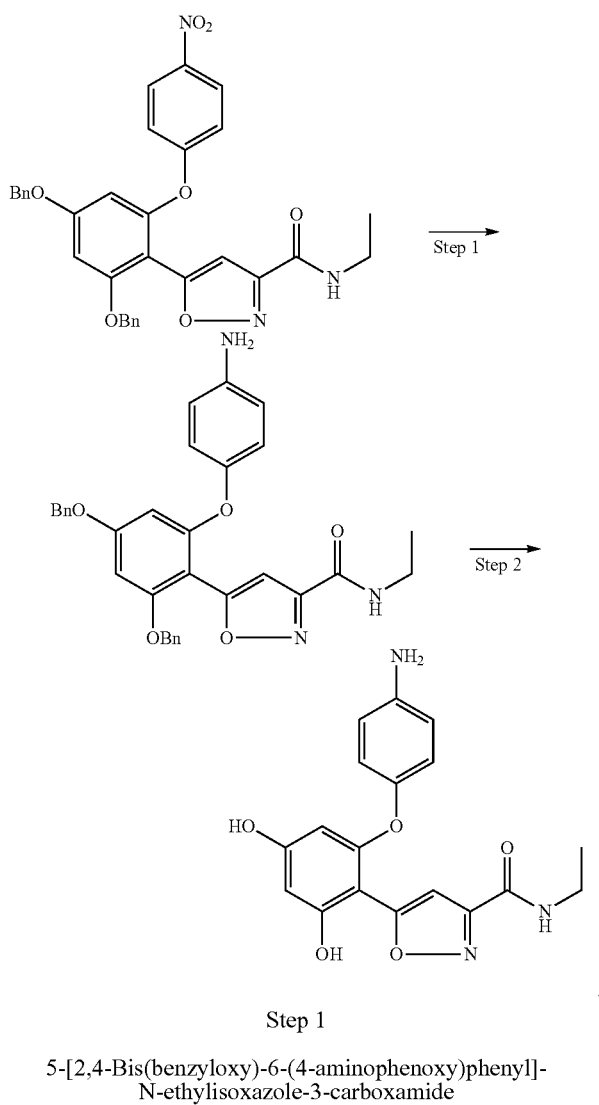

Step 1

5-[2,4-Bis(benzyloxy)-6-(4-aminophenoxy)phenyl]-N-ethylisoxazole-3-carboxamide

To a stirred solution of 5-[2,4-bis(benzyloxy)-6-(4-nitrophenoxy)phenyl]-N-ethylisoxazole-3-carboxamide (1.45 g, 2.6 mmol) and ammonium chloride (1.4 g, 6.4 mmol, 10 eq.) in dioxane (18 mL) and water (3 mL) was added powered Zn (0.7 g, 10 mmol, 4 eq.). After heating at 100° C. for 2 hours, the solution was filtered and the filtrate was diluted with ethyl acetate and washed with 1 M NaHCO₃ solution. After drying, the solvent was removed and the residue was chromatographed on silica gel eluting with hexane/ethyl acetate 3/1, to provide the title compound (0.69 g, 49% yield).

¹H NMR (400 MHz, DMSO-d₆) δ ppm 1.07-1.12 (m, 3H) 3.22-3.29 (m, 2H) 5.01-5.04 (m, 2H) 5.19-5.23 (m, 2H) 5.98 (d, 1H) 6.53-6.61 (m, 2H) 6.64 (d, 1H) 6.69-6.76 (m, 2H) 6.82-6.84 (m, 1H) 7.26-7.45 (m, 10H) 8.69-8.75 (m, 1H).

Step 2

5-[2,4-Dihydroxy-6-(4-aminophenoxy)phenyl]-N-ethylisoxazole-3-carboxamide

[(I); (Z)—R=4-Aminophenoxy, X=O, Y=N, W=CH, R₁=C₃H₆NO]

Operating as in Example 1 Step 5, but employing 5-[2,4-bis(benzyloxy)-6-(4-aminophenoxy)phenyl]-N-ethyl isoxazole-3-carboxamide instead of 5-[2,4-bis(benzyloxy)-6-(4-nitrophenoxy)phenyl]-N-ethyl isoxazole-3-carboxamide, the title compound was obtained in 35% yield.

¹H NMR (400 MHz, DMSO-d₆) δ ppm 1.09 (t, 3H) 3.20-3.29 (m, 2H) 5.76 (d, 1H) 6.22 (d, 1H) 6.76 (s, 1H) 6.84-6.97 (m, 4H) 8.65 (t, 1H) 9.95 (br. s., 1H) 10.33 (s, 1H).

EXAMPLE 46

5-{2-[4-(Acetylamino)phenoxy]-4,6-dihydroxyphenyl}-N-ethyl isoxazole-3-carboxamide

[(I); (Z)—R=4-Acetylaminophenoxy X=O, Y=N, W=CH, R₁=C₃H₆NO]

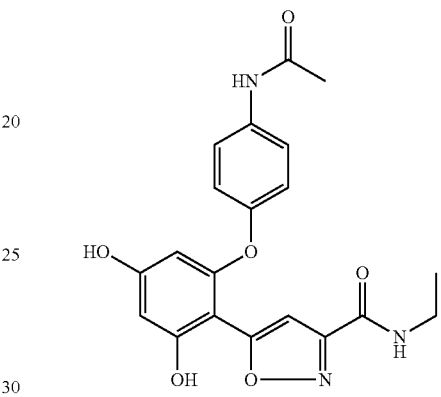

A stirred solution of 5-[2,4-dihydroxy-6-(4-aminophenoxy)phenyl]-N-ethylisoxazole-3-carboxamide (1 g, 2.8 mmol) in pyridine (30 mL) and acetic anhydride (0.32 g, 3 mmol) was refluxed for 1 hour. The solvent was removed and the residue was thoroughly washed with 2 M HCl solution, then with 2 M NaHCO₃ and brine. After drying, the solvent was removed and the crude was columned on a small pad of silica gel eluting with hexane/ethyl acetate 2/3, to afford after crystallization from diethyl ether, the title compound (0.75 g, 67% yield).

¹H NMR (400 MHz, DMSO-d₆) δ ppm 1.06-1.13 (m, 3H) 2.02 (s, 3H) 3.19-3.29 (m, 2H) 5.74 (d, 1H) 6.22 (d, 1H) 6.76 (s, 1H) 6.92-6.99 (m, 2H) 7.53-7.59 (m, 2H) 8.66 (t, 1H) 9.93 (s, 1H) 10.32 (s, 1H).

EXAMPLE 47

5-{2-[4-(Dimethylamino)phenoxy]-4,6-dihydroxyphenyl}-N-ethylisoxazole-3-carboxamide

[(I); (Z)—R=4-(Dimethylamino)phenoxy, X=O, Y=N, W=CH, R₁=C₃H₆NO]

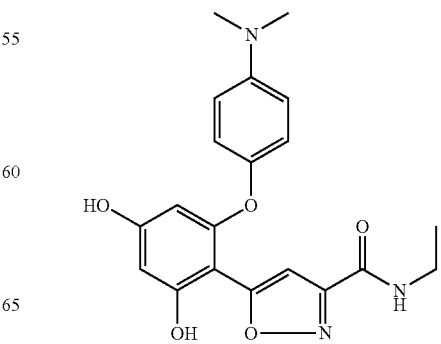

To a stirred solution of 5-[2,4-dihydroxy-6-(4-aminophenoxy)phenyl]-N-ethylisoxazole-3-carboxamide (0.55 g, 1.5 mmol), acetic acid (0.2 mL) and 37% formaldehyde/H₂O solution (1 mL) in ethanol (30 mL) was added sodium triacetoxyborohydride (0.29 g, 2.5 mmol). After stirring for 1 hour at rt, the solvent was removed and the residue taken up in ethyl acetate was washed with 2 M NaHCO₃ solution, then with brine and dried. After removal of the solvent, the residue was crystallized twice from diethyl ether, to provide the title compound (0.24 g, 42% yield).

¹H NMR (400 MHz, DMSO-d₆) δ ppm 1.06-1.13 (m, 3H) 2.02 (s, 3H) 2.92 (s, 6H) 3.19-3.29 (m, 2H) 5.74 (d, 1H) 6.22 (d, 1H) 6.76 (s, 1H) 6.92-6.99 (m, 2H) 7.53-7.59 (m, 2H) 8.66 (t, 1H) 9.93 (s, 1H) 10.32 (s, 1H).

EXAMPLE 48

5-{2-[4-(Isopropylamino)phenoxy]-4,6-dihydroxyphenyl}-N-ethylisoxazole-3-carboxamide

[(I); (Z)—R=4-(Isopropylamino)phenoxy, X=O, Y=N, W=CH, R₁=C₃H₆NO]

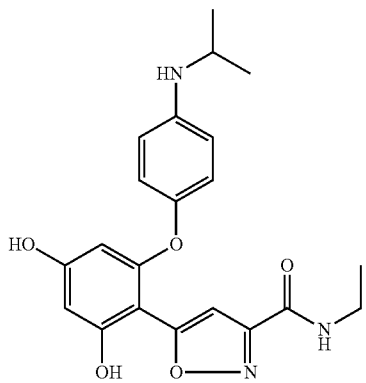 [SMILES: CCNC(=O)c1cc(-c2c(O)cc(O)cc2Oc2ccc(NC(C)C)cc2)on1]

Operating as Example 47, but employing acetone instead of formaldehyde, the title compound was obtained in 35% yield.

¹H NMR (400 MHz, DMSO-d₆) δ ppm 1.05-1.15 (m, 3H) 1.13 (m, 6H) 2.02 (s, 3H) 2.91 (s, 6H) 3.15-3.27 (m, 2H) 3.49 (1H) 5.29 (m, 1H) 5.75 (d, 1H) 6.21 (d, 1H) 6.76 (s, 1H) 6.90-6.96 (m, 2H) 7.54-7.69 (m, 2H) 8.63 (t, 1H) 9.94 (s, 1H) 10.37 (s, 1H).

EXAMPLE 49

5-{2-[4-(Benzylamino)phenoxy]-4,6-dihydroxyphenyl}-N-ethylisoxazole-3-carboxamide

[(I); (Z)—R=4-(Benzylamino)phenoxy, X=O, Y=N, W=CH, R₁=C₃H₆NO]

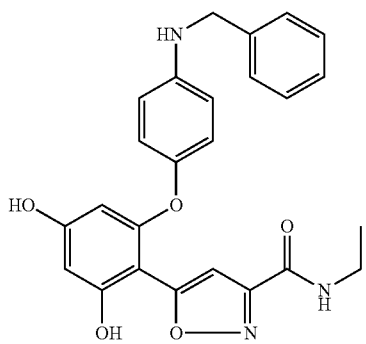 [SMILES: CCNC(=O)c1cc(-c2c(O)cc(O)cc2Oc2ccc(NCc3ccccc3)cc2)on1]

Operating as Example 47, but employing benzaldehyde instead of formaldehyde, the title compound was obtained in 53% yield.

¹H NMR (400 MHz, DMSO-d₆) δ ppm 1.06-1.13 (m, 3H) 1.11 (m, 6H) 1.25 (s, 2H) 2.03 (s, 3H) 2.89 (s, 6H) 3.14-3.28 (m, 2H) 3.47 (1H) 5.28 (m, 1H) 5.77 (d, 1H) 6.23 (d, 1H) 6.74 (s, 1H) 6.92-6.97 (m, 2H) 7.33-7.48 (m, 5H) 7.53-7.68 (m, 2H) 8.65 (t, 1H) 9.95 (s, 1H) 10.39 (s, 1H).

EXAMPLE 50

5-{2-[4-(Dimethylamino)phenoxy]-4,6-dihydroxyphenyl}-N-[1-(4,4,4-trifluorobutyl)piperidin-4-yl]isoxazole-3-carboxamide

[(I); (Z)—R=4-Dimethylaminophenoxy, X=O, Y=N, W=CH, R₁=C₆H₁₆F₃N₂O]

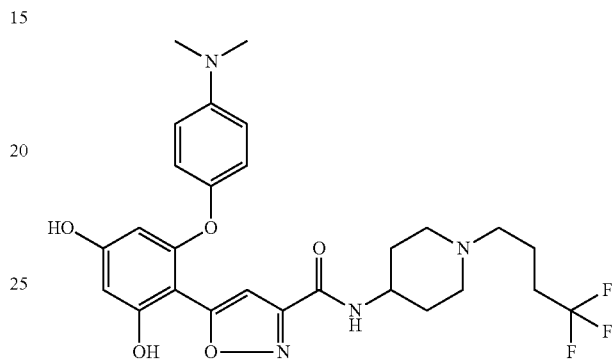

Operating as in Example 34, but employing 5-[3,5-dihydroxy-2-(4-dimethylamino)phenyl]-N-(piperidin-4-yl)isoxazole-3-carboxamide dihydrochloride instead of 5-[3,5-dihydroxy-2-(4-nitrophenoxy)phenyl]-N-(piperidin-4-yl)isoxazole-3-carboxamide hydrochloride, the title compound was obtained in 27% yield.

¹H NMR (400 MHz, DMSO-d₆) δ ppm 2.86-2.88 (m, 2H) 3.74 (br. s., 1H) 5.65 (d, 1H) 6.14 (d, 1H) 6.73-6.76 (m, 1H) 6.77 (s, 1H) 6.86-6.94 (m, 1H) 8.53 (d, 1H) 9.80 (s, 1H) 10.19 (s, 1H).

EXAMPLE 51

5-[2,4-Dihydroxy-6-(4-nitrophenoxy)phenyl]-N-{1-[2-(dimethylamino)ethyl]piperidin-4-yl}isoxazole-3-carboxamide

[(I); (Z)—R=4-Nitrophenoxy, X=O, Y=N, W=CH, R₁=CONHC₉H₁₉N₂]

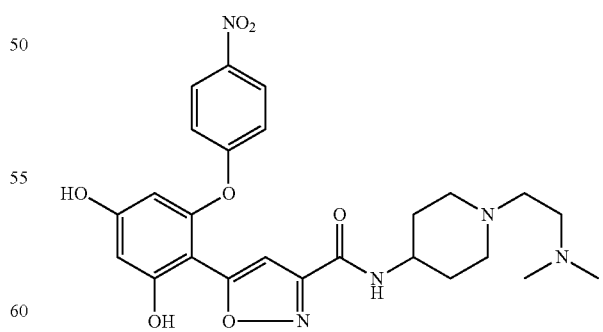

Operating as in Example 34, but employing 2-bromoethyl-dimethyl-amine hydrochloride instead of 4-bromo-1,1,1-trifluoro-butane, the title compound was obtained in 42% yield.

¹H NMR (400 MHz, DMSO-d₆) δ ppm 6.12 (d, 1H) 6.53 (d, 1H) 6.83 (s, 1H) 7.09 (d, 2H) 8.21 (d, 2H) 10.40 (br. s., 1H) 10.82 (s, 1H).

EXAMPLE 52
3-[2,4-Dihydroxy-6-(4-nitrophenoxy)phenyl]-N-ethylisoxazole-5-carboxamide
[(I); (Z)—R=4-Nitrophenoxy, X=N, Y=O, W=CH, $R_1=C_3H_6NO$]
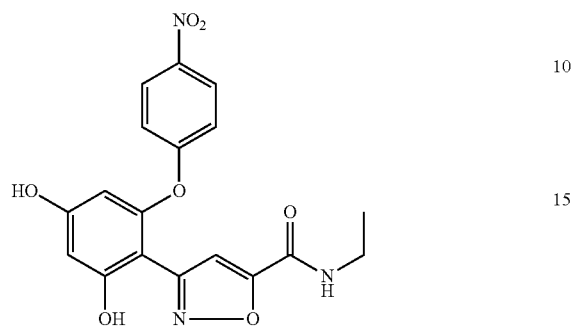
Scheme
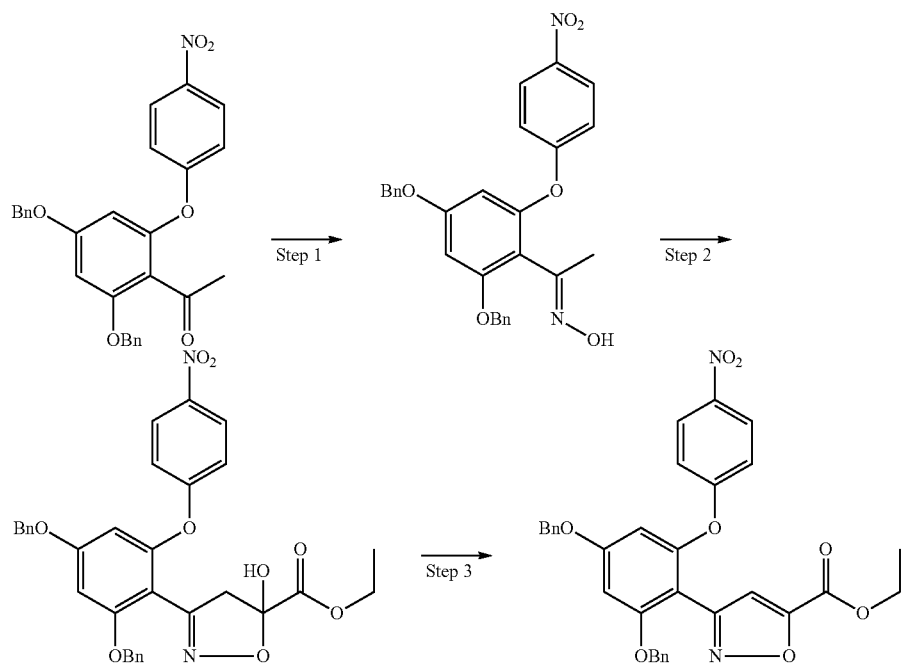
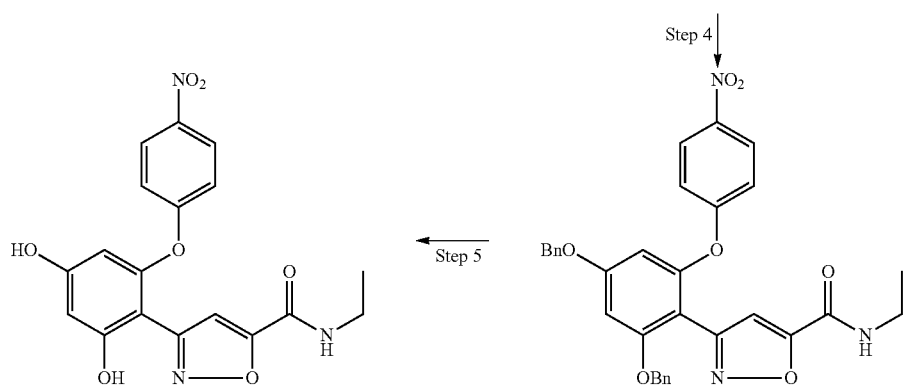

Step 1

1-[2,4-Bis(benzyloxy)-6-(4-nitrophenoxy)phenyl]-N-hydroxyethanimine

A stirred solution of 1-[2,4-bis(benzyloxy)-6-(4-nitrophenoxy)phenyl]ethanone (15 g, 32 mmol), $NH_2OH \cdot HCl$ (3 g, 42 mmol) and $CH_3COONa$ (3.5 g, 42 mmol) in ethanol (150 mL) and acetic acid (250 mL) was refluxed for 5 hours. The solvent was removed and the residue taken up in ethyl acetate was thoroughly washed with 2 M $NaHCO_3$ solution then with brine. After drying over $Na_2SO_4$, the solvent was removed and the oily residue was filtered on a small pad of silica gel eluting with hexane/ethyl acetate 6/3 to provide the title compound (13.3 g, 88% yield).

$^1H$ NMR (400 MHz, DMSO-$d_6$) δ ppm 2.27 (s, 3H) 5.13 (s, 2H) 5.18 (s, 2H) 7.14 (dd, 2H) 7.38 (m, 10H) 8.28 (dd, 2H) 10.8 (bs, 1H).

Step 2

Ethyl 3-[2,4-bis(benzyloxy)-6-(4-nitrophenoxy)phenyl]-5-hydroxy-4,5-dihydroisoxazole-5-carboxylate To a stirred solution of 1-[2,4-bis(benzyloxy)-6-(4-nitrophenoxy)phenyl]-N-hydroxyethanimine (10 g, 44 mmol) was added drop wise 2 M n-ButLi in hexane (45 mL, 44 mmol) at −78° C. and the stirring was continued for 1 hour at −78° C. then for ½ hour at room temperature. After recooling at −78° C., a solution of diethyl oxalate (3.22 g, 22 mmol) in THF (50 mL) was cannuled into the cloudy solution. The mixture was warmed at rt over 16 hours before the addition of a $NH_4Cl$ saturated solution (100 mL). The organic and aqueous layers were separated and the latter was diluted with ethyl acetate and thoroughly washed with brine. After drying over $Na_2SO_4$, the solvent was removed and the residue was chromatographed on silica gel eluting with ethyl acetate/hexane 7/5, to provide the title compound (2.7 g, yield 17%).

$^1H$ NMR (400 MHz, DMSO-$d_6$) δ ppm 1.27 (t, 3H) 3.54 (q, 1H) 3.66 (d, 1H) 4.24 (t, 2H) 4.82 (bs, 1H) 5.13 (s, 2H) 5.19 (s, 2H) 6.27 (d, 1H) 6.35 (d, 1H) 7.12-7.50 (m, 12H) 8.28 (m, 2H).

Step 3

Ethyl 3-[2,4-bis(benzyloxy)-6-(4-nitrophenoxy)phenyl]isoxazole-5-carboxylate A stirred solution of ethyl 3-[2,4-bis(benzyloxy)-6-(4-nitrophenoxy)phenyl]-5-hydroxy-4,5-dihydroisoxazole-5-carboxylate (8.5 g, 14 mmol) and tosic acid hydrate (5.5 g, 29.5 mmol, 2.1 eq.) in toluene (150 mL) was refluxed for 6 hours. After cooling, the solution was washed with 1 M $Na_2CO_3$ solution then with brine. The solvent was removed and the residue was columned over a small pad of silica gel eluting with hexane/ethyl acetate 5/1 to provide the title compound (6.3 g, 79% yield).

$^1H$ NMR (400 MHz, DMSO-$d_6$) δ ppm 1.41 (t, 3H) 4.34 (q, 1H) 5.11 (s, 2H) 5.15 (s, 2H) 6.27 (d, 2H) 7.16 (d, 2H) 7.11-7.52 (m, 10H) 8.25 (m, 2H).

Step 4

3-[2,4-Bis(benzyloxy)-6-(4-nitrophenoxy)phenyl]-N-ethylisoxazole-5-carboxamide Operating as in Example 1 Step 4, but employing ethyl 3-[2,4-bis(benzyloxy)-6-(4-nitrophenoxy)phenyl]isoxazole-5-carboxylate instead of ethyl 5-[2,4-bis(benzyloxy)-6-(4-nitrophenoxy)phenyl]isoxazole-3-carboxylate, the title compound was obtained in 47% yield.

$^1H$ NMR (400 MHz, DMSO-$d_6$) δ ppm 1.17 (t, 3H) 3.41 (q, 1H) 5.10 (s, 2H) 5.16 (s, 2H) 6.32 (d, 2H) 6.84 (s, 1H) 7.16 (m, 2H) 7.13-7.53 (m, 10H) 7.66 (bs, 1H) 8.23 (m, 2H) 10.23 (bs, 1H).

Step 5

3-[2,4-Dihydroxy-6-(4-nitrophenoxy)phenyl]-N-ethyl isoxazole-5-carboxamide

[(I); (Z)—R=4-Nitrophenoxy, X=N, Y=O, W=CH, $R_1=C_3H_6NO$]

Operating as in Example 1 Step 5, but employing 3-[2,4-bis(benzyloxy)-6-(4-nitrophenoxy)phenyl]-N-ethylisoxazole-5-carboxamide instead of 5-[2,4-bis(benzyloxy)-6-(4-nitrophenoxy)phenyl]-N-ethylisoxazole-3-carboxamide, the title compound was obtained in 23% yield.

$^1H$ NMR (400 MHz, DMSO-$d_6$) δ ppm 1.18 (t, 3H) 3.43 (q, 1H) 5.13 (s, 2H) 5.19 (s, 2H) 6.34 (d, 2H) 6.84 (s, 1H) 7.18 (m, 2H) 7.75 (bs, 1H) 8.31 (m, 2H) 10.07 (bs, 2H) 10.23 (bs, 1H).

An alternative route via a 1,3-dipolar cycloaddition is also an object of the invention:

Preparation of Ethyl 3-[2,4-dimethoxy-6-(4-nitrophenoxy)phenyl]isoxazole-5-carboxylate

[(XXI), (Z)—R=4-Nitrophenoxy, X=N, Y=O, W=CH $R'_1=CO_2C_2H_5$]

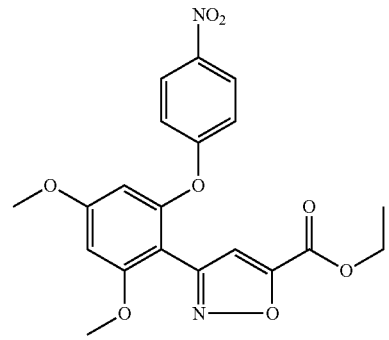 [SMILES: CCOC(=O)c1cc(-c2c(OC)cc(OC)cc2Oc2ccc([N+](=O)[O-])cc2)no1]

Scheme

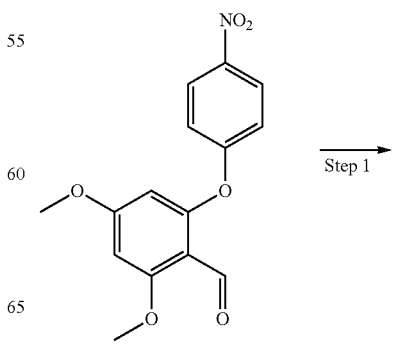

Step 1

-continued

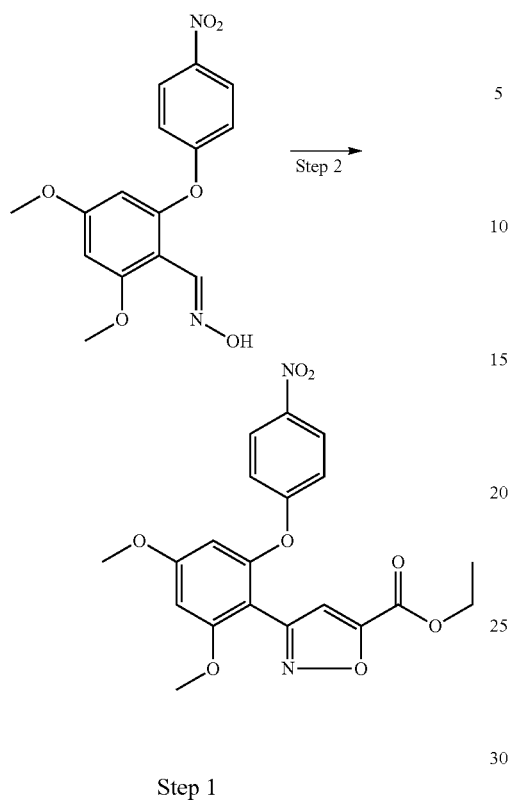

Step 1

1-[2,4-Dimethoxy-6-(4-nitrophenoxy)phenyl]-N-hydroxymethanimine

Operating as in Example 52 Step 1, but employing 2,4-dimethoxy-6-(4-nitro-phenoxy)-benzaldehyde instead of 1-[2,4-bis(benzyloxy)-6-(4-nitrophenoxy)phenyl]ethanone, the title compound was obtained as a mixture of diastereoisomers in 73% yield.

Step 2

Ethyl 3-[2,4-dimethoxy-6-(4-nitrophenoxy)phenyl]isoxazole-5-carboxylate

To a stirred solution of 1-[2,4-dimethoxy-6-(4-nitrophenoxy)phenyl]-N-hydroxymethanimine (2.06 g, 6.7 mmol) and ethyl propiolate (3.28 mL, 32.4 mmol, 5 eq.) in DCM was slowly added drop wise 15% NaOCl solution (65 mL) at 0° C. After stirring overnight, the organic phase was separated and the aqueous was extracted twice with DCM. The organic phases were pooled and washed with 1 M $Na_2SO_3$ solution, then with brine and dried over $Na_2SO_4$. The solvent was removed and the residue was carefully chromatographed on silica gel eluting with hexane/ethyl acetate 8/2 to provide the title compound (1.6 g, 57% yield)

$^1$H NMR (400 MHz, DMSO-$d_6$) δ ppm 1.29 (t, 3H) 3.82 (s, H) 3.85 (s, 3H) 4.33 (q, 2H) 6.49 (d, 1H) 6.72 (d, 1H) 6.97-7.12 (m, 2H) 7.27 (s, 1H) 8.13-8.26 (m, 2H).

Ethyl 3-[2,4-dimethoxy-6-(4-nitrophenoxy)phenyl]isoxazole-4-carboxylate

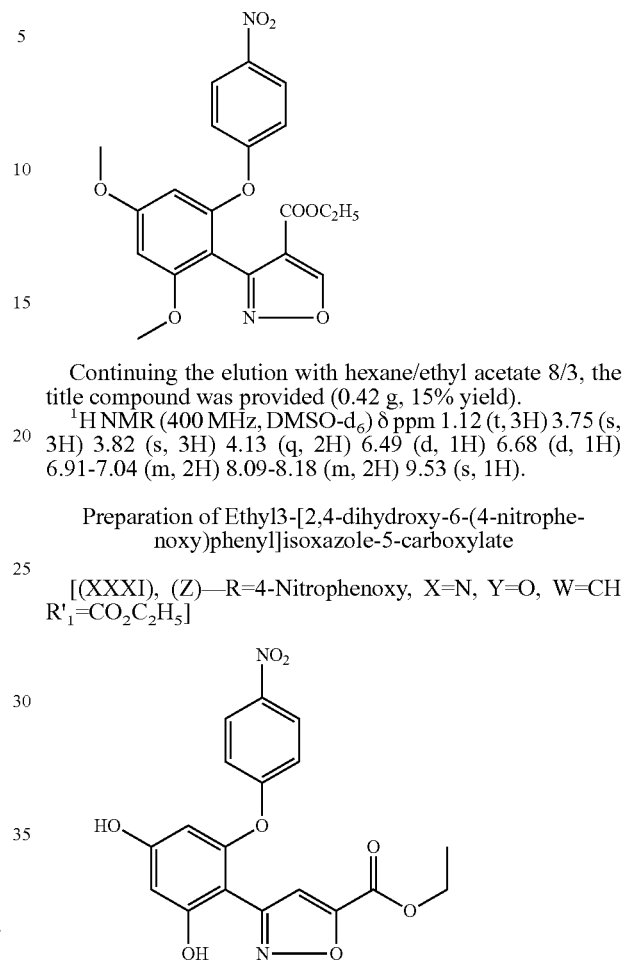

Continuing the elution with hexane/ethyl acetate 8/3, the title compound was provided (0.42 g, 15% yield).

$^1$H NMR (400 MHz, DMSO-$d_6$) δ ppm 1.12 (t, 3H) 3.75 (s, 3H) 3.82 (s, 3H) 4.13 (q, 2H) 6.49 (d, 1H) 6.68 (d, 1H) 6.91-7.04 (m, 2H) 8.09-8.18 (m, 2H) 9.53 (s, 1H).

Preparation of Ethyl 3-[2,4-dihydroxy-6-(4-nitrophenoxy)phenyl]isoxazole-5-carboxylate

[(XXXI), (Z)—R=4-Nitrophenoxy, X=N, Y=O, W=CH R'$_1$=CO$_2$C$_2$H$_5$]

Operating as in Example 1 Step 5, but employing ethyl 3-[2,4-dimethoxy-6-(4-nitrophenoxy)phenyl]isoxazole-5-carboxylate instead of 5-[2,4-bis(benzyloxy)-6-(4-nitrophenoxy)phenyl]-N-ethylisoxazole-3-carboxamide, the title compound was obtained in 37% yield.

$^1$H NMR (400 MHz, DMSO-$d_6$) δ ppm 1.31 (t, 3H) 4.32 (q, 2H) 6.51 (d, 1H) 6.73 (d, 1H) 6.95-7.15 (m, 2H) 7.29 (s, 1H) 8.12-8.23 (m, 2H) 10.13-10.26 (bs, 2H).

Preparation of Ethyl 3-[2,4-dihydroxy-6-(4-nitrophenoxy)phenyl]isoxazole-5-carboxylate

[(XXXI), (Z)—R=4-Nitrophenoxy, X=N, Y=O, W=CH R'$_1$=CO$_2$C$_2$H$_5$]

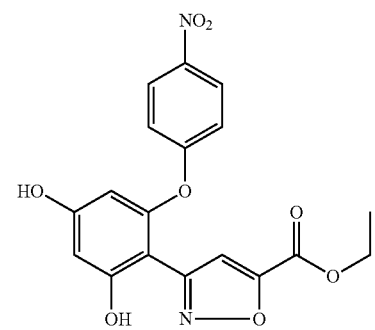 [SMILES: CCOC(=O)c1cc(-c2c(O)cc(O)cc2Oc2ccc([N+](=O)[O-])cc2)no1]

Scheme

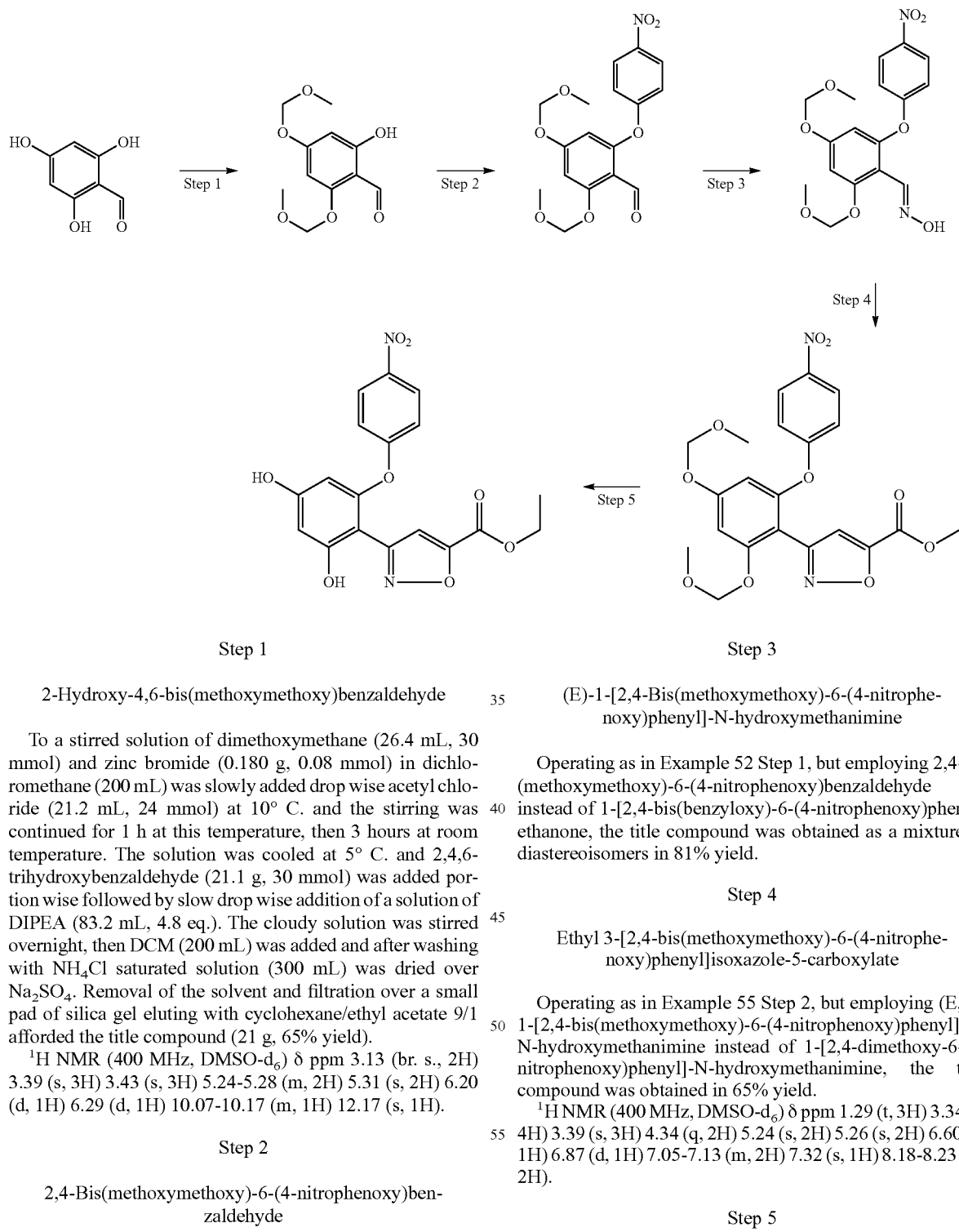

Step 1

2-Hydroxy-4,6-bis(methoxymethoxy)benzaldehyde

To a stirred solution of dimethoxymethane (26.4 mL, 30 mmol) and zinc bromide (0.180 g, 0.08 mmol) in dichloromethane (200 mL) was slowly added drop wise acetyl chloride (21.2 mL, 24 mmol) at 10° C. and the stirring was continued for 1 h at this temperature, then 3 hours at room temperature. The solution was cooled at 5° C. and 2,4,6-trihydroxybenzaldehyde (21.1 g, 30 mmol) was added portion wise followed by slow drop wise addition of a solution of DIPEA (83.2 mL, 4.8 eq.). The cloudy solution was stirred overnight, then DCM (200 mL) was added and after washing with NH$_4$Cl saturated solution (300 mL) was dried over Na$_2$SO$_4$. Removal of the solvent and filtration over a small pad of silica gel eluting with cyclohexane/ethyl acetate 9/1 afforded the title compound (21 g, 65% yield).

$^1$H NMR (400 MHz, DMSO-d$_6$) δ ppm 3.13 (br. s., 2H) 3.39 (s, 3H) 3.43 (s, 3H) 5.24-5.28 (m, 2H) 5.31 (s, 2H) 6.20 (d, 1H) 6.29 (d, 1H) 10.07-10.17 (m, 1H) 12.17 (s, 1H).

Step 2

2,4-Bis(methoxymethoxy)-6-(4-nitrophenoxy)benzaldehyde

Operating as in Example 1 Step 2, but employing 2-hydroxy-4,6-bis(methoxymethoxy)benzaldehyde instead of 1-[2,4-bis(benzyloxy)-6-(4-nitrophenoxy)phenyl]ethanone, the title compound was obtained in 74% yield.

$^1$H NMR (400 MHz, DMSO-d$_6$) δ ppm 2.38 (s, 3H) 3.37 (s, 3H) 3.41 (s, 3H) 5.19 (s, 2H) 5.28 (s, 2H) 6.47 (d, 1H) 6.76 (d, 1H) 7.07-7.16 (m, 2H) 8.20-8.28 (m, 2H).

Step 3

(E)-1-[2,4-Bis(methoxymethoxy)-6-(4-nitrophenoxy)phenyl]-N-hydroxymethanimine Operating as in Example 52 Step 1, but employing 2,4-bis(methoxymethoxy)-6-(4-nitrophenoxy)benzaldehyde instead of 1-[2,4-bis(benzyloxy)-6-(4-nitrophenoxy)phenyl]ethanone, the title compound was obtained as a mixture of diastereoisomers in 81% yield.

Step 4

Ethyl 3-[2,4-bis(methoxymethoxy)-6-(4-nitrophenoxy)phenyl]isoxazole-5-carboxylate Operating as in Example 55 Step 2, but employing (E,Z)-1-[2,4-bis(methoxymethoxy)-6-(4-nitrophenoxy)phenyl]-N-hydroxymethanimine instead of 1-[2,4-dimethoxy-6-(4-nitrophenoxy)phenyl]-N-hydroxymethanimine, the title compound was obtained in 65% yield.

$^1$H NMR (400 MHz, DMSO-d$_6$) δ ppm 1.29 (t, 3H) 3.34 (s, 4H) 3.39 (s, 3H) 4.34 (q, 2H) 5.24 (s, 2H) 5.26 (s, 2H) 6.60 (d, 1H) 6.87 (d, 1H) 7.05-7.13 (m, 2H) 7.32 (s, 1H) 8.18-8.23 (m, 2H).

Step 5

Ethyl 3-[2,4-dihydroxy-6-(4-nitrophenoxy)phenyl]isoxazole-5-carboxylate

[(XXXI), (Z)—R=4-Nitrophenoxy, X=N, Y=O, W=CH R$_1$=CO$_2$C$_2$H$_5$]

To a stirred solution of ethyl 3-[2,4-bis(methoxymethoxy)-6-(4-nitrophenoxy)phenyl]isoxazole-5-carboxylate (25 g, 64.7 mmol) in ethanol (125 mL) was added 4 M HCl in dioxane (25 mL, 100 mmol) at room temperature. After 4 hours, the solvent was removed and the residue was crystallized from a small volume of ethanol, to provide the title compound (18.3 g, yield 90%).

$^1$H NMR (400 MHz, DMSO-d$_6$) δ ppm 1.26-1.31 (m, 3H) 4.33 (q, 2H) 6.07 (d, 1H) 6.43 (d, 1H) 7.04-7.08 (m, 2H) 7.26 (s, 1H) 8.15-8.21 (m, 2H) 10.14 (s, 1H) 10.37 (s, 1H).

EXAMPLE 53

3-[2,4-Dihydroxy-6-(4-nitrophenoxy)phenyl]-N-(1-methylpiperidin-4-yl)isoxazole-5-carboxamide

[(I); (Z)—R=4-Nitrophenoxy, X=N, Y=O, W=CH, R$_1$=C$_6$H$_{13}$N$_2$O]

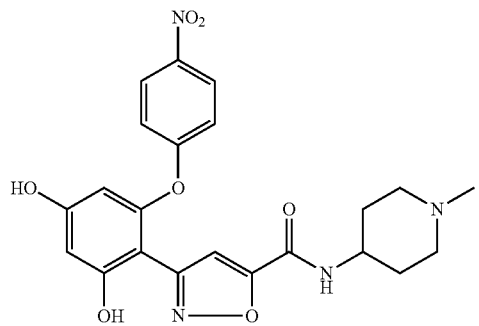 [SMILES: CN1CCC(NC(=O)c2cc(-c3c(O)cc(O)cc3Oc3ccc([N+](=O)[O-])cc3)no2)CC1]

Scheme

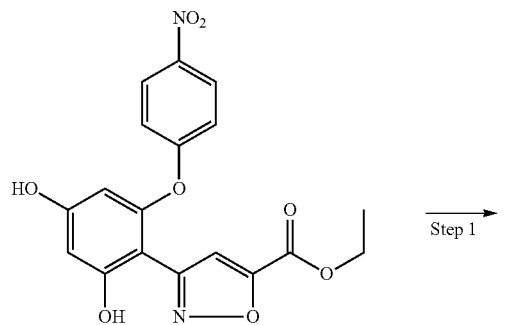

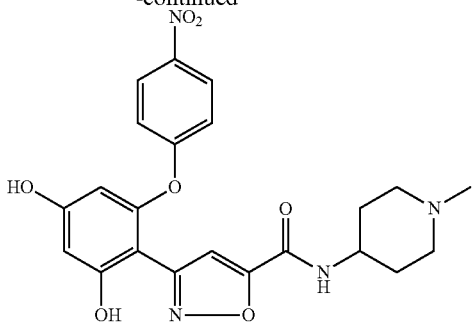

Step 1

3-[2,4-Dihydroxy-6-(4-nitrophenoxy)phenyl]isoxazole-5-carboxylic acid

[(XXXI); (Z)—R=4-Nitrophenoxy, X=N, Y=O, W=CH, R$_1$=C$_6$H$_{13}$N$_2$O]

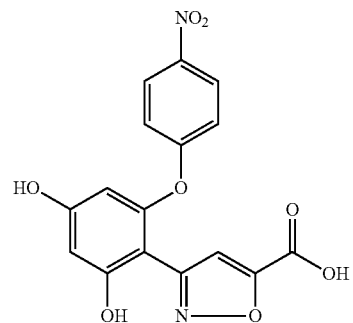 [SMILES: O=C(O)c1cc(-c2c(O)cc(O)cc2Oc2ccc([N+](=O)[O-])cc2)no1]

To a stirred solution of ethyl 3-[2,4-dihydroxy-6-(4-nitrophenoxy)phenyl]isoxazole-5-carboxylate (4 g, 10 mmol) in ethanol (50 mL) was added 2 M NaOH solution (6 mL) at room temperature. After stirring for 5 hours, the solution was diluted with ethyl acetate and treated with 2 M HCl solution (7 mL). The organic phase was washed with brine and dried over Na$_2$SO$_4$. The solvent was removed and the residue was taken up in a small volume of acetone to afford after drying, the title compound (2.8 g, 76% yield).

$^1$H NMR (400 MHz, DMSO-d$_6$) δ ppm 6.05 (d, 1H) 6.40 (d, 1H) 6.65 (br. s., 1H) 7.01-7.09 (m, 2H) 8.17-8.21 (m, 2H) 10.07 (s, 1H) 10.27 (s, 1H).

Step 2

3-[2,4-Dihydroxy-6-(4-nitrophenoxy)phenyl]-N-(1-methylpiperidin-4-yl)isoxazole-5-carboxamide

[(I); (Z)—R=4-Nitrophenoxy, X=N, Y=O, W=CH, R$_1$=C$_6$H$_{13}$N$_2$O]

Operating as in Example 6 Step 1, but employing 3-[2,4-dihydroxy-6-(4-nitrophenoxy)phenyl]isoxazole-5-carboxylic acid instead of 5-[2,4-bis(benzyloxy)-6-(4-nitrophenoxy)phenyl]isoxazole-3-carboxylic acid and 1-methyl-piperidin-4-ylamine instead of tert-butyl (2-aminoethyl)methylcarbamate, the title compound was obtained in 68% yield.

$^1$H NMR (400 MHz, DMSO-d$_6$) δ ppm 1.48-1.62 (m, 2H) 1.64-1.74 (m, 2H) 1.82-1.97 (m, 2H) 2.14 (s, 3H) 2.73 (d, 2H) 3.66 (d, 1H) 6.08 (d, 1H) 6.43 (d, 1H) 6.98-7.07 (m, 2H) 7.09 (s, 1H) 8.14-8.23 (m, 2H) 8.69 (d, 1H) 10.13 (br. s., 2H).

EXAMPLE 54
3-{2-[4-(Dimethylamino)phenoxy]-4,6-dihydroxyphenyl}-N-(1-methylpiperidin-4-yl)isoxazole-5-carboxamide
[(I); (Z)—R=4-(Dimethylamino)phenoxy, X=N, Y=O, W=CH, $R_1=C_6H_{13}N_2O$]
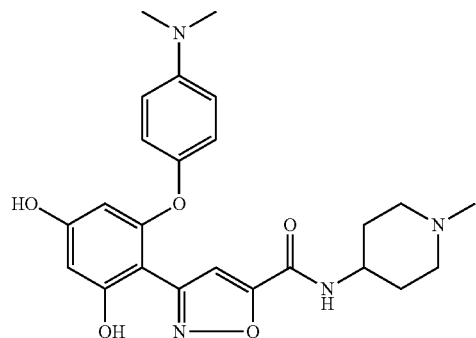 [SMILES: CN1CCC(NC(=O)c2cc(-c3c(O)cc(O)cc3Oc3ccc(N(C)C)cc3)no2)CC1]
Scheme
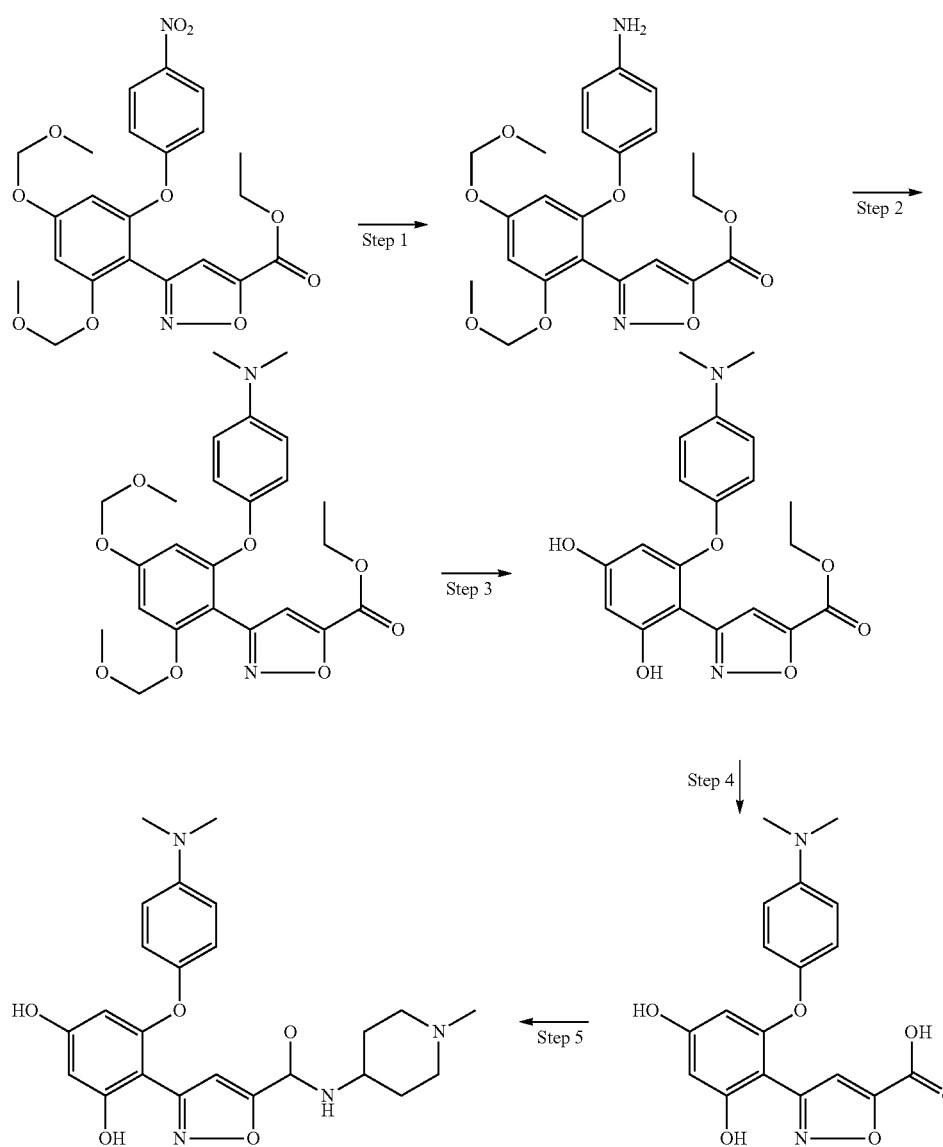

101

Step 1

Ethyl 3-[2-(4-aminophenoxy)-4,6-bis(methoxymethoxy)phenyl]isoxazole-5-carboxylate Operating as in Example 24 Step 3, but employing ethyl 3-[2,4-bis(methoxymethoxy)-6-(4-nitrophenoxy)phenyl] isoxazole-5-carboxylate instead of tert-butyl 4-{[(5-{2,4-bis [(2-methoxyethoxy)methoxy]-6-(4-nitrophenoxy) phenyl}isoxazol-3-yl)carbonyl]amino}piperidine-1-carboxylate, the title compound was obtained in 65% yield.

$^1$H NMR (400 MHz, DMSO-d$_6$) δ ppm 1.29 (t, 3H) 3.34 (s, 4H) 3.39 (s, 3H) 4.34 (q, 2H) 5.24 (s, 2H) 5.26 (s, 2H) 6.64 (d, 1H) 6.69-6.76 (m, 2H) 6.82-6.84 (m, 1H) 7.26-7.45 (m, 10H).

Step 2

Ethyl 3-{2-[4-(dimethylamino)phenoxy]-4,6-bis(methoxymethoxy)phenyl}isoxazole-5-carboxylate Operating as in Example 24 Step 4, but employing ethyl 3-[2-(4-aminophenoxy)-4,6-bis(methoxymethoxy)phenyl] isoxazole-5-carboxylate instead of tert-butyl 4-{[(5-{2,4-bis [(2-methoxyethoxy)methoxy]-6-(4-aminophenoxy) phenyl}isoxazol-3-yl)carbonyl]amino}piperidine-1-carboxylate, the title compound was obtained in 75% yield.

$^1$H NMR (400 MHz, DMSO-d$_6$) δ ppm 1.32 (t, 3H) 2.87 (s, 6H) 3.32 (s, 4H) 3.33 (s, 3H) 4.37 (q, 2H) 5.09-5.12 (m, 2H) 5.18 (s, 2H) 6.06 (d, 1H) 6.62 (d, 1H) 6.70-6.76 (m, 2H) 6.86-6.94 (m, 2H) 7.35 (s, 1H)

Step 3

Ethyl 3-{2-[4-(dimethylamino)phenoxy]-4,6-dihydroxyphenyl}isoxazole-5-carboxylate Operating as in Example 24 Step 5, but employing ethyl 3-{2-[4-(dimethylamino)phenoxy]-4,6-bis(methoxymethoxy)phenyl}isoxazole-5-carboxylate instead of tert-butyl 4-{[(5-{2,4-bis[(2-methoxyethoxy)methoxy]-6-(4-dimethylaminophenoxy)phenyl}isoxazol-3-yl)carbonyl] amino}piperidine-1-carboxylate, the title compound was obtained in 83% yield.

$^1$H NMR (400 MHz, DMSO-d$_6$) δ ppm 1.32 (t, 3H) 2.87 (s, 6H) 4.37 (q, 2H) 5.65 (d, 1H) 6.12 (d, 1H) 6.70-6.76 (m, 2H) 6.86-6.92 (m, 2H) 7.29 (s, 1H) 9.68 (s, 1H) 9.88 (s, 1H).

Step 4

3-{2-[4-(Dimethylamino)phenoxy]-4,6-dihydroxyphenyl}isoxazole-5-carboxylic acid Operating as in Example 53 Step 1, but employing ethyl 3-{2-[4-(dimethylamino)phenoxy]-4,6-dihydroxyphenyl}isoxazole-5-carboxylate instead of ethyl 3-[2,4-dihydroxy-6-(4-nitrophenoxy)phenyl]isoxazole-5-carboxylate, the title compound was obtained in 74% yield.

$^1$H NMR (400 MHz, DMSO-d$_6$) δ ppm 2.87 (s, 6H) 5.65 (d, 1H) 6.12 (d, Hz, 1H) 6.70-6.81 (m, 2H) 6.85-6.93 (m, 2H) 7.16-7.27 (m, 1H) 9.67 (s, 1H) 9.86 (s, 1H).

Step 5

3-{2-[4-(Dimethylamino)phenoxy]-4,6-dihydroxyphenyl}-N-(1-methylpiperidin-4-yl)isoxazole-5-carboxamide

[(I); (Z)—R=4-(Dimethylamino)phenoxy, X=N, Y=O, W=CH, R$_1$=C$_6$H$_{13}$N$_2$O]

Operating as in Example 4 Step 1, but employing 3-{2-[4-(dimethylamino)phenoxy]-4,6-dihydroxyphenyl}isoxazole-5-carboxylic acid instead of 3-[2,4-dihydroxy-6-(4-nitrophenoxy)phenyl]isoxazole-5-carboxylic acid and 1-methyl-piperidin-4-ylamine instead of tert-butyl (2-aminoethyl) methylcarbamate, the title compound was obtained in 84% yield.

$^1$H NMR (401 MHz, DMSO-d$_6$) δ ppm 1.61 (m, 2H) 1.75 (m, 2H) 2.02 (m, 2H) 2.20 (br. s., 3H) 2.82 (m, 2H) 2.87 (s, 6H) 3.63-3.82 (m, 1H) 5.65 (d, 1H) 5.97-6.24 (m, 1H) 6.59-6.82 (m, 2H) 6.83-6.92 (m, 2H) 7.15 (s, 1H) 8.76 (d, 1H) 9.67 (s, 1H) 9.84 (s, 1H).

EXAMPLE 55

Tert-butyl-4-{[(3-{2-[4-(dimethylamino)phenoxy]-4,6-dihydroxyphenyl}isoxazol-5-yl)carbonyl]amino}piperidine-1-carboxylate

[(I); (Z)—R=4-(Dimethylamino)phenoxy, X=N, Y=O, W=CH, R$_1$=C$_{10}$H$_{19}$N$_2$O$_3$]

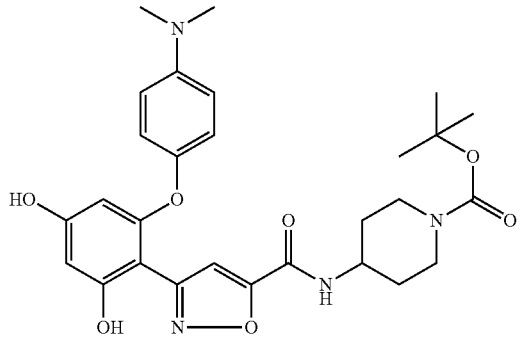 [SMILES: CN(C)c1ccc(Oc2cc(O)cc(O)c2-c2cc(C(=O)NC3CCN(C(=O)OC(C)(C)C)CC3)on2)cc1]

Operating as in Example 4 Step 1 and 2, but employing 3-{2-[4-(dimethylamino)phenoxy]-4,6-dihydroxyphenyl}isoxazole-5-carboxylic acid instead of 3-[2,4-dihydroxy-6-(4-nitrophenoxy)phenyl]isoxazole-5-carboxylic and 4-amino-piperidine-1-carboxylic acid tert-butyl ester instead of tert-butyl (2-aminoethyl)methylcarbamate, the title compound was obtained in 72% yield.

EXAMPLE 56

3-{2-[4-(Dimethylamino)phenoxy]-4,6-dihydroxyphenyl}-N-(piperidin-4-yl)isoxazole-5-carboxamide Dihydrochloride

[(I); (Z)—R=4-(Dimethylamino)phenoxy, X=N, Y=O, W=CH, R$_1$=C$_6$H$_{11}$N$_2$O]

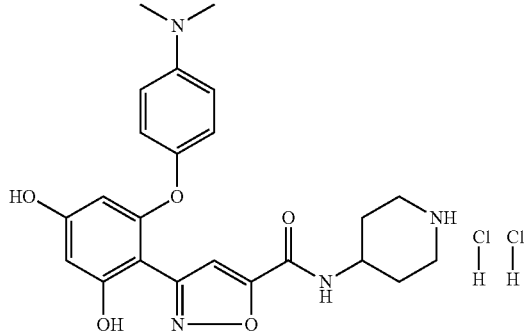

To a stirred solution of tert-butyl 4-{[(3-{2-[4-(dimethylamino)phenoxy]-4,6-dihydroxyphenyl}isoxazol-5-yl)carbonyl]amino}piperidine-1-carboxylate (5.4 g, 10 mmol) in dioxane (20 mL) was added 4 M HCl solution in dioxane (30 mL). After stirring for 3 hours, the precipitate was filtered off, washed with diethyl ether and dried to afford the title compound (3.8 g, 86% yield).

EXAMPLE 57

3-{2-[4-(Dimethylamino)phenoxy]-4,6-dihydroxyphenyl}-N-[1-(1,4-dioxaspiro[4.5]dec-8-yl)piperidin-4-yl]isoxazole-5-carboxamide

[(I); (Z)—R=4-(Dimethylamino)phenoxy, X=N, Y=O, W=CH, $R_1=C_{14}H_{23}N_2O_3$]

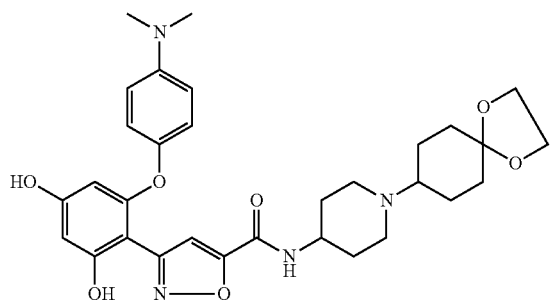 [SMILES: CN(C)c1ccc(Oc2cc(O)cc(O)c2-c2cc(C(=O)NC3CCN(C4CCC5(CC4)OCCO5)CC3)on2)cc1]

Operating as in Example 26, but employing 3-{2-[4-(dimethylamino)phenoxy]-4,6-dihydroxyphenyl}-N-(piperidin-4-yl)isoxazole-5-carboxamide dihydrochloride instead of 5-[3,5-dihydroxy-2-(4-(dimethylamino)phenoxy)phenyl]-N-(piperidin-4-yl)isoxazole-3-carboxamide dihydrochloride, the title compound was obtained in 58% yield.

$^1$H NMR (400 MHz, DMSO-$d_6$) δ ppm 2.85-2.88 (m, 6H) 3.70-3.80 (m, 1H) 3.84 (s, 3H) 5.65 (d, 1H) 6.11 (d, 1H) 6.70-6.78 (m, 2H) 6.86-6.94 (m, 2H) 7.14 (s, 1H) 8.77 (br. s., 1H) 9.67 (s, 1H) 9.84 (s, 1H).

EXAMPLE 58

3-{2-[4-(Dimethylamino)phenoxy]-4,6-dihydroxyphenyl}-N-[1-(3,3-dimethyl-1,5-dioxaspiro[5.5]undec-9-yl)piperidin-4-yl]isoxazole-5-carboxamide

[(I); (Z)—R=4-(Dimethylamino)phenoxy, X=N, Y=O, W=CH, $R_1=C_{17}H_{26}N_2O_3$]

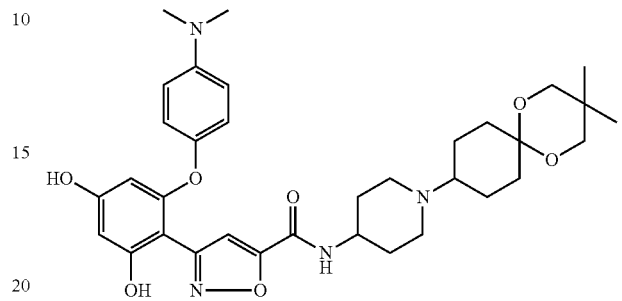

Operating as in Example 28, but employing 3-{2-[4-(dimethylamino)phenoxy]-4,6-dihydroxyphenyl}-N-(piperidin-4-yl)isoxazole-5-carboxamide dihydrochloride instead of 5-[3,5-dihydroxy-2-(4-(dimethylamino)phenoxy)phenyl]-N-(piperidin-4-yl)isoxazole-3-carboxamide dihydrochloride, the title compound was obtained in 62% yield.

$^1$H NMR (400 MHz, DMSO-$d_6$) δ ppm 0.87-0.92 (m, 6H) 1.30 (br. s., 2H) 1.50 (br. s., 2H) 2.83-2.88 (m, 6H) 3.39-3.46 (m, 4H) 3.95 (br. s., 1H) 5.60-5.69 (m, 1H) 6.12 (d, 1H) 6.69-6.78 (m, 2H) 6.83-6.94 (m, 2H) 7.16 (s, 1H) 8.92 (br. s., 1H) 9.66-9.71 (m, 1H) 9.86 (s, 1H).

EXAMPLE 59

5-[2,4-Dihydroxy-6-(benzyloxy)phenyl]-N-ethyl isoxazole-3-carboxamide

[(I); (Z)—R=Benzyloxy, X=O, Y=N, W=CH, $R_1=C_3H_6NO$]

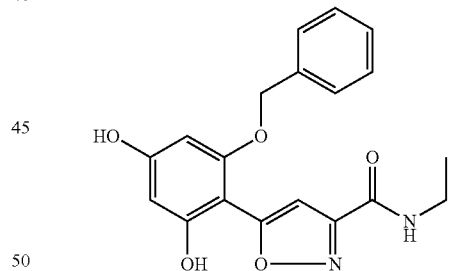

Scheme

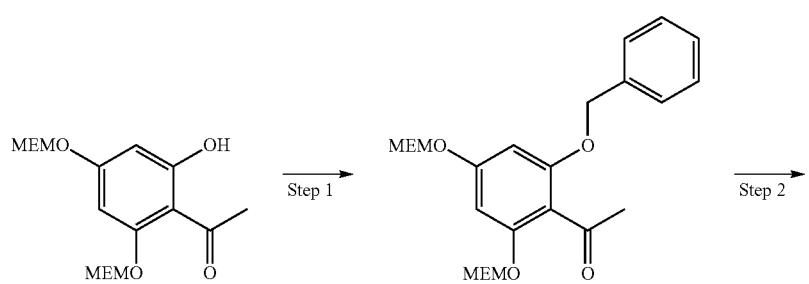

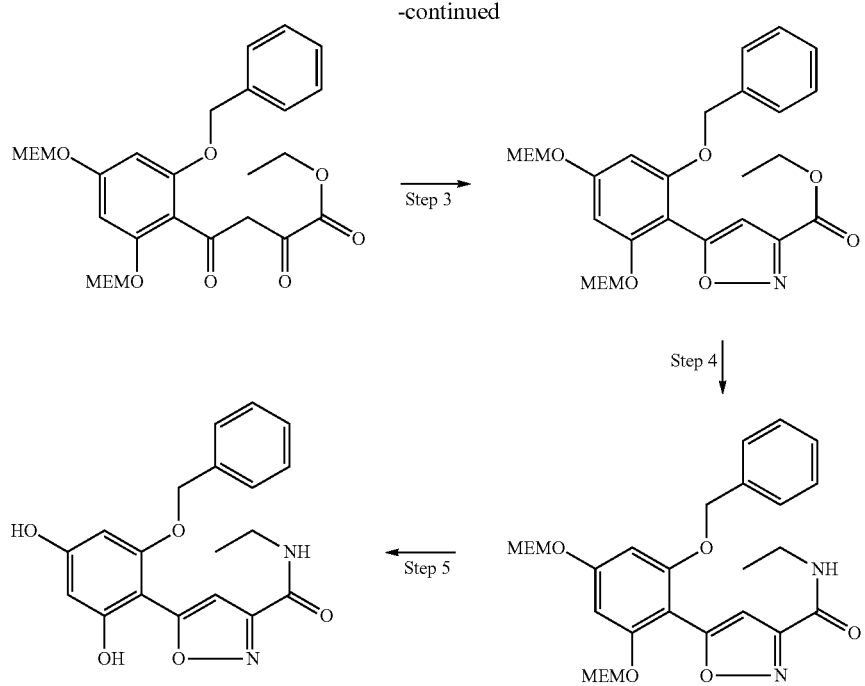

Step 1

1-{2-(Benzyloxy)-4,6-bis[(2-methoxyethoxy)methoxy]phenyl}ethanone

To a stirred suspension of 1-{2-hydroxy-4,6-bis[(2-methoxyethoxy)methoxy]phenyl}ethanone (3.53 g, 10 mmol), potassium carbonate (1.7 g, 14 mmol) in DMF (15 mL) was added benzylbromide (2.1 g, 12 mmol). After stirring overnight, the reaction mixture was diluted with ethyl acetate (100 mL) and thoroughly washed with brine. The organic phase was dried and evaporated to dryness. The crude was chromatographed on a small pad of silica gel eluting with hexane/ethyl acetate 7/1, to provide the title compound (g 3.25, yield 73%).

$^1$H NMR (400 MHz, DMSO-$d_6$) δ ppm 2.35 (s, 3H) 3.22 (s, 3H) 3.25 (s, 3H) 3.37 (t, 4H) 3.39 (t, 4H) 3.51 (t, 3H) 3.53 (t, 3H) 5.22 (s, 2H) 6.47 (bs, 1H) 6.49 (bs, 1H) 7.32-7.40 (m, 5H).

Step 2

Ethyl 4-{2-(benzyloxy)-4,6-bis[(2-methoxyethoxy)methoxy]phenyl}-2,4-dioxobutanoate Operating as in Example 1 Step 2, but employing 1-{2-(benzyloxy)-4,6-bis[(2-methoxyethoxy)methoxy]phenyl}ethanone instead of 1-[2,4-bis(benzyloxy)-6-(4-nitrophenoxy)phenyl]ethanone, the title compound was obtained in 83% yield.

$^1$H NMR (400 MHz, DMSO-$d_6$) δ ppm 1.13 (t, 3H) 4.17 (bs, 1H) 3.21 (s, 3H) 3.26 (s, 3H) 3.36 (t, 4H) 3.37 (t, 4H) 3.52 (t, 3H) 3.54 (t, 3H) 3.81 (q, 2H) 5.21 (s, 2H) 6.49 (bs, 1H) 6.48 (bs, 1H) 7.34-7.46 (m, 5H).

Step 3

Ethyl 5-{2-(benzyloxy)-4,6-bis[(2-methoxyethoxy)methoxy]phenyl}isoxazole-3-carboxylate Operating as in Example 1 Step 3, but employing ethyl 4-{2-(benzyloxy)-4,6-bis[(2-methoxyethoxy)methoxy]phenyl}-2,4-dioxobutanoate instead of ethyl 4-[2,4-bis(benzyloxy)-6-(4-nitrophenoxy)phenyl]-2,4-dioxobutanoate, the title compound was obtained in 48% yield.

$^1$H NMR (400 MHz, DMSO-$d_6$) δ ppm 1.44 (t, 3H) 3.35 (s, 2H) 3.37 (s, 3H) 3.55-3.59 (m, 4H) 3.81-3.84 (m, 4H) 4.48 (q, 2H) 5.10 (st, 2H) 5.19 (s, 2H) 5.29 (s, 2H) 6.46 (d, 1H) 6.48 (d, 1H) 7.10 (s, 1H) 7.28-7.44 (m, 5H).

Step 4

5-{2-(Benzyloxy)-4,6-bis[(2-methoxyethoxy)methoxy]phenyl}-N-ethylisoxazole-3-carboxamide Operating as in Example 1 Step 4, but employing ethyl 5-{2-(benzyloxy)-4,6-bis[(2-methoxyethoxy)methoxy]phenyl}isoxazole-3-carboxylate instead of ethyl 5-[2,4-bis(benzyloxy)-6-(4-nitrophenoxy)phenyl]isoxazole-3-carboxylate, the title compound was obtained in 68% yield.

$^1$H NMR (400 MHz, DMSO-$d_6$) δ ppm 1.18 (t, 3H) 3.46 (s, 2H) 3.39 (s, 3H) 3.54-3.58 (m, 4H) 3.80-3.83 (m, 4H) 4.47 (q, 2H) 5.11 (st, 2H) 5.18 (s, 2H) 5.31 (s, 2H) 6.48 (d, 1H) 6.51 (d, 1H) 7.13 (s, 1H) 7.28-7.47 (m, 5H) 10.03 (bs, 1H).

Step 5

5-[2,4-Dihydroxy-6-(benzyloxy)phenyl]-N-ethyl isoxazole-3-carboxamide

[(I); (Z)—R=Benzyloxy, X=O, Y=N, W=CH, $R_1$=$C_3H_6NO$]

A solution of 5-{2-(benzyloxy)-4,6-bis[(2-methoxyethoxy)methoxy]phenyl}-N-ethylisoxazole-3-carboxamide (0.35 g, 0.66 mmol), 4M HCl solution (3 mL, 12 mmol) in ethanol (10 mL) was set aside for 3 hours. After concentration, the solution was diluted with ethyl acetate, washed with 1 M NaHCO$_3$ solution then with brine and dried over Na$_2$SO$_4$. After removal of the solvent, the crude was crystallized from small volume of acetone to provide the title compound (0.23 g, 73% yield).

$^1$H NMR (400 MHz, DMSO-d$_6$) δ ppm 1.20 (t, 3H) 3.48 (s, 2H) 5.17 (s, 2H) 6.18-6.25 (2 d, 2H) 7.30-7.44 (m, 5H) 10.11-10.24 (bs, 3H).

EXAMPLE 60

5-[2-(Benzyloxy)-4,6-dihydroxyphenyl]-N-(1-methylpiperidin-4-yl)isoxazole-3-carboxamide

[(I); (Z)—R=Benzyloxy, X=O, Y=N, W=CH, R$_1$=C$_7$H$_{13}$N$_2$O]

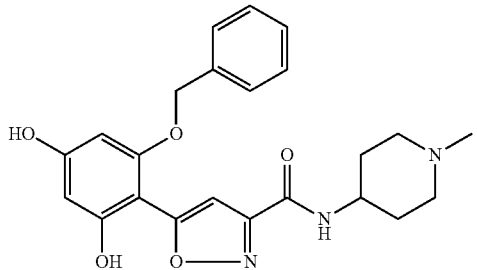 [SMILES: CN1CCC(NC(=O)c2cc(-c3c(O)cc(O)cc3OCc3ccccc3)on2)CC1]

Operating as in Example 59 Step 4 and 5, but employing neat 1-methyl-piperidin-4-ylamine instead of a solution of ethylamine, the title compound was obtained in 37% yield.

$^1$H NMR (400 MHz, DMSO-d$_6$) δ ppm 1.49-1.67 (m, 2H) 1.67-1.76 (m, 2H) 1.85-2.00 (m, 2H) 2.15 (s, 3H) 2.71-2.79 (m, 2H) 3.63-3.78 (m, 1H) 5.09 (s, 2H) 6.06-6.12 (m, 2H) 6.72 (s, 1H) 7.25-7.45 (m, 5H) 8.52 (d, 1H) 9.87 (br. s., 1H) 10.05 (br. s., 1H).

EXAMPLE 61

4-(3-Aminoisoxazol-5-yl)-5-(4-nitrophenoxy)benzene-1,3-diol Hydrochloride

[(I); (Z)—R=4-Nitrophenoxy, X=O, Y=N, W=CH, R$_1$=NH$_2$]

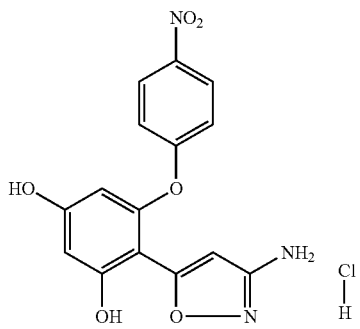 [SMILES: Nc1cc(-c2c(O)cc(O)cc2Oc2ccc([N+](=O)[O-])cc2)on1 ; Cl]

Scheme

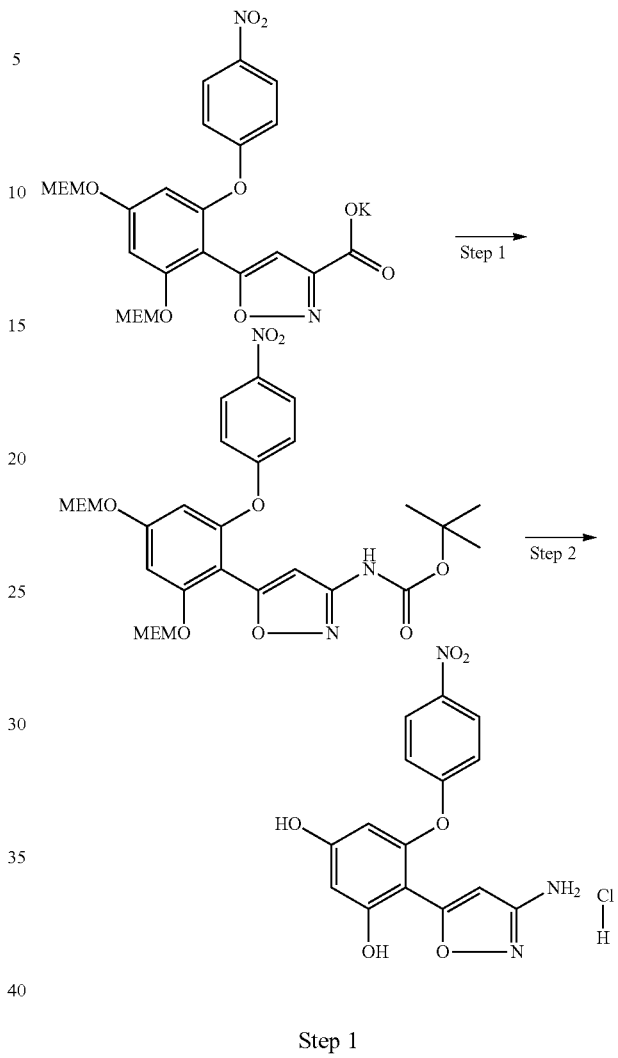

Step 1

Tert-butyl (5-{2,4-bis[(2-methoxyethoxy)methoxy]-6-(4-nitrophenoxy)phenyl}isoxazol-3-yl)carbamate To a stirred suspension of potassium 5-{2,4-bis[(2-methoxyethoxy)methoxy]-6-(4-nitrophenoxy)phenyl}isoxazole-3-carboxylate (12.5 g, 21.8 mmol) in a biphasic system of H$_2$O (50 mL) and ethyl acetate (300 mL) was added dropwise 2 M HCl solution (12 mL, 24 mmol) at 10° C. After stirring for 30 minutes, the layers were separated and the organic phase was dried over Na$_2$SO$_4$. The solvent was removed and the reaction product dissolved in a mixture of dioxane (100 mL) and TEA (3.5 mL, 24 mmol) was treated drop wise with diphenylphosphoryl azide (6.7 g, 24 mmol) at room temperature. After stirring for 25 minutes, the resulting solution was added drop wise to a refluxing mixture of dioxane (100 mL) and tert-butanol (50 mL). After stirring for 1 hour, the solvent was removed and the crude reaction mixture was filtered on a small pad of silica gel eluting with hexane/ethyl acetate 3/2 to provide the title compound (7.3 g, 56% yield).

$^1$H NMR (400 MHz, DMSO-d$_6$) δ ppm 1.49 (s, 9H) 3.35-3.36 (s, 6H) 3.55 (m, 2H) 3.81 (t, 2H) 5.18 (s, 2H) 5.32 (s, 2H) 6.24 (d, 1H) 6.36 (d, 1H) 7.17 (m, 2H) 8.22 (m, 2H) 10.41 (b. s., 1H).

Step 2

4-(3-Aminoisoxazol-5-yl)-5-(4-nitrophenoxy)benzene-1,3-diol Hydrochloride

[(I); (Z)—R=4-Nitrophenoxy, X=O, Y=N, W=CH, $R_1$=$NH_2$]

A stirred solution tert-butyl (5-{2,4-bis[(2-methoxyethoxy)methoxy]-6-(4-nitrophenoxy)phenyl}isoxazol-3-yl)carbamate (12.5 g, 24.2 mmol) and 4 M HCl in dioxane (20 mL) in ethanol (100 mL) was set aside for 5 hours. The solvent was removed and the residue was twice crystallised from a small volume of ethanol/water 3/1 to provide after drying, the title compound (5.2 g, 63% yield).

$^1$H NMR (400 MHz, DMSO-$d_6$) δ ppm 6.22 (d, 1H) 6.37 (d, 1H) 6.75 (s, 1H) 7.95 (d, 2H) 8.22 (dd, 2H) 8.1 (b. s., 3H).

EXAMPLE 62

1-{5-[2,4-Dihydroxy-6-(4-nitrophenoxy)phenyl]isoxazol-3-yl}-3(1-methylpiperidin-4-yl)urea Hydrochloride

[(I); (Z)—R=4-Nitrophenoxy, X=O, Y=N, W=CH, $R_1$=$C_7H_{14}N_3O$]

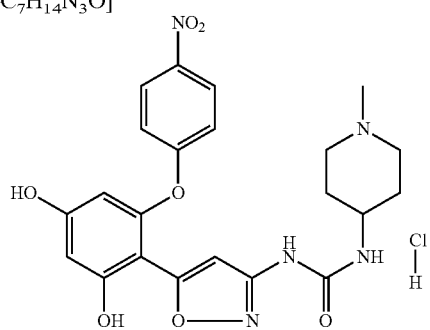

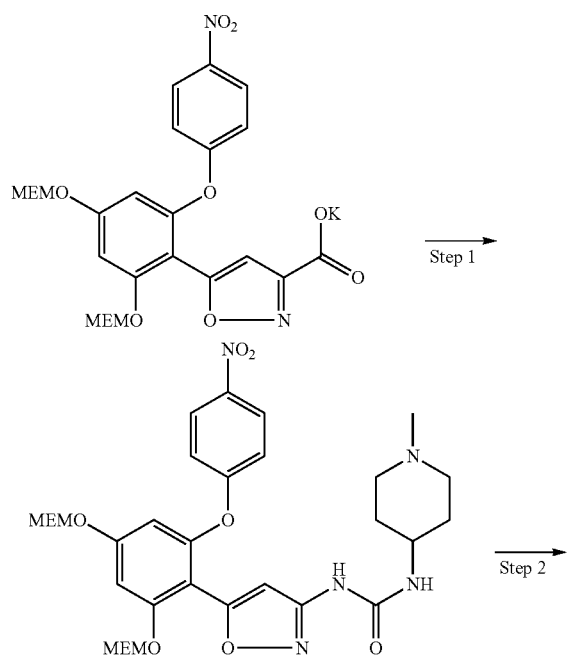

Scheme

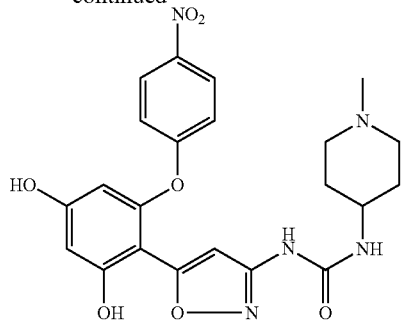

Step 1

1-(5-{2,4-Bis[(2-methoxyethoxy)methoxy]-6-(4-nitrophenoxy)phenyl}isoxazol-3-yl)-3-(1-methylpiperidin-4-yl)urea

[(XXVI); (Z)—R=4-Nitrophenoxy, X=O, Y=N, W=CH, $R_1$=$C_7H_{14}N_3O$]

To a stirred suspension of potassium 5-{2,4-bis[(2-methoxyethoxy)methoxy]-6-(4-nitrophenoxy)phenyl}isoxazole-3-carboxylate (3.1 g, 5.5 mmol) in a biphasic system of $H_2O$ (10 mL) and ethyl acetate (90 mL) was added dropwise 2 M HCl solution (3 mL, 6 mmol) at 10° C. After stirring for 30 minutes, the layers were separated and the organic dried over $Na_2SO_4$. The solvent was removed and the reaction product was dissolved in dioxane (20 mL) containing TEA (0.8 mL, 6 mmol) and treated drop wise with diphenylphosphoryl azide (1.7 g, 6 mmol) at room temperature. After stirring for 30 minutes, the resulting solution was added dropwise to a refluxing dioxane (30 mL). After refluxing for 20 minutes, 1-methyl-piperidin-4-ylamine (0.95 g, 8.25 mmol) was added and the reflux was continued for 30 minutes. After cooling, the solvent was removed and the residue dissolved in ethyl acetate was thoroughly washed with brine. After drying over $Na_2SO_4$ and removal of the solvent, the residue was columned over silica gel eluting with $CH_2Cl_2/CH_3OH$ 8/2 to furnish the title compound (1.67, 47% yield).

$^1$H NMR (400 MHz, DMSO-$d_6$) δ ppm 1.75 (m, 4H) 2.27 (s, 3H) 2.66 (m, 4H) 3.33 (s, 6H) 3.56 (t, 4H) 3.75 (m, 1H) 3.85 (t, 4H) 5.18 (s, 2H) 5.332 (s, 2H) 6.24-6.36 (m, 3H) 7.14-7.22 (m, 3H) 6.24 (dd, 2H) 9.35 (s, 1H).

Step 2

1-{5-[2,4-Dihydroxy-6-(4-nitrophenoxy)phenyl]isoxazol-3-yl}-3(1-methylpiperidin-4-yl)urea Hydrochloride

[(I); (Z)—R=4-Nitrophenoxy, X=O, Y=N, W=CH, $R_1$=$C_7H_{14}N_3O$]

A solution of 1-(5-{2,4-bis[(2-methoxyethoxy)methoxy]-6-(4-nitrophenoxy)phenyl}isoxazol-3-yl)-3-(1-methylpiperidin-4-yl)urea (2.5 g, 3.8 mmol) and 6 M HCl (5 ml, 30 mmol) in ethanol (50 mL) was refluxed for 15 minutes. After concentration to small volume, the title compound was provided (0.76 g, 42% yield).

$^1$H NMR (400 MHz, DMSO-$d_6$) δ ppm 1.89-1.96 (m, 4H) 3.45 (s, 3H) 3.21 (m, 4H) 3.74 (m, 1H) 6.17 (dd, 1H) 6.32 (dd, 1H) 7.25 (b. s., 1H) 7.23 (dd, 2H) 8.25 (dd, 2H) 9.31 (m, 2H) 9.67 (b. s., 1H).

EXAMPLE 63

N-{5-[2,4-Dihydroxy-6-(4-nitrophenoxy)phenyl]isoxazol-3-yl}-1-methylpiperidine-4-carboxamide

[(I); (Z)—R=4-Nitrophenoxy, X=O, Y=N, W=CH, R$_1$=C$_7$H$_{13}$N$_2$O]

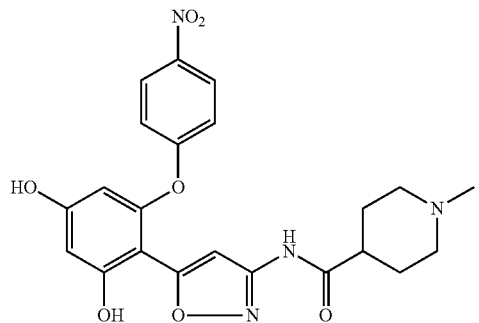 [SMILES: CN1CCC(C(=O)Nc2cc(-c3c(O)cc(O)cc3Oc3ccc([N+](=O)[O-])cc3)on2)CC1]

To a stirred solution of 4-(3-aminoisoxazol-5-yl)-5-(4-nitrophenoxy)benzene-1,3-diol hydrochloride (1.3 g, 4 mmol) in pyridine (35 mL) and TEA (1.68 mL, 12 mmol, 3 eq.) was added portion wise 1-methyl-piperidine-4-carbonyl chloride hydrochloride (0.8 g, 5 mmol) at room temperature. After stirring for 3 hours, 1M NaOH solution (10 mL) was added to hydrolyse any O-acyl derivative. After stirring for 1 hour, 1 M HCl solution (12 mL) was added and the solution was concentrated to small volume before the addition ethyl acetate. The organic phase was thoroughly washed with 2 M NaHCO$_3$, then with brine and dried over Na$_2$SO$_4$. The residue was carefully chromatographed over silica eluting with CH$_2$Cl$_2$/CH$_3$OH/conc. NH$_4$OH solution 80/20/1 to provide the title compound (0.4 g, 22% yield).

$^1$H NMR (400 MHz, DMSO-d$_6$) δ ppm 1.87 (m, 4H) 2.34 (s, 3H) 2.56 (m, 4H) 5.97 (dd, 1H) 6.41 (dd, 1H) 7.22 (dd, 1H9 7.41 (b. s., 1H) 8.25 (dd, 2H) 8.84 (b. s., 2H) 9.25 (s, 1H).

EXAMPLE 64

N-{5-[2,4-Dihydroxy-6-(4-nitrophenoxy)phenyl]isoxazol-3-yl}ethanesulfonamide

[(I); (Z)—R=4-Nitrophenoxy, X=O, Y=N, W=CH, R$_1$=C$_2$H$_6$NO$_2$S]

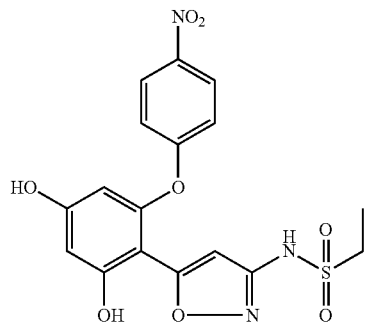 [SMILES: CCS(=O)(=O)Nc1cc(-c2c(O)cc(O)cc2Oc2ccc([N+](=O)[O-])cc2)on1]

Operating as in Example 42, but employing ethanesulphonyl chloride instead of 1-methyl-piperidine-4-carbonyl chloride hydrochloride, the title compound was obtained in 27% yield.

$^1$H NMR (400 MHz, DMSO-d$_6$) δ ppm 1.41 (t, 3H) 3.32 (q, 2H) 5.97 (dd, 1H) 6.41 (dd, 1H) 7.22 (dd, 1H9 7.41 (b. s., 1H) 8.25 (dd, 2H) 8.84 (b. s., 2H) 9.11 (s, 1H).

EXAMPLE 65

3-[2,4-Dihydroxy-6-(4-nitrophenoxy)phenyl]-N-(2-hydroxyethyl)-1H-pyrazole-5-carboxamide

[(I); (Z)—R=4-Nitrophenoxy, X=N, Y=N, W=CH, R$_1$=C$_3$H$_6$NO$_2$]

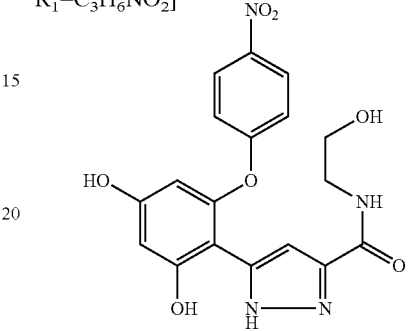

Scheme

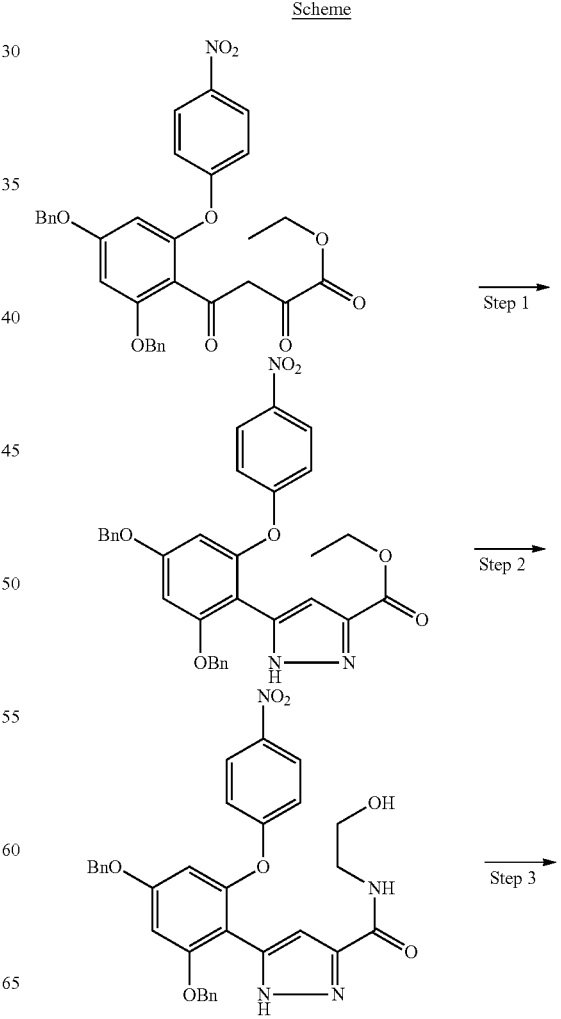

113
-continued

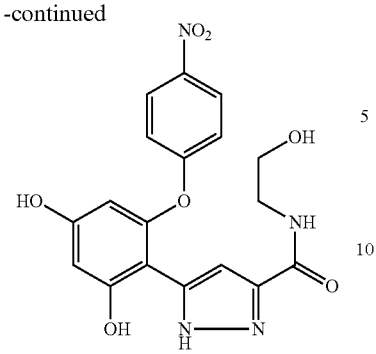

Step 1

Ethyl 3-[2,4-bis(benzyloxy)-6-(4-nitrophenoxy)phenyl]-1H-pyrazole-5-carboxylate

A stirred solution of ethyl 4-[2,4-bis(benzyloxy)-6-(4-nitrophenoxy)phenyl]-2,4-dioxobutanoate (1 g, 1.75 mmol) and hydrazine hydrate (0.25 mL, 4.4 mmol) in ethanol (20 mL) was refluxed for 1 hour. The formed precipitate was filtered off and washed with ethanol and dried, to afford the title compound (0.69 g, 70% yield).

$^1$H NMR (40 MHz, DMSO-$d_6$) δ ppm 1.23 (t, 3H) 4.16-4.25 (m, 2H) 5.14 (s, 2H) 5.21 (s, 2H) 6.54 (d, 1H) 6.86 (d, 1H) 7.05 (s, 2H) 7.25-7.49 (m, 10H) 8.15-8.20 (m, 2H).

Step 2

5-[2,4-Bis(benzyloxy)-6-(4-nitrophenoxy)phenyl]-N-(2-hydroxyethyl)-1H-pyrazole-3-carboxamide Operating as in Example 2, but employing ethyl 3-[2,4-bis(benzyloxy)-6-(4-nitrophenoxy)phenyl]-1H-pyrazole-5-carboxylate instead of ethyl 5-[2,4-bis(benzyloxy)-6-(4-nitrophenoxy)phenyl]isoxazole-3-carboxylate, the title compound was obtained in 75% yield.

$^1$H NMR (40 MHz, DMSO-$d_6$) δ ppm 3.52 (q, 2H) 4.75 (t, 1H) 5.13 (s, 2H) 5.19 (s, 2H) 5.83 (s, 2H) 6.67 (s, 1H) 7.28-7.45 (m, 10H) 7.63 (d, 2H) 8.17 (t, 1H) 8.26 (d, 2H) 9.38 (s, 2H) 9.40 (s, 1H).

Step 3

5-[2,4-Dihydroxy-6-(4-nitrophenoxy)phenyl]-N-(2-hydroxyethyl)-1H-pyrazole-3-carboxamide

[(I); (Z)—R=4-Nitrophenoxy, X=N, Y=N, W=CH, R$_1$=C$_3$H$_6$NO$_2$]

Operating as in Example 1 Step 5, but employing 5-[2,4-bis(benzyloxy)-6-(4-nitrophenoxy)phenyl]-N-(2-hydroxyethyl)-1H-pyrazole-3-carboxamide instead of 5-[2,4-bis(benzyloxy)-6-(4-nitrophenoxy)phenyl]-N-ethylisoxazole-3-carboxamide, the title compound was obtained in 58% yield.

$^1$H NMR (400 MHz, DMSO-$d_6$) δ ppm 3.52 (q, 2H) 4.75 (t, 1H) 5.83 (s, 2H) 6.67 (s, 1H) 7.63 (d, 2H) 8.17 (t, 1H) 8.26 (d, 2H) 9.38 (s, 2H) 9.40 (s, 1H).

114

EXAMPLE 66

5-[2,4-Dihydroxy-6-(4-nitrophenoxy)phenyl]-N-(2-fluoroethyl)-1H-pyrazole-3-carboxamide

[(I); (Z)—R=4-Nitrophenoxy, X=N, Y=N, W=CH, R$_1$=C$_3$H$_6$FNO]

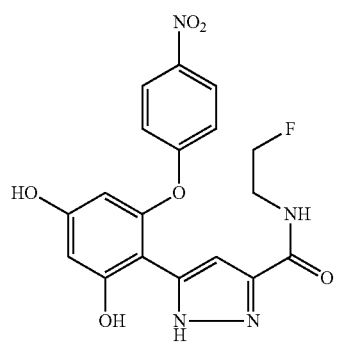 [SMILES: O=C(NCCF)c1cc(-c2c(O)cc(O)cc2Oc2ccc([N+](=O)[O-])cc2)[nH]n1]

Scheme

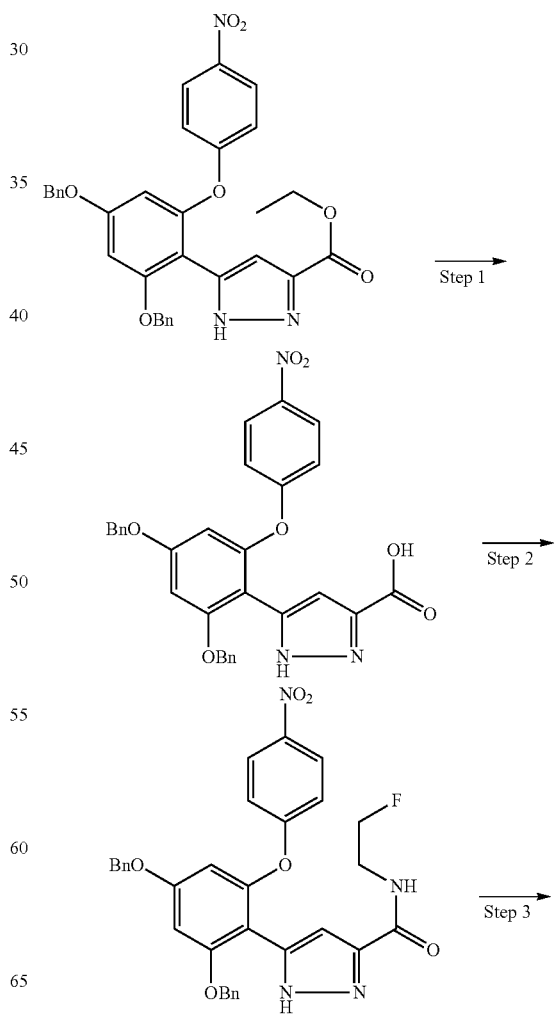

-continued

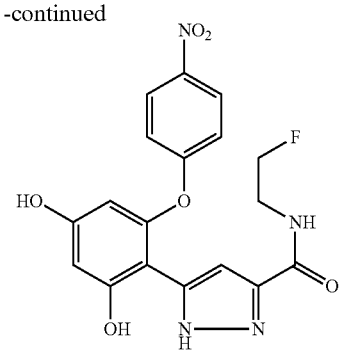

Step 1

5-[2,4-Bis(benzyloxy)-6-(4-nitrophenoxy)phenyl] pyrazole-3-carboxylic acid

Operating as in Example 3 Step 1, but employing ethyl 5-[2,4-bis(benzyloxy)-6-(4-nitrophenoxy)phenyl]pyrazole-3-carboxylate instead of ethyl 5-[2,4-bis(benzyloxy)-6-(4-nitrophenoxy)phenyl]isoxazole-3-carboxylate, the title compound was obtained in 76% yield.
$^1$H NMR (400 MHz, DMSO-$d_6$) δ ppm 4.19 (bs, 1H) 5.12 (s, 2H) 5.27 (s, 2H) 6.5 (bs, 1H) 7.36 (bs, 1H) 7.18 (bs, 2H) 7.78-7.37 (m, 10H) 8.65 (bs, 1H).

Step 2

5-[2,4-Bis(benzyloxy)-6-(4-nitrophenoxy)phenyl]-N-(2-fluoroethyl)pyrazole-3-carboxamide Operating as in Example 3 Step 2, but employing 5-[2,4-bis(benzyloxy)-6-(4-nitrophenoxy)phenyl]pyrazole-3-carboxylic acid instead of 5-[2,4-bis(benzyloxy)-6-(4-nitrophenoxy)phenyl]isoxazole-3-carboxylic acid, the title compound was obtained in 48% yield.
$^1$H NMR (400 MHz, DMSO-$d_6$) δ ppm 3.48 (m, 2H) 4.48 (bs, 2H) 5.13 (s, 2H) 5.22 (s, 2H) 6.5 (bs, 1H) 7.15 (bs, 2H) 6.84 (bs, 1H) 7.35-7.46 (m, 10H) 8.2 (bs, 1H) 8.24 (bs, 1H) 8.83 (bs, 1H).

Step 3

5-[2,4-Dihydroxy-6-(4-nitrophenoxy)phenyl]-N-(2-fluoroethyl)pyrazole-3-carboxamide

[(I); (Z)—R=4-Nitrophenoxy, X=N, Y=N, W=CH, $R_1=C_3H_6FNO$]
Operating as in Example 3 Step 3, but employing 5-[2,4-bis(benzyloxy)-6-(4-nitrophenoxy)phenyl]-N-(2-fluoroethyl)pyrazole-3-carboxamide instead of 5-[2,4-bis(benzyloxy)-6-(4-nitrophenoxy)phenyl]-N-(2-fluoroethyl) pyrazole-3-carboxamide, the title compound was obtained in 89% yield.
$^1$H NMR (400 MHz, DMSO-$d_6$) δ ppm 3.50-3.65 (m, 2H) 4.45-4.64 (m, 2H) 5.84 (s, 2H) 6.69 (s, 1H) 7.61-7.68 (m, 2H) 8.22-8.31 (m, 2H) 8.48 (t, 1H) 9.35-9.43 (m, 2H).

Analytical Method 1:
Analyses were performed on a Waters Acquity HPLC™ System equipped with a 2996 PDA (UV-VIS), and Acquity ELSD™ detectors. The LC system was coupled to a Waters Acquity 3100 SQD™ single quadrupole mass spectrometer for atomic mass determinations. A Waters Acquity HPLC™ BEH C18, 1.7 μm, 2.1×50 mm column at 45° C. was used with a flow rate of 0.7 mL/min of the following binary solvent system and gradient.
Mobile Phase A: 0.1% Trifluoracetic Acid in H$_2$O/Acetonitrile (95:5)
Mobile Phase B: Acetonitrile/H$_2$O (95:5)

| Time (min) | Phase A | Phase B |
|---|---|---|
| 0.00 | 95% | 5% |
| 2.00 | 5% | 95% |

Analytical Method 2:
Analyses were performed on a Waters Alliance HT 2795 System equipped with a 996 PDA (UV-VIS), and S.E. D.E.R.E. SEDEX 55, ELSD, detectors. The LC system was coupled to a Waters/Micromass ZQ™ single quadrupole mass spectrometer for atomic mass determinations. A Waters Atlantis dC18, 3 μm, 4.6×50 mm column was used with a flow rate of 1.4 mL/min of the following binary solvent system and gradient.
Mobile Phase A: Ammonium Acetate 5 mM/Acetonitrile (95:5)—pH 5.2
Mobile Phase B: Acetonitrile/H$_2$O (95:5)

| Time (min) | % Phase A | % Phase B |
|---|---|---|
| 0.00 | 95% | 5% |
| 3.00 | 25% | 75% |
| 3.10 | 0% | 100% |

Analytical Method 3:
Analyses were performed on a Waters Alliance HT 2795 System equipped with a 996 PDA (UV-VIS) detector. The LC system was coupled to a Waters/Micromass ZQ™ single quadrupole mass spectrometer for atomic mass determinations. A Waters Ascentis Express C18, 2.7 μm, 4.6×50 mm column was used with a flow rate of 1.0 mL/min of the following binary solvent system and gradient.
Mobile Phase A: 0.1% Trifluoracetic Acid in H$_2$O/Acetonitrile (95:5)
Mobile Phase B: Acetonitrile/H$_2$O (95:5)

| Time (min) | % Phase A | % Phase B |
|---|---|---|
| 0.00 | 90% | 10% |
| 4.00 | 10% | 90% |
| 4.10 | 0% | 100% |

Mass Spectrometer Parameters: (Method 1)

| | |
|---|---|
| Ionization Mode | ESI+ and ESI− |
| Capillary Voltage | 3 kV (ES+); 3 kV (ES−) |
| Cone Voltage | 30 V (ES+); 30 V (ES−) |
| Extractor Voltage | 1 V |
| RF Lens Voltage | 0.1 V |
| Source Temperature | 120° C. |
| Desolvation Temperature | 350° C. |
| Cone Gas Flow | 100 L/Hr |
| Desolvation Gas Flow | 600 L/Hr. |
| LM Resolution | 15.0 |
| HM Resolution | 15.0 |
| Ion Energy | 0.3 |
| Gain | 1 |
| Scan Mode | Full Scan (Range = 100-800 m/z) ScanTime = 0.1 s Inter-Scan Delay = 0.02 s |

Mass Spectrometer Parameters: (Methods 2 & 3)

| | |
|---|---|
| Ionization Mode | ESI+ and ESI− |
| Capillary Voltage | 3.48 kV (ES+); 2.76 kV (ES−) |
| Cone Voltage | 15 V (ES+); 27 V (ES−) |
| Extractor Voltage | 1 V |
| RF Lens Voltage | 0.1 V |
| Source Temperature | 120° C. |
| Desolvation Temperature | 240° C. |
| Cone Gas Flow | 100 L/Hr |
| Desolvation Gas Flow | 600 L/Hr |
| LM Resolution | 15.0 |
| HM Resolution | 15.0 |
| Ion Energy | 0.5 |
| Multiplier | 600 |
| Scan Mode | Full Scan (Range = 100-800 m/z) ScanTime = 0.5 s Inter-Scan Delay = 0.3 s |

Semi-Preparative HPLC Method:

All purifications were performed on a Biotage Paraflex Flex System, equipped with four independent, binary flow-stream pumps, a UV detector with four-channel flow cell monitoring two wavelengths (220 and 254 nm), and four fraction collectors. Fractionation was performed at 254 nm. Waters XTerra Prep RP18, 5 μm, 100×19 mm columns were used at a flow rate of 20 mL/min. Gradients were applied according to the retention time of the desired product obtained from the analytical HPLC analysis.

Standard Binary Solvent System:
Mobile Phase A: 0.1% Trifluoracetic Acid in $H_2O$/Acetonitrile (95:5)
Mobile Phase B: Acetonitrile Gradient A:

| Time (min) | % Phase A | % Phase B |
|---|---|---|
| 0.0 | 100% | 0% |
| 6.0 | 80% | 20% |
| 8.0 | 80% | 50% |
| 8.5 | 50% | 100% |

Gradient B:

| Time (min) | % Phase A | % Phase B |
|---|---|---|
| 0.0 | 100% | 0% |
| 6.0 | 70% | 30% |
| 8.0 | 0% | 100% |

Gradient C:

| Time (min) | % Phase A | % Phase B |
|---|---|---|
| 0.0 | 100% | 0% |
| 6.0 | 50% | 50% |
| 8.0 | 0% | 100% |

Gradient D:

| Time (min) | % Phase A | % Phase B |
|---|---|---|
| 0.0 | 90% | 10% |
| 6.0 | 30% | 70% |
| 8.0 | 0% | 100% |

The invention claimed is:

1. A compound of the formula (I):

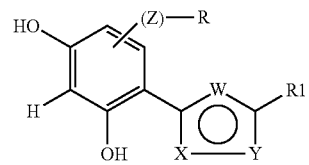

wherein:
Z is —CH=CH—, —$(CH_2)_p$, wherein p is 0, 1, 2 or 3, NH, O, S, >S=O, >$SO_2$ or >C=O;
R is an optionally substituted linear or branched $C_1$-$C_7$ alkyl, $C_2$-$C_7$ alkenyl or $C_2$-$C_7$ alkynyl, $C_3$-$C_7$ cycloalkyl, $C_4$-$C_7$ cycloalkenyl, phenyl, naphthyl, 5 or 6 membered heteroaryl, saturated or partially saturated heterocyclic ring comprising one or more oxygen, sulfur or nitrogen atom, or is a group $CONHR_2$, $CH_2NHR_2$, $NHCOR_2$, $NHCONHR_2$ wherein $R_2$ is an optionally substituted linear or branched $C_1$-$C_7$ alkyl, $C_2$-$C_7$ alkenyl or $C_2$-$C_7$ alkynyl, $C_3$-$C_7$ cycloalkyl, $C_4$-$C_7$ cycloalkenyl group, phenyl, naphthyl, 5 or 6 membered heteroaryl, saturated or partially saturated heterocyclic ring comprising one or more oxygen, sulfur or nitrogen atom;
X, Y and W are respectively O, N and CH, or
X, Y and W are respectively N, O and CH;
$R_1$ is $NH_2$, $NHCONHR_2$, $NHCOR_2$, $NHSO_2R_2$, or $CONHR_2$ group, wherein $R_2$ is as defined above; the ring containing X, Y and W as defined above being a heteroaryl group, or a pharmaceutically acceptable salt thereof with the proviso that when Z is —$(CH_2)_p$ and p is 0, then R is not $C_2$ alkyl and wherein p is 1, then R is not $C_1$ alkyl.

2. A compound of the formula (I):

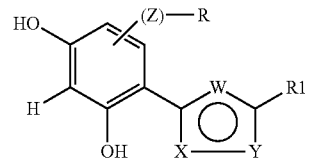

wherein:
Z is —$(CH_2)_p$, wherein p is 0 or 1, or O;
R is an optionally substituted phenyl;
X, Y and W are respectively O, N and CH, or
X, Y and W are respectively N, O and CH;
$R_1$ is $NH_2$, $NHCONHR_2$, $NHCOR_2$, $NHSO_2R_2$, or $CONHR_2$ group, wherein $R_2$ is an optionally substituted linear or branched $C_1$-$C_7$ alkyl or an optionally substituted saturated or partially saturated heterocyclic ring comprising one or more oxygen, sulfur or nitrogen atom;
the ring containing X, Y and W as defined above being a heteroaryl group;
or a pharmaceutically acceptable salt thereof.

3. A compound which is selected from:
5-[2,4-dihydroxy-6-(4-nitrophenoxy)phenyl]-N-ethyl-isoxazole-3-carboxamide,
5-[2-(4-chlorophenoxy)-4,6-dihydroxyphenyl]-N-ethyl-isoxazole-3-carboxamide, N-[1-(4,4-difluorocyclohexyl)piperidin-4-yl]-3-[2,4-dihydroxy-6-(4-nitrophenoxy)phenyl]isoxazole-5-carboxamide,
N-(1-azabicyclo[2.2.2]oct-3-yl)-5-[2,4-dihydroxy-6-(4-nitrophenoxy)phenyl]isoxazole-3-carboxamide,
5-[2,4-dihydroxy-6-(4-nitrophenoxy)phenyl]-N-(2-hydroxyethyl)isoxazole-3-carboxamide,
5-[2,4-dihydroxy-6-(4-nitrophenoxy)phenyl]-N-[2-(dimethylamino)ethyl]isoxazole-3-carboxamide,
5-[2,4-dihydroxy-6-(4-nitrophenoxy)phenyl]-N-(2,2,2-trifluoroethyl)isoxazole-3-carboxamide,
5-[2,4-dihydroxy-6-(4-nitrophenoxy)phenyl]-N-[2-(4-hydroxyphenyl)ethyl]isoxazole-3-carboxamide,
5-[2,4-dihydroxy-6-(4-nitrophenoxy)phenyl]-N-(1-methylpiperidin-4-yl)isoxazole-3-carboxamide,
5-[2,4-dihydroxy-6-(4-nitrophenoxy)phenyl]-N-(3-hydroxypropyl)isoxazole-3-carboxamide,
5-[2,4-dihydroxy-6-(4-nitrophenoxy)phenyl]-N-(2-methoxyethyl)isoxazole-3-carboxamide,
5-[2,4-dihydroxy-6-(4-nitrophenoxy)phenyl]-N-(3-methoxypropyl)isoxazole-3-carboxamide,
5-[2,4-dihydroxy-6-(4-nitrophenoxy)phenyl]-N-(2-fluoroethyl)isoxazole-3-carboxamide,
N-[2-(acetylamino)ethyl]-5-[2,4-dihydroxy-6-(4-nitrophenoxy)phenyl]isoxazole-3-carboxamide,
5-[2,4-dihydroxy-6-(4-nitrophenoxy)phenyl]-N-[3-(dimethylamino)propyl]isoxazole-3-carboxamide,
5-[2,4-dihydroxy-6-(4-nitrophenoxy)phenyl]-N-[2-(1-methylpyrrolidin-2-yl)ethyl]isoxazole-3-carboxamide,
5-[2,4-dihydroxy-6-(4-nitrophenoxy)phenyl]-N-[(1-methylpiperidin-4-yl)methyl]isoxazole-3-carboxamide,
N-(azetidin-3-ylmethyl)-5-[2,4-dihydroxy-6-(4-nitrophenoxy)phenyl]isoxazole-3-carboxamide,
5-[2,4-dihydroxy-6-(4-nitrophenoxy)phenyl]-N,N-dimethylisoxazole-3-carboxamide,
5-[2-(4-aminophenoxy)-4,6-dihydroxyphenyl]-N-ethylisoxazole-3-carboxamide,
5-[2,4-dihydroxy-6-(4-nitrophenoxy)phenyl]-N-(furan-2-ylmethyl)isoxazole-3-carboxamide,
N-benzyl-5-[2,4-dihydroxy-6-(4-nitrophenoxy)phenyl]isoxazole-3-carboxamide,
N-(cyclohexylmethyl)-5-[2,4-dihydroxy-6-(4-nitrophenoxy)phenyl]isoxazole-3-carboxamide,
5-[2,4-dihydroxy-6-(4-nitrophenoxy)phenyl]-N-[3-(1H-imidazol-1-yl)propyl]isoxazole-3-carboxamide,
5-[2,4-dihydroxy-6-(4-nitrophenoxy)phenyl]-N-[2-(piperidin-1-yl)ethyl]isoxazole-3-carboxamide,
5-[2,4-dihydroxy-6-(4-nitrophenoxy)phenyl]-N-[2-(morpholin-4-yl)ethyl]isoxazole-3-carboxamide,
5-[2,4-dihydroxy-6-(4-nitrophenoxy)phenyl]-N-[3-(2-oxopyrrolidin-1-yl)propyl]isoxazole-3-carboxamide,
5-[2,4-dihydroxy-6-(4-nitrophenoxy)phenyl]-N-[3-(4-methylpiperazin-1-yl)propyl]isoxazole-3-carboxamide, tert-butyl,
{2-[({5-[2,4-dihydroxy-6-(4-nitrophenoxy)phenyl]isoxazol-3-yl}carbonyl)amino]ethyl}methylcarbamate,
N-(trans-4-aminocyclohexyl)-5-[2,4-dihydroxy-6-(4-nitrophenoxy)phenyl]isoxazole-3-carboxamide,
5-[2,4-dihydroxy-6-(4-nitrophenoxy)phenyl]-N-(trans-4-hydroxycyclohexyl)isoxazole-3-carboxamide,
tert-butyl 4-[({5-[2,4-dihydroxy-6-(4-nitrophenoxy)phenyl]isoxazol-3-yl}carbonyl)amino]piperidine-1-carboxylate,
5-[2,4-dihydroxy-6-(4-nitrophenoxy)phenyl]-N-(piperidin-4-yl)isoxazole-3-carboxamide,
N-cyclohexyl-5-[2,4-dihydroxy-6-(4-nitrophenoxy)phenyl]isoxazole-3-carboxamide,
5-[2,4-dihydroxy-6-(4-nitrophenoxy)phenyl]-N-[2-(methylamino)ethyl]isoxazole-3-carboxamide,
5-{2-[4-(benzylamino)phenoxy]-4,6-dihydroxyphenyl}-N-ethylisoxazole-3-carboxamide,
5-{2-[4-(acetylamino)phenoxy]-4,6-dihydroxyphenyl}-N-ethylisoxazole-3-carboxamide,
5-[2-(4-amino-3-chlorophenoxy)-4,6-dihydroxyphenyl]-N-ethylisoxazole-3-carboxamide,
5-{2-[4-(dimethylamino)phenoxy]-4,6-dihydroxyphenyl}-N-ethylisoxazole-3-carboxamide,
5-{2,4-dihydroxy-6-[4-(propan-2-ylamino)phenoxy]phenyl}-N-ethylisoxazole-3-carboxamide,
5-[2,4-dihydroxy-6-(4-nitrophenoxy)phenyl]-N-(piperidin-4-yl)isoxazole-3-carboxamide,
5-[2,4-dihydroxy-6-(4-nitrophenoxy)phenyl]-N-[1-(propan-2-yl)piperidin-4-yl]isoxazole-3-carboxamide,
N-(1-cyclohexylpiperidin-4-yl)-5-[2,4-dihydroxy-6-(4-nitrophenoxy)phenyl]isoxazole-3-carboxamide,
5-[2,4-dihydroxy-6-(4-nitrophenoxy)phenyl]-N-[1-(4-hydroxycyclohexyl)piperidin-4-yl]isoxazole-3-carboxamide,
5-[2,4-dihydroxy-6-(4-nitrophenoxy)phenyl]-N-[1-(4-methoxycyclohexyl)piperidin-4-yl]isoxazole-3-carboxamide,
5-[2,4-dihydroxy-6-(4-nitrophenoxy)phenyl]-N-[1-(4-aminocyclohexyl)piperidin-4-yl]isoxazole-3-carboxamide,
5-[2,4-dihydroxy-6-(4-nitrophenoxy)phenyl]-N-[1-(4-(dimethylamino)cyclohexyl)piperidin-4-yl]isoxazole-3-carboxamide,
5-[2,4-dihydroxy-6-(4-nitrophenoxy)phenyl]-N-[1-(4-acetylamino)cyclohexyl)piperidin-4-yl]isoxazole-3-carboxamide,
5-[2,4-dihydroxy-6-(4-nitrophenoxy)phenyl]-N-[1-(4-aminomethyl)cyclohexyl)piperidin-4-yl]isoxazole-3-carboxamide,
5-[2,4-dihydroxy-6-(4-nitrophenoxy)phenyl]-N-[1-(4-dimethylaminomethyl)cyclohexyl)piperidin-4-yl]isoxazole-3-carboxamide,
N-[1-(4,4-difluorocyclohexyl)piperidin-4-yl]-5-[2,4-dihydroxy-6-(4-nitrophenoxy)phenyl]isoxazole-3-carboxamide,
5-[2,4-dihydroxy-6-(4-nitrophenoxy)phenyl]-N-[1-(1,4-dioxaspiro[4.5]dec-8-yl)piperidin-4-yl]isoxazole-3-carboxamide,
5-[2,4-dihydroxy-6-(4-nitrophenoxy)phenyl]-N-(1'-methyl-1,4'-bipiperidin-4-yl)isoxazole-3-carboxamide,
5-[2,4-dihydroxy-6-(4-nitrophenoxy)phenyl]-N-[1-(tetrahydro-2H-pyran-4-yl)piperidin-4-yl]isoxazole-3-carboxamide,
5-[2,4-dihydroxy-6-(4-dimethylaminophenoxy)phenyl]-N-[1-(4-hydroxycyclohexyl)piperidin-4-yl]isoxazole-3-carboxamide,
5-[2,4-dihydroxy-6-(4-dimethylaminophenoxy)phenyl]-N-[1-(4-methoxycyclohexyl)piperidin-4-yl]isoxazole-3-carboxamide,
5-[2,4-dihydroxy-6-(4-dimethylaminophenoxy)phenyl]-N-[1-(4-aminocyclohexyl)piperidin-4-yl]isoxazole-3-carboxamide,
5-[2,4-dihydroxy-6-(4-dimethylaminophenoxy)phenyl]-N-[1-(4-(dimethylamino)cyclohexyl)piperidin-4-yl]isoxazole-3-carboxamide,
5-[2,4-dihydroxy-6-(4-dimethylaminophenoxy)phenyl]-N-[1-(4-acetylamino)cyclohexyl)piperidin-4-yl]isoxazole-3-carboxamide, 5-[2,4-dihydroxy-6-(4-dimethylaminophenoxy)phenyl]-N-[1-(4-aminomethyl)cyclohexyl)piperidin-4-yl]isoxazole-3-carboxamide, 5-[2,4-dihydroxy-6-(4-dimethylaminophenoxy)phenyl]-N-[1-(4-dimethylaminomethyl)cyclohexyl)piperidin-4-yl]isoxazole-3-carboxamide, N-[1-(4,4-difluorocyclohexyl)piperidin-4-yl]-5-[2,4-dihydroxy-6-(4-dimethylaminophenoxy)phenyl]isoxazole-3-carboxamide, N-[1-(4,4-difluorocyclohexyl)piperidin-4-yl]-5-[2,4-dihydroxy-6-(4-(propan-2-yl-amino)phenoxy)phenyl]isoxazole-3-carboxamide, 5-[2,4-dihydroxy-6-(4-(propan-2-yl-amino)phenoxy)phenyl]-N-[1-(1,4-dioxaspiro[4.5]dec-8-yl)piperidin-4-yl]isoxazole-3-carboxamide, 5-[2,4-dihydroxy-6-(4-(propan-2-yl-amino)phenoxy)phenyl]-N-(1'-methyl-1,4'-bipiperidin-4-yl)isoxazole-3-carboxamide, 5-[2,4-dihydroxy-6-(4-(propan-2-yl-amino)phenoxy)phenyl]-N-[1-(tetrahydro-2H-pyran-4-yl)piperidin-4-yl]isoxazole-3-carboxamide, N-(1-cyclohexylpiperidin-4-yl)-5-[2,4-dihydroxy-6-(4-cyanophenoxy)phenyl]isoxazole-3-carboxamide, 5-[2,4-dihydroxy-6-(4-cyanophenoxy)phenyl]-N-[1-(4-hydroxycyclohexyl)piperidin-4-yl]isoxazole-3-carboxamide, 5-[2,4-dihydroxy-6-(4-cyanophenoxy)phenyl]-N-[1-(4-methoxycyclohexyl)piperidin-4-yl]isoxazole-3-carboxamide, 5-[2,4-dihydroxy-6-(4-cyanophenoxy)phenyl]-N-[1-(4-aminocyclohexyl)piperidin-4-yl]isoxazole-3-carboxamide, 5-[2,4-dihydroxy-6-(4-cyanophenoxy)phenyl]-N-[1-(4-dimethylaminocyclohexyl)piperidin-4-yl]isoxazole-3-carboxamide, 5-[2,4-dihydroxy-6-(4-cyanophenoxy)phenyl]-N-[1-(4-acetylaminocyclohexyl)piperidin-4-yl]isoxazole-3-carboxamide, 5-[2,4-dihydroxy-6-(4-cyanophenoxy)phenyl]-N-[1-(4-aminomethylcyclohexyl)piperidin-4-yl]isoxazole-3-carboxamide, 5-[2,4-dihydroxy-6(4-cyanophenoxy)phenyl]-N-[1-(4-dimethylaminomethylcyclohexyl)piperidin-4-yl]isoxazole-3-carboxamide, N-[1-(4,4-difluorocyclohexyl)piperidin-4-yl]-5-[2,4-dihydroxy-6-(4-cyanophenoxy)phenyl]isoxazole-3-carboxamide, 5-[2,4-dihydroxy-6-(4-cyanophenoxy)phenyl]-N-[1-(1,4-dioxaspiro[4.5]dec-8-yl)piperidin-4-yl]isoxazole-3-carboxamide, 5-[2,4-dihydroxy-6-(4-cyanophenoxy)phenyl]-N-(1'-methyl-1,4'-bipiperidin-4-yl)isoxazole-3-carboxamide, 5-[2,4-dihydroxy-6-(4-cyanophenoxy)phenyl]-N-[1-(tetrahydro-2H-pyran-4-yl)piperidin-4-yl]isoxazole-3-carboxamide, N-(1-cyclohexylpiperidin-4-yl)-5-[2,4-dihydroxy-6-(4-carbamoylphenoxy)phenyl]isoxazole-3-carboxamide, 5-[2,4-dihydroxy-6-(4-(propan-2-yl-amino)phenoxy)phenyl]-N-[1-(4-hydroxycyclohexyl)piperidin-4-yl]isoxazole-3-carboxamide, 5-[2,4-dihydroxy-6-(4-carbamoylphenoxy)phenyl]-N-[1-(4-methoxycyclohexyl)piperidin-4-yl]isoxazole-3-carboxamide, 5-[2,4-dihydroxy-6-(4-carbamoylphenoxy)phenyl]-N-[1-(4-aminocyclohexyl)piperidin-4-yl]isoxazole-3-carboxamide, 5-[2,4-dihydroxy-6-(4-carbamoylphenoxy)phenyl]-N-[1-(4-(dimethylamino)cyclohexyl)piperidin-4-yl]isoxazole-3-carboxamide, 5-[2,4-dihydroxy-6-(4-carbamoylphenoxy)phenyl]-N-[1-(4-(acetylamino)cyclohexyl)piperidin-4-yl]isoxazole-3-carboxamide, 5-[2,4-dihydroxy-6-(4-carbamoylphenoxy)phenyl]-N-[1-(4-(aminomethyl)cyclohexyl)piperidin-4-yl]isoxazole-3-carboxamide, 5-[2,4-dihydroxy-6-(4-carbamoylphenoxy)phenyl]-N-[1-(4-dimethylaminomethyl)cyclohexyl)piperidin-4-yl]isoxazole-3-carboxamide, N-[1 (4,4-difluorocyclohexyl)piperidin-4-yl]-5-[2,4-dihydroxy-6-(4-carbamoylphenoxy)phenyl]isoxazole-3-carboxamide, 5-[2,4-dihydroxy-6-(4-carbamoylphenoxy)phenyl]-N-[1-(1,4-dioxaspiro[4.5]dec-8-yl)piperidin-4-yl]isoxazole-3-carboxamide, 5-[2,4-dihydroxy-6-(4-carbamoylphenoxy)phenyl]-N-(1'-methyl-1,4'-bipiperidin-4-yl)isoxazole-3-carboxamide, 5-[2,4-dihydroxy-6-(4-carbamoylphenoxy)phenyl]-N-[1-(tetrahydro-2H-pyran-4-yl)piperidin-4-yl]isoxazole-3-carboxamide, 3-[2-(4-carbamoylphenoxy)-4,6-dihydroxyphenyl]-N-[1-(tetrahydro-2H-pyran-4-yl)piperidin-4-yl]isoxazole-5-carboxamide, 3-[2-(4-carbamoylphenoxy)-4,6-dihydroxyphenyl]-N-(1-cyclohexylpiperidin-4-yl)isoxazole-5-carboxamide, 3-[2-(4-carbamoylphenoxy)-4,6-dihydroxyphenyl]-N-[1-(4,4-difluorocyclohexyl)piperidin-4-yl]isoxazole-5-carboxamide, 3-[2-(4-carbamoylphenoxy)-4,6-dihydroxyphenyl]-N-(1'-methyl-1,4'-bipiperidin-4-yl)isoxazole-5-carboxamide, N-(1-cyclohexylpiperidin-4-yl)-3-[2,4-dihydroxy-6-(4-nitrophenoxy)phenyl]isoxazole-5-carboxamide, 3-[2,4-dihydroxy-6-(4-nitrophenoxy)phenyl]-N-[1-(tetrahydro-2H-pyran-4-yl)piperidin-4-yl]isoxazole-5-carboxamide, 3-[2,4-dihydroxy-6-(4-nitrophenoxy)phenyl]-N-(1'-methyl-1,4'-bipiperidin-4-yl)isoxazole-5-carboxamide, 5-[2,4-dihydroxy-6-(4-nitrophenoxy)phenyl]-N-[2-(methylamino)ethyl]isoxazole-3-carboxamide, 5-[2,4-dihydroxy-6-(4-nitrophenoxy)phenyl]-N-(1-ethylpiperidin-3-yl)isoxazole-3-carboxamide, N-(1-acetylpiperidin-4-yl)-5-[2,4-dihydroxy-6-(4-nitrophenoxy)phenyl]isoxazole-3-carboxamide, 5-[2,4-dihydroxy-6-(4-nitrophenoxy)phenyl]-N-(1,2,2,6,6-pentamethylpiperidin-4-yl)isoxazole-3-carboxamide, 5-[2,4-dihydroxy-6-(4-nitrophenoxy)phenyl]-N-(piperidin-4-yl)isoxazole-3-carboxamide, N-(1-cyclopentylpiperidin-4-yl)-5-[2,4-dihydroxy-6-(4-nitrophenoxy)phenyl]isoxazole-3-carboxamide, N-(1-cycloheptylpiperidin-4-yl)-5-[2,4-dihydroxy-6-(4-nitrophenoxy)phenyl]isoxazole-3-carboxamide, N-(1-benzylpiperidin-4-yl)-5-[2,4-dihydroxy-6-(4-nitrophenoxy)phenyl]isoxazole-3-carboxamide, N-(1-cyclohexylpiperidin-4-yl)-5-{2-[4-(dimethylamino)phenoxy]-4,6-dihydroxyphenyl}isoxazole-3-carboxamide-1,3-dioxolane, 5-{2-[4-(dimethylamino)phenoxy]-4,6-dihydroxyphenyl}-N-[1-(1,5-dioxaspiro[5.5]undec-9-yl)piperidin-4-yl]isoxazole-3-carboxamide, 5-{2-[4-(dimethylamino)phenoxy]-4,6-dihydroxyphenyl}-N-[1-(3,3-dimethyl-1,5-dioxaspiro[5.5]undec-9-yl)piperidin-4-yl]isoxazole-3-carboxamide, 5-{2-[4-(dimethylamino)phenoxy]-4,6-dihydroxyphenyl}-N-[1-(7,12-dioxaspiro[5.6]dodec-3-yl)piperidin-4-yl]isoxazole-3-carboxamide,
5-{2-[4-(dimethylamino)phenoxy]-4,6-dihydroxyphenyl}-N-{1-[(2R,3S)-2,3-dimethyl-1,4-dioxaspiro[4.5]dec-8-yl]piperidin-4-yl}isoxazole-3-carboxamide,
N-[1-(4,4-difluorocyclohexyl)piperidin-4-yl]-5-{2-[4-(dimethylamino)phenoxy]-4,6-dihydroxyphenyl}isoxazole-3-carboxamide,
N-[1'-(cyclohexylmethyl)-1,4'-bipiperidin-4-yl]-5-{2-[4-(dimethylamino)phenoxy]-4,6-dihydroxyphenyl}isoxazole-3-carboxamide,
N-(1'-benzyl-1,4'-bipiperidin-4-yl)-5-{2-[4-(dimethylamino)phenoxy]-4,6-dihydroxyphenyl}isoxazole-3-carboxamide,
tert-butyl(4-{4-[({5-[2,4-dihydroxy-6-(4-nitrophenoxy)phenyl]isoxazol-3-yl}carbonyl)amino]piperidin-1-yl}butyl)carbamate,
N-[1-(4-aminobutyl)piperidin-4-yl]-5-[2,4-dihydroxy-6-(4-nitrophenoxy)phenyl]isoxazole-3-carboxamide
tert-butyl(3-{4-[({5-[2,4-dihydroxy-6-(4-nitrophenoxy)phenyl]isoxazol-3-yl}carbonyl)amino]piperidin-1-yl}propyl)carbamate,
N-[1-(3-aminopropyl)piperidin-4-yl]-5-[2,4-dihydroxy-6-(4-nitrophenoxy)phenyl]isoxazole-3-carboxamide,
5-{2,4-dihydroxy-6-[4-(tetrahydro-2H-pyran-4-ylamino)phenoxy]phenyl}-N-(1-methylpiperidin-4-yl)isoxazole-3-carboxamide,
5-{2-[4-(dimethylamino)phenoxy]-4,6-dihydroxyphenyl}-N-(1-methylpiperidin-4-yl)isoxazole-3-carboxamide,
5-{2,4-dihydroxy-6-[4-(propan-2-ylamino)phenoxy]phenyl}-N-(1-methylpiperidin-4-yl)isoxazole-3-carboxamide,
5-{2-[4-(cyclobutylamino)phenoxy]-4,6-dihydroxyphenyl}-N-(1-methylpiperidin-4-yl)isoxazole-3-carboxamide,
5-{2,4-dihydroxy-6-[4-(pyrrolidin-1-yl)phenoxy]phenyl}-N-(1-methylpiperidin-4-yl)isoxazole-3-carboxamide,
3-[2,4-dihydroxy-6-(4-nitrophenoxy)phenyl]-N-(1-methylpiperidin-4-yl)isoxazole-5-carboxamide,
3-{2-[4-(dimethylamino)phenoxy]-4,6-dihydroxyphenyl}-N-(1-methylpiperidin-4-yl)isoxazole-5-carboxamide,
tert-butyl 4-{[(3-{2-[4-(dimethylamino)phenoxy]-4,6-dihydroxyphenyl}isoxazol-5-yl)carbonyl]amino}piperidine-1-carboxylate,
3-{2-[4-(dimethylamino)phenoxy]-4,6-dihydroxyphenyl}-N-(piperidin-4-yl)isoxazole-5-carboxamide,
3-{2-[4-(dimethylamino)phenoxy]-4,6-dihydroxyphenyl}-N-[1-(1,4-dioxaspiro[4.5]dec-8-yl)piperidin-4-yl]isoxazole-5-carboxamide,
3-{2-[4-(dimethylamino)phenoxy]-4,6-dihydroxyphenyl}-N-[1-(3,3-dimethyl-1,5-dioxaspiro[5.5]undec-9-yl)piperidin-4-yl]isoxazole-5-carboxamide,
5-[2-(benzyloxy)-4,6-dihydroxyphenyl]-N-(1-methylpiperidin-4-yl)isoxazole-3-carboxamide,
4-(3-aminoisoxazol-5-yl)-5-(4-nitrophenoxy)benzene-1,3-diol,
1-{5-[2,4-dihydroxy-6-(4-nitrophenoxy)phenyl]isoxazol-3-yl}-3 (1-methylpiperidin-4-yl)urea,
N-{5-[2,4-dihydroxy-6-(4-nitrophenoxy)phenyl]isoxazol-3-yl}-1-methylpiperidine-4-carboxamide and
N-{5-[2,4-dihydroxy-6-(4-nitrophenoxy)phenyl]isoxazol-3-yl}ethanesulfonamide.

4. A pharmaceutical composition comprising a therapeutically effective amount of a compound of formula (I), as defined in claim 1, and at least one pharmaceutically acceptable carrier and/or diluent.

5. A pharmaceutical composition according to claim 4 further comprising one or more chemotherapeutic agents.

* * * * *